US012633387B2

(12) United States Patent
Mccabe et al.

(10) Patent No.: US 12,633,387 B2
(45) **Date of Patent: *May 19, 2026**

(54) SYSTEMS AND METHODS FOR MANAGING, MONITORING, AND TREATING PATIENT CONDITIONS

(71) Applicant: Pharaoh Neuro, Inc., Minneapolis, MN (US)

(72) Inventors: Aaron Richard Mccabe, Edina, MN (US); Don William Eldon Evans, Saint Paul, MN (US); Laura Marie Zitella Verbick, North St. Paul, MN (US); William Raymond Bushnell, Minneapolis, MN (US); Abhi Vase, Los Altos Hills, CA (US); Owen Seymour, Minneapolis, MN (US)

(73) Assignee: PHARAOH NEURO, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/770,955

(22) Filed: Jul. 12, 2024

(65) Prior Publication Data

US 2024/0371482 A1 Nov. 7, 2024

Related U.S. Application Data

(63) Continuation of application No. 17/576,430, filed on Jan. 14, 2022, now Pat. No. 12,068,061.

(Continued)

(51) Int. Cl.
*G16H 10/60* (2018.01)

(52) U.S. Cl.
CPC .................................. *G16H 10/60* (2018.01)

(58) Field of Classification Search
None
See application file for complete search history.

(56) References Cited

U.S. PATENT DOCUMENTS

| | | | | |
|---|---|---|---|---|
| 8,435,204 | B2 | 5/2013 | Lad et al. | |
| 9,495,512 | B2 * | 11/2016 | Nakada | G16H 40/67 |

(Continued)

FOREIGN PATENT DOCUMENTS

| | | | |
|---|---|---|---|
| EP | 2011435 | A2 | 1/2009 |
| EP | 2777488 | A1 | 9/2014 |

OTHER PUBLICATIONS

Yamada et al., "Longitudinal Morphological Changes during Recovery from Brain Deformation Due to Idiopathic Normal Pressure Hydrocephalus after Venticuloperitoneal Shunt Surgery," Scientific Reports, vol. 9, No. 1, 13 pages, Nov. 21, 2019. (Year 2019).

(Continued)

*Primary Examiner* — John A Pauls
(74) *Attorney, Agent, or Firm* — Seager, Tufte & Wickhem LLP

(57) ABSTRACT

Systems, devices, user interfaces, and methods for managing patient conditions. A system for monitoring and/or managing a patient suffering from a brain condition may include a controller obtaining and/or storing data related to one or more monitored patient parameters contributing to the brain condition of the patient and displaying values of the one or more monitored patient parameters in trend lines over time on a user interface. The displayed trend lines may represent values of ventricular CSF volume, values of IVH volume, total ventricular volume in the brain, and/or values of other suitable parameters. The data related to the one or more monitored patient parameters may include images of the patient's brain and/or data derived from images of the patient's brain and/or suitable patient data.

20 Claims, 61 Drawing Sheets

Related U.S. Application Data

(60) Provisional application No. 63/294,246, filed on Dec. 28, 2021, provisional application No. 63/137,969, filed on Jan. 15, 2021.

(56) References Cited

U.S. PATENT DOCUMENTS

| | | | | |
|---|---|---|---|---|
| 9,536,052 | B2 | 1/2017 | Amarasingham et al. | |
| 9,658,756 | B2 | 5/2017 | Freeman et al. | |
| 9,864,840 | B2 | 1/2018 | Grady et al. | |
| 11,826,531 | B2 | 11/2023 | Vase | |
| 2009/0005703 | A1 | 1/2009 | Fasciano | |
| 2009/0192823 | A1 * | 7/2009 | Hawkins | G06Q 10/06 715/767 |
| 2012/0039816 | A1 * | 2/2012 | Benavides | A61P 25/28 424/9.44 |
| 2013/0032147 | A1 * | 2/2013 | Robinson | A61M 16/0051 128/204.18 |
| 2014/0015856 | A1 | 1/2014 | Xiao et al. | |
| 2014/0275818 | A1 | 9/2014 | Kassem et al. | |
| 2014/0275819 | A1 | 9/2014 | Kassem et al. | |
| 2016/0000517 | A1 | 1/2016 | Kehat et al. | |
| 2016/0051801 | A1 | 2/2016 | Vase | |
| 2019/0010547 | A1 | 1/2019 | Willeit et al. | |
| 2019/0105475 | A1 | 4/2019 | Lad et al. | |
| 2020/0046952 | A1 | 2/2020 | Vase | |
| 2020/0046953 | A1 | 2/2020 | Vase | |
| 2020/0273551 | A1 * | 8/2020 | Calderon | G06F 16/248 |
| 2021/0052916 | A1 * | 2/2021 | Isola | A61N 5/1048 |

OTHER PUBLICATIONS

Heldt et al., "Intracranial Pressure and Intracranial Elastance Monitoring in Neurocritical Care," Annual Review Biomedical Engineering, vol. 21, pp. 523-549. Jun. 1, 2019. (Year:2019).

International Search Report and Written Opinion dated Apr. 21, 2022 for International Application No. PCT/US2022/012518.

Koubeissi et al., "In-Hospital Morality of Generalized Convulsive Status Epilepticus: A Large US Sample," Neurology, vol. 69, No. 9, pp. 886-893, Aug. 28, 2007.

Brain Trauma Foundation, American Association of Neurological Surgeons, Congress of Neurological Surgeons, Guidelines for the Management of Severe Traumatic Brain Injury 3rd Edition, Journal of Neurotrauma, vol. 24, pp. 1-116, Apr. 26, 2007.

Young et al., "An Assessment of Non-Convulsive Seizures in the Intensive Care Unit using Continuous EEG Monitoring: An Investigation of Variables Associated with Mortality," Neurology, vol. 47, No. 1, pp. 83-89, Jul. 1, 1996.

Wijayatilake et al., "Updates in the Measurement of Intracranial Pressure in Traumatic Brain Injury," Current Opinion in Anaesthesiology, vol. 25, No. 5, pp. 540-547, Oct. 2012.

Delorenzo et al., "Epidemiology of Status Epilepticus," Journal of Clinical Neurophysiology, vol. 12, No. 4, pp. 316-325. Jul. 12, 1995.

Lowenstein et al., "Status Epilepticus at an Urban Public Hospital in the 1980's," Neurology, vol. 42, No. 3 (Part 1) pp. 483-488, Mar. 1993.

Mazarati et al., "Time Dependent Decrease in the Effectiveness of Antiepileptic Drugs during the Course of Self-Sustaining Status Epilepticus," Brain Research, vol. 814 No. (1-2), pp. 179-185 Dec. 14, 1998.

Delorenzo et al., "Status Epilepticus in Children, Adults, and the Elderly," Epilepsia, vol. 33 Supplement 4:S15-S25. Jul. 1992.

Metzger et al., "Year in Review 2008: Critical Care-Trauma," Critical Care, vol. 13, No. 5, pp. 1-5, Oct. 21, 2009.

Marmarou et al., "Impact of ICP Instability and Hypotension on Outcome in Patients with Severe Head Trauma," Journal of Neurosurgery, vol. 75: Issue Supplement, pp. S59-S66, Nov. 1991.

Albrecht et al., "Occurence of Potentially Detrimental Temperature Altercations in Hospitalized Patients at Risk for Brain Injury," Mayo Clinic Proceedings, vol. 73, Issue 7, pp. 629-635. Jul. 1998.

Claassen et al., "Predictors of Functional Disability and Mortality after Status Epilepticus," Neurology, vol. 58, No. 1, pp. 139-142. Jan. 8, 2022.

Dorfman et al., "Decompressive Laparotomy for Refractory Intracranial Hypertension after Traumatic Brain Injury," Neurocritical Care, vol. 15, pp. 516-518. Apr. 26, 2011.

Miller et al., "Significance of Intracranial Hypertension in Severe Head Injury," Journal of Neurosurgery, vol. 47, No. 4, pp. 503-516. Oct. 1, 1997.

Ghajar et al., "Improved Outcome from Traumatic Coma using Only Ventricular Cerebrospinal Fluid Drainage for Intracranial Pressure Control," Advances in Neurosurgery, vol. 21, pp. 173-177, 1993.

Treiman et al., "A Comparison of Four Treatments for Generalized Convulsive Status Epilepticus," The England Journal of Medicine, vol. 339, No. 12, pp. 792-798. Sep. 17, 1998.

Balami et al., "Complications of Intracerebral Hemorrhage," Lancet Neurology, vol. 11, Issue 1, pp. 101-118, Jan. 2012.

Claassen et al., "Treatment of Refractory Status Epilepticus with Pentobarbital, Propofol, or Midazolam: a Systematic Review," Epilepsia, vol. 43, No. 2, pp. 146-153, Feb. 2002.

Commichau et al., "Risk Factors for Fever in the Neurologic Intensive Care Unit," Neurology, Volme 60, No. 5, pp. 837-841, Mar. 11, 2003.

Diringer et al., "Elevated Body Temperature Independently Contributes to Increased Length of Stay in Neurologic Intensive Care Unit Patients," Critical Care Medicine, vol. 32, No. 7, pp. 1489-1495. Jul. 2004.

Hemphill et al., "The ICH Score," American Heart Association, vol. 32, Issue 4, pp. 891-897, Jan. 23, 2001.

Holtkamp et al., "Predictors and Prognosis of Refractory Status Epilepticus Treated in a Neurological Intensive Care Unit," Journal of Neurology, Neurosurgery & Psychiatry, vol. 76, No. 4, pp. 534-539. Apr. 2005.

Juul et al., "Intracranial Hypertension and Cerebral Perfusion Pressure: Influence on Neurological Deterioration and Outcome in Severe Head Injury," Journal of Neurosurgery, vol. 92, No. 1, pp. 1-6. Jan. 2000.

Kilpatrick et al., "Hyperthemia in the Neurosurgical Intensive Care Unit," Neurosurgery, vol. 47, No. 4, pp. 850-855. Oct. 2000.

Logroscino et al., "Time Trends in Incidence, Mortality, and Case-Fatality after First Episode of Status Epilepticus," Epilepsia, vol. 42, No. 8, pp. 1031-1035, Dec. 20, 2001.

Lowenstein et al., "It's Time to Revise the Definition of Status Epilepticus," Epilepsia, vol. 40, No. 1, pp. 120-122. Jan. 1, 1999.

Mayer et al., "Refractory Status Epilepticus: Frequency, Risk Factors, and Impact on Outcome," Archives of Neurology, vol. 59, No. 2, pp. 205-210. Feb. 2002.

Oliveira-Filho et al., "Fever in Subarachnoid Hemorrhage: Relationship to Vasospasm and Outcome," Neurology, vol. 56, No. 10, pp. 1299-1304. May 22, 2001.

Reith et al., "Body Temperature in Acute Stroke: Relation to Stroke Severity, Infarct Size, Mortality, and Outcome," The Lancet, vol. Issue 8999, pp. 422-425. Feb. 17, 1996.

Rossi et al., "Brain Temperature, Body Core Temperature, and Intracranial Pressure in Acute Cerebral Damage," Journal of Neurology, Neurosurgery & Psychiatry, vol. 71, No. 4, pp. 448-454. Oct. 1, 2001.

Schwarz et al., "Incidence and Prognostic Significance of Fever following Intracerebral Hemorrhage," Neurology, vol. 54, No. 2, pp. 354-361. Jan. 25, 2000.

Stocchetti et al., "Pyrexia in Head-Injured Patients Admitted to Intensive Care," Intensive Care Medicine, vol. 28, pp. 1555-1562. Nov. 2002.

Thompson et al., "Hyperthermia Following Traumatic Brain Injury: A Critical Evaluation," Neurobiology of Disease, vol. 12, No. 3, pp. 163-173, Apr. 2003.

* cited by examiner

SYSTEMS AND METHODS FOR MANAGING, MONITORING, AND TREATING PATIENT CONDITIONS

CROSS REFERENCE TO RELATED APPLICATIONS

The present application is a continuation of U.S. application Ser. No. 17/576,430, filed Jan. 14, 2022, which claims the benefit of and priority to U.S. Prov. Patent App. No. 63/294,246, filed Dec. 28, 2021, and claims the benefit of U.S. Prov. Patent App. No. 63/137,969, filed Jan. 15, 2021, the disclosures of which are incorporated herein by reference.

TECHNICAL FILED

The present disclosure relates to systems, modules, interfaces, and methods for diagnosing, treating, and managing patient conditions.

BACKGROUND

A wide variety of medical devices, systems, interfaces, and methods have been developed for medical use. Some of these devices, systems, interfaces, and methods include control systems, pumps, guidewires, catheters, surgical instruments, user interfaces, and the like. These devices, systems, and interfaces are manufactured by and/or configured in one or more different manners, and may be used according to any one of a variety of methods. Of the known medical devices, systems, interfaces, and methods, each has certain advantages and disadvantages. There is an ongoing need to provide alternative medical devices as well as alternative methods for manufacturing and using medical devices.

SUMMARY

This disclosure provides design, material, interface, manufacturing method, and use alternatives for medical devices and/or systems. One example includes a patient management system. The patient management system may include a user interface including a display, and a controller coupled to the user interface and configured to store data related to one or more patient parameters of a patient. The controller may be programmed to obtain data related to the one or more patient parameters, the one or more patient parameters contribute to a brain condition of the patient, and instruct the user interface to display values of or related to the one or more patient parameters in trend lines over time.

Alternatively or additionally to any of the embodiments above, the controller may be programed to obtain data related to two or more patient parameters.

Alternatively or additionally to any of the embodiments above, the controller may be programmed to display values of the two or more patient parameters in trend lines over a timeline common to the trend lines of the values of the two or more patient parameters.

Alternatively or additionally to any of the embodiments above, the controller may be programmed to update the trendlines and timeline as data related to the two or more patient parameters is obtained.

Alternatively or additionally to any of the embodiments above, the controller may be programmed to receive a selection of a time on the timeline and the selection of the time on the timeline causes the controller to provide a value for the two or more patient parameters at the time selected.

Alternatively or additionally to any of the embodiments above, the one or more patient parameters may include at least one patient parameter selected from the group consisting of an anatomical parameter and a physiological parameter.

Alternatively or additionally to any of the embodiments above, the one or more patient parameters may include at least one patient parameter selected from the group consisting of intracranial hemorrhage (ICH) volume, edema volume, total ventricular volume, ventricular cerebral spinal fluid (CSF) volume, intraventricular hemorrhage (IVH) volume, total ventricular volume, midline shift, mass effect, ventricular pressure, intracranial pressure (ICP), systolic blood pressure (BP), diastolic BP, heart rate, respiratory rate, temperature, blood glucose, and Glasgow Coma Scale (GCS).

Alternatively or additionally to any of the embodiments above, the controller may be programmed to receive one or more inputs to edit the obtained data related to the one or more patient parameters.

Alternatively or additionally to any of the embodiments above, the controller may be programmed to receive a selection to edit a configuration of the display.

Alternatively or additionally to any of the embodiments above, the controller may be programmed to cause the user interface to display values of one or more threshold values along the trend lines for at least one of the one or more of the one or more patient parameters.

Alternatively or additionally to any of the embodiments above, the controller is programmed to receive a selection to adjust a threshold value of the one or more thresholds.

Alternatively or additionally to any of the embodiments above, the controller may be programmed to provide a notification if a value of the one or more patient parameters exceeds a threshold.

Alternatively or additionally to any of the embodiments above, the controller may be programmed to receive an image of a brain of the patient and display the image.

Alternatively or additionally to any of the embodiments above, the controller may be programmed to cause the image of the brain of the patient to be displayed adjacent the trend lines of the one or more patient parameters.

Alternatively or additionally to any of the embodiments above, the controller may be programmed to identify on the display portions of the image associated with the values of the one or more patient parameters.

Alternatively or additionally to any of the embodiments above, the controller may be programed to determine the values of the one or more patient parameters from the image.

Alternatively or additionally to any of the embodiments above, the image displayed may be a two-dimensional (2D) image.

Alternatively or additionally to any of the embodiments above, the image displayed may be a three-dimensional (3D) image.

Alternatively or additionally to any of the embodiments above, the controller may be programmed to display an indication on the trend lines of the one or more patient parameters, the indication indicates when an image of a brain of the patient was taken and/or is to be taken.

Alternatively or additionally to any of the embodiments above, the controller may be programmed to display an indication along a timeline common to the trend lines of the values of the one or more patient parameters, the indication indicates when an image of a brain of the patient was taken and/or is to be taken.

Another example may include a patient management system. The patient management system may include a controller configured to store data related to one or more patient parameters of a patient. The controller may be programmed to receive a plurality of images from CT scans of a brain of the patient, the plurality of images are taken over time, identify one or more locations in the images, the one or more locations are associated with the one or more patient parameters, identify values of the one or more patient parameters based on the identified locations in the plurality images, and display the values of the one or more patient parameters of the patient over time.

Alternatively or additionally to any of the embodiments above, the controller may be programmed to identify a plurality of locations in the images, the plurality of locations are associated with the one or more patient parameters, and identify values of two or more of the patient parameters based on the plurality of locations identified in the images.

Alternatively or additionally to any of the embodiments above, the system may further include a user interface having a display, and the controller may be programmed to graphically display an image of the plurality of images and graphically indicate on the image displayed a location of the one or more locations in the images that are identified.

Alternatively or additionally to any of the embodiments above, the system may further include a user interface having a display, and the controller may be programmed to graphically display the values of the one or more patient parameters of the patient on the display adjacent an image of the plurality of images.

Alternatively or additionally to any of the embodiments above, the controller may be programmed to display the values of the one or more patient parameters in trend lines over a range of time in a timeline, and indicate on the trend lines when the image of the plurality of images was taken.

Alternatively or additionally to any of the embodiments above, the controller may be programed to indicate on the trend lines when each of the plurality of images was taken.

Alternatively or additionally to any of the embodiments above, the controller may be programmed to indicate on the image a location of the one or more locations in the images that are identified, display the values of the one or more patient parameters in trend lines over a range of time in a timeline, and graphically associate the location of the one or more locations with a trend line of the trend lines displayed.

Alternatively or additionally to any of the embodiments above, graphically associating the location of the one or more locations with a trend line of the trend lines displayed may include associating a same color with the location of the one or more locations and the trend line of the trend lines displayed.

Alternatively or additionally to any of the embodiments above, the controller may be programed to use a computer vision algorithm to identify the one or more locations in the images.

Another example may include a computer readable medium having stored thereon in a non-transitory state a program code for use by a computing device, the program code causing the computing device to execute a method of graphically representing one or more volumes in a brain of a patient. The method may include identifying a ventricular cerebral spinal fluid (CSF) volume in the brain of the patient, displaying a value of the ventricular cerebral spinal fluid volume on a display of a user interface, identifying an intraventricular hemorrhage (IVH) volume in the brain of the patient, displaying a value of intraventricular hemorrhage on the display, determining a total ventricular volume in the brain of the patient based on the ventricular cerebral spinal fluid volume and the intraventricular hemorrhage volume, and displaying a value of the total ventricular volume on the display.

Alternatively or additionally to any of the embodiments above, the method may further include identifying the ventricular CSF volume at each of a plurality of time, and identifying the IVH volume at each of the plurality of times.

Alternatively or additionally to any of the embodiments above, the method may further include displaying on the display values of the ventricular CSF volume at each of the plurality of times and a CSF trend line through the displayed values of the ventricular CSF volume, displaying on the display values of the IVH volume at each of the plurality of times and an IVH trend line through the displayed values of the IVH volume, and displaying on the display values of the total ventricular volume at each of the plurality of times and a total volume trend line through the display values of the total ventricular volume.

Alternatively or additionally to any of the embodiments above, the method may further include identifying the ventricular CSF volume and the IVH volume using an image from a CT scan of the brain of the patient.

Alternatively or additionally to any of the embodiments above, the method may further include using a computer vision algorithm to identify the ventricular CSF volume and the IVH volume using an image from a CT scan.

Alternatively or additionally to any of the embodiments above, the method may further include displaying an image from a CT scan of the brain of the patient adjacent the value of the total ventricular volume on the display of the user interface.

Alternatively or additionally to any of the embodiments above, the method may further include graphically indicating the ventricular CSF volume identified and the IVH volume identified on the image from the CT scan displayed on the display.

Another example may include a computer readable medium having stored thereon in a non-transitory state a program code for use by a computing device, the program code causing the computing device to execute a method of operating a patient management system. The method may include receiving data related to one or more patient parameters from one or more sources, the one or more patient parameters contribute to a brain condition of the patient, and instructing a user interface to display values of or related to the one or more patient parameters in trend lines over time.

Alternatively or additionally to any of the embodiments above, the method may further include receiving data related to two or more patient parameters from two or more sources.

Alternatively or additionally to any of the embodiments above, the method may further include instructing the user interface to display values of the two or more patient parameters in trend lines over a timeline common to the trend lines of the values of the two or more patient parameters.

Alternatively or additionally to any of the embodiments above, the method may further include instructing the user interface to update the trendlines and timeline as data related to the two or more patient parameters is obtained.

Alternatively or additionally to any of the embodiments above, the method may further include receiving a selection of a time on the timeline, and providing a value for the two or more patient parameters at the time selected in response to receiving the selection of the time on the timeline.

Alternatively or additionally to any of the embodiments above, the method may further include receiving one or more inputs to edit the obtained data related to the one or more patient parameters.

Alternatively or additionally to any of the embodiments above, the method may further include receiving a selection to edit a configuration of the display.

Alternatively or additionally to any of the embodiments above, the method may further include instructing the user interface to display values of one or more threshold values along the trend lines for at least one of the one or more of the one or more patient parameters.

Alternatively or additionally to any of the embodiments above, the method may further include receiving a selection to adjust a threshold value of the one or more thresholds.

Alternatively or additionally to any of the embodiments above, the method may further include providing a notification if a value of the one or more patient parameters exceeds a threshold.

Alternatively or additionally to any of the embodiments above, the method may further include receiving an image of a brain of the patient and display the image.

Alternatively or additionally to any of the embodiments above, the method may further include instructing the user interface to display the image of the brain of the patient adjacent to the trend lines of the one or more patient parameters.

Alternatively or additionally to any of the embodiments above, the method may further include identifying portions of the image associated with the values of the one or more patient parameters, and instructing the user interface to highlight the portions of the image associated with the values of the one or more patient parameters.

Alternatively or additionally to any of the embodiments above, the method may further include determining the values of the one or more patient parameters from image data of the image.

Alternatively or additionally to any of the embodiments above, the method may further include instructing the user interface to display an indication on the trend lines of the one or more patient parameters, the indication indicates when an image of a brain of the patient was taken and/or is to be taken.

Alternatively or additionally to any of the embodiments above, the method may further include instructing the user interface to display an indication along a timeline common to the trend lines of the values of the one or more patient parameters, the indication indicates when an image of a brain of the patient was taken and/or is to be taken.

Alternatively or additionally to any of the embodiments above the method may further comprise receiving a first image of a brain of the patient and a second image of the brain of the patient and displaying the first image and the second image.

Alternatively or additionally to any of the embodiments above the method may further comprise synchronously navigating slices of the first image of the brain and the second image of the brain.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
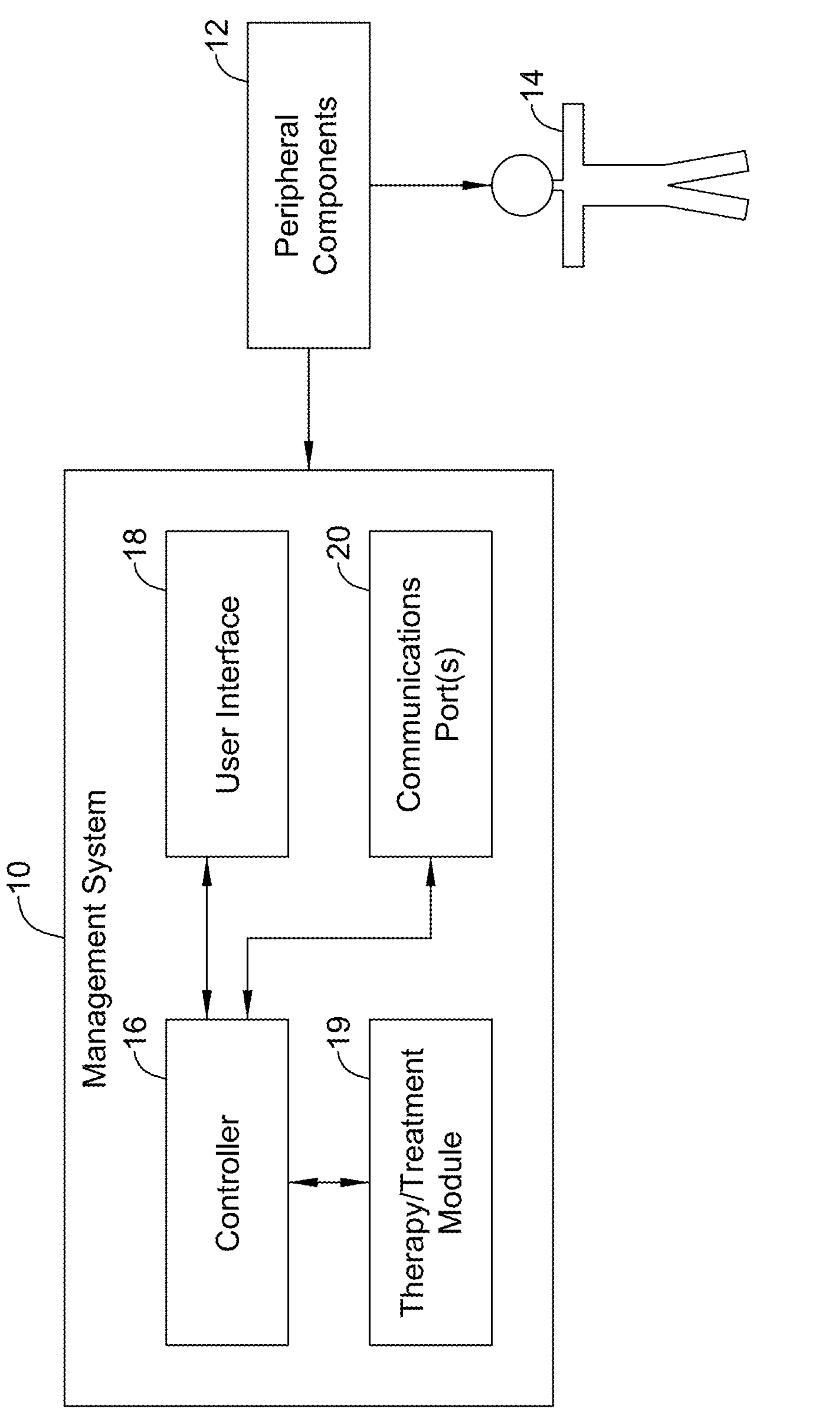
FIG. 1 is a schematic depiction of an example patient management system in communication with a patient.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAIL DESCRIPTION

The incidence of stroke worldwide is approximately 15 million per year. Strokes may be ischemic or hemorrhagic. Hemorrhagic strokes, including intracranial hemorrhages like subarachnoid hemorrhage (SAH) or intracerebral hemorrhage (ICH), account for approximately 15% of all strokes. Common poor outcomes in the domain of hemorrhagic stroke include vasospasm, delayed cerebral ischemia, and delayed ischemic neurologic deficit, hydrocephalus, and disability or death, amongst others. Strokes and other acute brain injuries (e.g., caused by trauma, hemorrhage, stroke, etc.) are often treated in the neurosurgical and neurocritical care environment. Acute brain injuries may occur in various degrees and may require that the brain go through a healing process and/or one or more surgical interventions.

Between one-quarter and more than one-half of patients admitted to the neurological intensive care unit (NICU) for acute brain injury develop a fever. The cause of fever in these patients often remains unexplained. Central fever related to loss of the physiological regulation of body temperature by the hypothalamus is often proposed as a possible cause for persistent fever in patients with acute brain injuries that have no evidence of infection. As hyperthermia is strongly detrimental for the recovery of an acutely injured brain and contributes to an increase in the length of stay in the NICU, techniques to monitor and restore body temperature to a normal "operating" temperature (e.g., ~98.6 degrees Fahrenheit (F)) play an important role in minimizing inflammation and restoring healing to an injured brain.

Status epilepticus (SE), a condition in which epileptic seizures follow one another without recovery of consciousness between the seizures, affects up to 150,000 patients each year in the United States, with a mortality between 3% and 33%. Initial treatment of SE with drugs (e.g., benzodiazepines, phenytoin, and/or phenobarbital) typically fails to terminate SE in 30%-50% of SE cases. The lack of curing SE after treatment with drugs may be particularly problematic because cases of longer duration become more difficult to treat. Even infusions of anesthetics (e.g., doses of midazolam, pentobarbital, and propofol) that are traditionally used to control refractory SE, fail in 8%-21% of cases. Furthermore, seizures, particularly prolonged seizures or seizure episodes, pose a risk of permanent neuronal damage. Given the incomplete efficacy of current therapies and the potential for neurologic damage, improved diagnoses, earlier treatments, and active monitoring are need to treat and reduce brain injuries in patient that have SE.

Effective cerebral oxygenation requires an adequate cerebral perfusion pressure and patients suffering an acute brain injury and/or other conditions may be susceptible to inadequate cerebral perfusion pressures. Cerebral perfusion pressure may depend upon the 'resistance' offered by intracranial pressure (ICP) or jugular venous pressure (JVP), whichever is higher. Intracranial pressure is determined by the relative proportion of soft tissue, blood, and CSF within the cranium. In healthy, supine adults normal ICP is 5-15 mmHg, becoming sub-atmospheric on standing (around-10 mmHg). Sustained elevations in ICP have been shown to adversely affect patient outcomes and as such, intracranial hypertension (i.e., elevated ICP) provides a modifiable risk factor in the management of patients with an acute brain injury or other head injuries. In most cases, relatively conservative methods such as head elevation, sedation, and/or osmotherapy are sufficient for treating lower ICP. In over 50,000 cases annually, however, ICP remains elevated despite the use of these conservative treatment methods and thus, needs to be monitored and/or managed.

A patient with an injured brain may deal with fever, seizures, swelling, and/or high intracranial pressure. As discussed below, medical providers and other medical professionals receive data from many tools and/or resources concerning a patient's brain injury, however, the resources and/or information from the resources are decentralized and are at disparate locations, such that it is labor-intensive to obtain and draw insights from the entirety of the data when time is of the essence. That is, medical providers and other medical professionals have limited tools at their disposal to assist in gathering captured data and assessing the data from the various resources when providing neurocritical care of patients (e.g., the diagnosing, treating, managing, and healing of brain injuries).

The disclosed concepts may provide management systems that may, or may be used to, diagnose, administer therapy for, predict outcomes for, facilitate decision making around, monitor, and/or manage a condition of a patient in a manner configured to improve outcomes for the patient with acute brain injury. Further, the management system may be configured to, or may be configured to facilitate, an early diagnosis of a condition related to an acute brain injury or other head condition and/or manage the condition related to the acute brain injury or other head condition over time. To facilitate early diagnoses of patient conditions, the management system may include an automated image (e.g., computerized tomography scan (CT scan), magnetic resonance imaging (MRI) images, angiography images, etc.) analyses system that processes images, identifies parameter boundaries or areas (e.g., locations such as geometric points, lines, areas, and/or volumes) in the images, and/or presents data associated with the parameter boundaries using unique user interface features. In some cases, the management system may include one or more treatment component configured to treat and/or diagnose a patient, but this is not necessarily required.

Turning to the Figures, FIG. 1 schematically depicts a management system 10 in communication with a patient 14. The management system 10 may include or may be configured to connect to one or more peripheral components 12 that are configured to be used in conjunction with the patient 14. The management system 10 may be configured to connect to the one or more peripheral components 12 via a physical connection and/or a communication connection (e.g., a network). The management system 10 may reside entirely within one or more remote servers and may be accessible on computing devices via one or more networks, but this is not required.

The peripheral components 12 may include components used and/or configured to facilitate determining diagnoses of, applying therapy and/or treatments to, predicting outcomes for, decision making around, and/or monitoring and managing one or more conditions of the patient 14 using the management system 10. Example peripheral components 12 include, but are not limited to, catheters, sensors, electrical connectors, mechanical connectors, surgical navigation systems, wired networks, wireless networks, imaging components, imaging scanners, monitoring components, remote servers, and/or other suitable components configured to facilitate determining a diagnoses of the patient 14, applying a therapy and/or a treatment to the patient 14, and/or monitoring and managing the patient 14 over time using the management system 10.

Example catheters that may be used with the management system 10 are described in U.S. patent application Ser. No. 16/152,382 filed on Oct. 4, 2018, and titled "SYSTEMS, CATHETERS, AND METHODS FOR TREATING ALONG THE CENTRAL NERVOUS SYSTEM", which is hereby incorporated by reference for all purposes. Other suitable catheters are contemplated.

The management system 10 may include a controller 16, a user interface 18, one or more communications ports 20, and/or software components. The management system 10 may be or may include physical systems and/or software components stored on a computer readable medium (e.g., a physical component) for execution by a processor. The management system 10 may be, may include, or may be in communication with a remote server accessible over one or more networks. Further, the management system 10 may be, may include, or may be in communication with a medical system usable by medical providers at a medical facility. In some cases, the management system 10 may be accessible entirely via a network.

Figure 2:
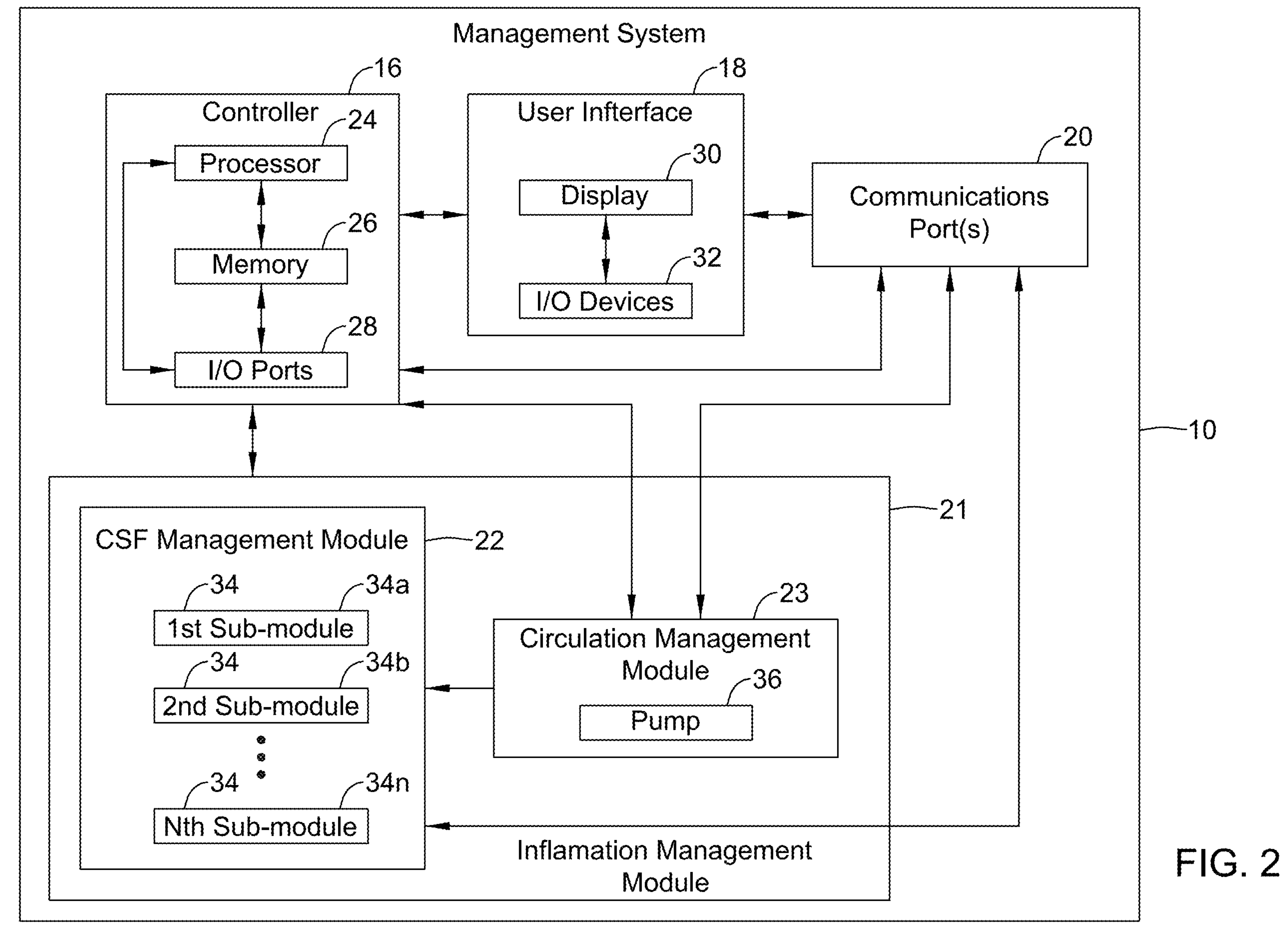
FIG. 2 is a schematic block diagram of an example patient management system.

The management system 10 may have or may be in communication with one or more therapy and/or treatment components, which may or may not be considered a peripheral component 12. Although not required, the management system 10 may have and/or may be in communication with a therapy and/or treatment module 19 (e.g., an inflammation management component 21, as depicted in FIG. 2, a surgical navigation module, etc.) and/or one or more other components suitable for use in operation of the management system 10. In some cases, although the therapy and/or treatment module 19 may be separate from the controller 16, part of or an entirety of the therapy and/or treatment module 19 may be incorporated into the controller 16.

One or more of the components of or in communication with the management system 10 may be configured to communicate directly with one another. Alternatively, one or more of the components of the management system 10 may be configured to communicate with another component through the controller 16. For example, measurements and/or data from the peripheral components 12 may be received via the communications port(s) 20 and may be provided to the controller 16 and/or stored by the controller 16. The controller 16 then may process the data to monitor, manage, and/or diagnose the patient, display the data and/or measurements on the user interface 18, and/or initiate and/or perform a treatment protocol.

Further, the controller 16 may interact with the user interface 18 to provide, in an automated manner, measurements and/or other relevant data to users for managing and/or monitoring one or more conditions of the patient 14. In one example, the controller 16 may obtain data related to one or more monitored patient parameters (e.g., monitored via peripheral components and/or monitored using one or more other suitable components), where the monitored patient parameters may contribute to or otherwise relate to a brain condition of the patient. In some cases, the controller 16 may the instruct the user interface 18 to display (e.g., graphically display) values of the one or more monitored patient parameters in trend lines over time. The user interface 18 may be or include a physical display device and/or may be or include a screen for display on a physical display device.

FIG. 2 schematically depicts illustrative components of or usable with the management system 10. As discussed above with respect to FIG. 1, the management system 10 may include, among other components, the controller 16, the user interface 18, and the communications ports 20. The management system 10 may include and/or may be usable with a therapy and/or treatment module, such as the inflammation management module 21. The inflammation management module 21 may include the CSF management module 22, the circulation management module 23, and/or other suitable components.

The controller 16 may include one or more components. In one example, the controller 16 may include one or more processors 24, memory 26 in communication with the processor 24, input/output (I/O) ports 28 in communication with the processor 24 and/or the memory 26, and/or one or more other suitable components. Some or all of the components of the controller may reside within one or more housings. In some cases, the memory 26 may be or may include non-transitory computer readable medium that may include or may be programmed to include software and/or other instructions to be executed by the processor 24 and facilitate the controller 16 operating in an automated manner to produce a user interface configured to facilitate monitoring and/or managing a patient condition, such as an acute brain injury or other suitable condition, and/or to output control signals via the I/O ports 28 (e.g., to the user interface 18, to the inflammation management module 21, to other components of the management system 10, and/or to other components usable with the management system 10) based on input received at the I/O ports 28, the user interface 18, and/or communications ports 20 communicating with peripheral components 12. Additionally or alternatively, the controller 16 may be configured to output control signals to the peripheral components 12 via the user interface 18, the communications ports 20, and/or other suitable components.

The processor 24 may include a single processor or more than one processor working individually or with one another. Example processor components may include, but are not limited to microprocessors, microcontrollers, multi-core processors, graphical processing units, and/or other suitable processor components.

The memory 26 may include a single memory component or more than one memory component working individually or with one another. Example types of memory may include RAM, ROM, EEPROM, FLASH, other volatile or non-volatile memory, or other suitable memory for the controller 16.

The I/O ports 28 may be any type of communication port configured to communicate with, via a wired and/or wireless network, the inflammation management module 21, the user interface 18, the communications ports 20, and/or one or more other components of or usable with the management system 10. Example I/O port types may include wired ports, wireless ports, radio frequency (RF) ports, Bluetooth ports, Near-Field Communication (NFC) ports, HDMI ports, Ethernet ports, VGA ports, serial ports, parallel ports, component video ports, S-video ports, composite audio/video ports, DVI ports, USB ports, optical ports, and/or other suitable ports. Although the I/O ports 28 are depicted as part of the controller 16 and separate from the communications port(s) 20, in additional and/or alternative instances, the I/O ports 28 may be at least part of the communications port(s) 20 and/or may be separate from the controller 16.

The user interface 18 may be any suitable type of user interface configured to facilitate a user interacting with the management system 10. For example, the user interface 18 may include a display 30, input/output (I/O) devices 32, screens as graphical user interfaces for display on a display (e.g., the display 30 and/or other suitable displays), and/or other suitable user interface components configured to facilitate a user interacting with the management system 10. The display 30 may include a touch screen and/or may be an LED, LCD, OLED or other display type. The I/O devices 32 may include and/or may be incorporated in or with one or more of a work station, a computer, a computing device, a tablet computer, a phone, a keypad, a display, a touch screen, a touch pad, a mouse, a speaker, a microphone, and/or one or more other suitable components that facilitate a user interacting with the management system 10. Illustrative screens of the user interface 18 are discussed below.

The display 30 may include any suitable display configuration (e.g., see FIGS. 4-24) to facilitate displaying information relating to a patient for which the management system 10 is being used to monitor, manage, and/or treat. In some cases, screens depicted on the display 30 may include one or more panes or portions (e.g., where each pane or portion may or may not be separated by visible boundaries). In one example, the display 30 may include a first pane for displaying one or more medical images of the patient (e.g., an MRI, a CT scan, an x-ray, and/or other suitable medical image of the patient), a second pane and/or a third pane adjacent to the first pane that displays measurements of, or values related to measurements of (e.g., which may be measurements of, values derived from one or more measurements of, values derived from one or more measurements over time of (e.g., heart rate variability, etc.), etc.), and/or indicators related to measurements of or a status of one or more parameters (e.g., physiological parameters, anatomical parameters, demographic parameters and/or other suitable parameters) of the patient that are obtained from one or more components of one or more medical or non-medical systems (e.g., patient goals, medications for the patient, comorbidities, age, sex, name, days in intensive-care-unit (ICU), intracranial hemorrhage (ICH) volume, total ventricular volume, ventricular CSF, intraventricular hemorrhage (IVH), brain inflammation, white blood cell count (WBC), blood glucose, body temperature (TMP), heart rate, heart rate variability (HRV), respiratory rate, photoplethysmography (PPG), mass effect on a brain, mid-line shift (MLS) from a CT scan, blood volume (VOL), edema volume (PHE), intracranial pressure (ICP), water in the brain, brain tissue compliance (CMP), National Institute of Health Stroke Scale (NIHSS), level of consciousness (LOC), eye measurements with a pupilometer, motor skills (MTR), sensations (SNS), language skills (LNG), fluid management, blood pressure (BP), diastolic BP, systolic BP, fluid input and output (I/O), cerebral perfusion pressure (CPP), sodium content (Na++), potassium content (K++), Charlson Comorbidity Index, injury size, an index of parameters (e.g., inflammation index, Glasgow Coma Scale (GCS) index, NIHSS index, mass effect index, a worsening index (e.g., the NEUROWORSENING™ index and/or other suitable worsening indices), and/or other suitable indices), and/or other suitable parameters).

The panes of the screens may be updated in real time in response to incoming data and/or measurements as the data and/or measurements are received and/or updated at specified or predetermined intervals. For example, trend lines and/or timelines in one or more of the panes may be updated in real time as data related to monitored parameters is received and processed by the controller 16 and/or other suitable controllers, as a user interacts with the screen, and/or in one or more other suitable instances.

The controller 16 may be configured to receive inputs to edit what is displayed on the display 30, edit a configuration of screens on the display 30, edit received data related to monitored parameters and/or what is measured from the received data, edit thresholds and/or goals related to the received data, edit actions to be taken in response to the received data, and/or receive inputs for taking action and/or edit one or more other features of the control or management system. In one example, portions of or an entirety of one or more of the panes (e.g., of the first pane, the second pane, the third pane, etc.) may be selectable and if selected, a pane with greater detail, additional detail, and/or alternative detail may be displayed on the display 30, a date range of the selected pane may be adjusted, data and/or information in another pane may be adjusted and/or modified, and/or the controller 16 may cause one or more other suitable changes to what is being displayed on the display 30 and/or how a treatment is being applied.

The display 30 may include a header (e.g., as discussed in greater detail below). The header may be a pane with selectable options for selection to move between different displays and/or may provide other suitable features and/or information.

The communications ports 20 may be separate from and/or part of other I/O ports (e.g., the I/O ports 28 and/or other suitable I/O ports) of the management system 10. The communications ports 20 may be one or more suitable types of communications ports configured to facilitate communication between the management system 10 and one or more other components configured to interact with the management system 10 (e.g., peripheral components 12, remote dataset with patient images, remote database with electronic medical records (EMR), etc.). In one example, the communications ports 20 may be configured to connect to peripheral components 12 (e.g., to receive fluid from a patient and/or to receive measurements and/or data of one or more physiological parameters of a patient that may be monitored by the controller 16 where the measurements and/or data are received from sensors), connect to scanning equipment, connect to treatment components, connect to remote databases, and/or connect to other components of and/or in communication with the management system 10.

In some instances, the communications ports 20 may be or may include mechanical communications ports and/or electrical communications ports. Example mechanical communications ports may include, but are not limited to, connection ports configured to facilitate a mechanical connection between the management system 10 and the peripheral components 12 and/or other suitable components. Such mechanical communications ports may be configured to facilitate fluid being passed to and/or from the CSF management module 22 and/or facilitate electrical signals being passed to and/or from the management system 10. Example electrical communications ports may be or may include wired ports, wireless ports, radio frequency (RF) ports, Bluetooth ports, Near-Field Communication (NFC) ports, HDMI ports, Ethernet ports, VGA ports, serial ports, parallel ports, component video ports, S-video ports, composite audio/video ports, DVI ports, USB ports, optical ports, and/or other suitable ports. In some cases, electrical communications ports may include a mechanical connection feature.

Although not required, the management system 10 may include and/or be in communication with the inflammation management module 21. The inflammation management module 21 may include one or more components configured to manage a patient's inflammation. Although other management systems 10 are contemplated, example management systems 10 including components of an inflammation management module (e.g., a management system with one or more components of an inflammation management module may be an inflammation management system) are disclosed in U.S. patent application Ser. No. 16/536,239 filed on Aug. 8, 2019, and titled "SYSTEMS, CATHETERS, AND METHODS FOR TREATING ALONG THE CENTRAL NERVOUS SYSTEM", which is hereby incorporated by reference for all purposes, and U.S. patent application Ser. No. 16/536,267 filed on Aug. 8, 2019, and titled "SYSTEMS, CATHETERS, AND METHODS FOR TREATING ALONG THE CENTRAL NERVOUS SYSTEM", which is hereby incorporated by reference for all purposes. The example inflammation management module 21 depicted in FIG. 2 includes the CSF management module 22 and the circulation management module 23.

In some cases, the CSF management module 22 may include one or more hardware and/or software sub-modules 34. In one example, the CSF management module 22 may include a first sub-module 34*a*, a second sub-module 34*b*, and a Nth sub-module 34N, where there are N sub-modules. The hardware and/or software sub-modules 34 may be swappable or exchangeable to fit different needs, as desired. For example, in one instance, a pump, a filtration treatment module and a waste control mechanism may be utilized for inflammation management; in another instance, a pump and a cooling treatment module may be utilized for inflammation management; and in a further instance, a pump, a filtration treatment module, and a cooling treatment module may be utilized. Other combinations of hardware and/or software sub-modules 34 may form or may be part of the CSF management module 22.

The circulation management module 23 may include one or more hardware and/or software modules (e.g., stored in memory for execution by the controller 16 and/or a processor of the circulation management module 23) and may be configured to control circulation of CSF through the inflammation management module 21 taking into account protocols of the CSF management module 22 and other circulation requirements. In one example, the circulation management module 23 may be configured to maintain a predetermined CSF flow rate and/or a CSF pressure at or below a set point level and/or within a range of pressure levels. The circulation management module 23 may include a pump 36, but this is not required as the circulation management module 23 may rely on other pumps of the inflammation management module 21 to pump fluid through the inflammation management module 21 according to a circulation protocol taking into account needs of the CSF management module 22.

In operation, the controller 16 of the management system 10 may interact with a controller of the CSF management module 22 and/or individual controllers of the hardware and/or software sub-modules 34 to effect operation of one or more diagnoses and/or treatment protocols in response to data processing by the controller and/or in response to user input. In some cases, the controller 16 may be configured to interact with the hardware and/or software sub-modules 34 to facilitate control and/or operation of functionality that may be common to a plurality of protocols utilizing the hardware and/or software sub-modules 34. Common functionality that may be controlled and/or performed by the controller 16 may include, but is not limited to, real-time and trended pressure measurements and recordings, total volume circulated and time elapsed circulation measurements and recordings, circulation control (e.g., via pressure limiting to prevent pressure from exceeding a set point, maintaining a constant or predetermined flow to deliver circulation at a specified flow rate, etc.), alarm management, communications, system status updating, and/or other common functionality that may be required during operation of the one or more hardware and/or software sub-modules 34. In one example, the controller 16 may be configured to control and/or manage circulation (e.g., by sending control signals to a pump, a waste control mechanism, and/or other hardware and/or software sub-module 34) during diagnoses and/or treatment protocols utilizing the hardware and/or software sub-modules 34 (e.g., controlling and/or managing fluid circulation and/or pressure monitoring in a control loop).

Figure 3:
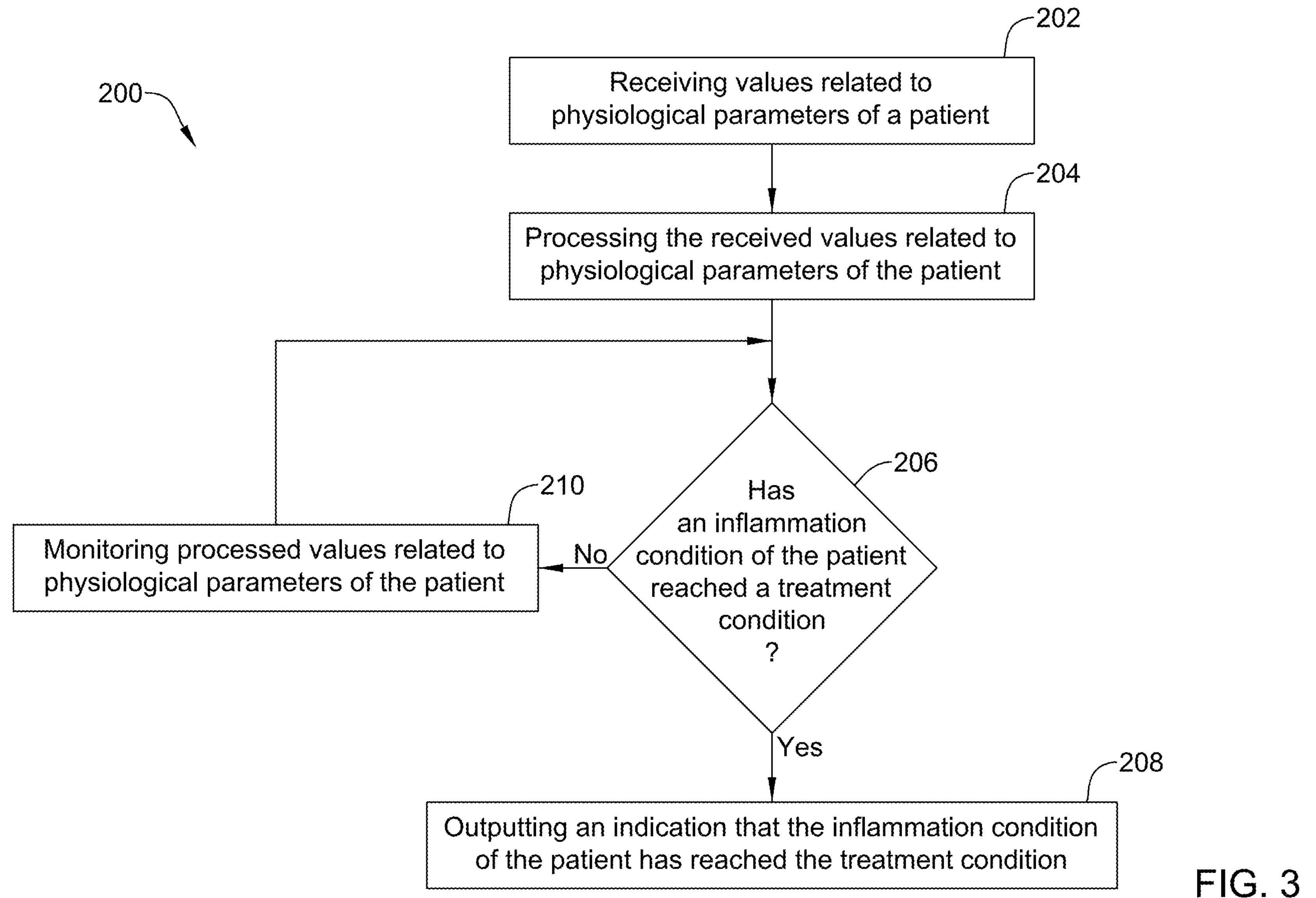
FIG. 3 is a schematic flow diagram of a method for using a patient management system with a patient.

As discussed herein, the management system 10 may be used in methods of monitoring and/or managing conditions associated with a patient's brain. FIG. 3 depicts an illustrative method 200 of managing a patient's condition. Instructions for executing the method 200 may be stored in memory (e.g., the memory 26 or other suitable memory) for execution by a processor (e.g., the processor 24, a processor of a module or sub-module of the management system 10, and/or other suitable processor). In some cases, the method 200 may be performed entirely or at least partially with a management system (e.g., the management system 10 or other suitable management system).

As depicted in FIG. 3, the method 200 may include receiving 202 (e.g., obtaining) one or more values related to parameters (e.g., physiological parameters, anatomical parameters, demographic parameters, etc.) of a patient over time. The one or more values related to parameters of the patient may be an image of the patient (e.g., image of a brain of the patient), a sensed or calculated (e.g., calculated from the image(s) of the patient, calculated from one or more sensed values, calculated from one or more sensed values over time, etc.) measurement of a patient parameter, information related to patient parameter information or data from a patient EMR, and/or other suitable data or information related to a parameter of the patient. In one example, a plurality of images of a patient that are taken over time may be received and/or measurements of sensed patient data may be received over time, which may coincide with times before, during, and/or after when the images of the patient were taken.

The data and/or information related to one or more parameters of the patient may be received and/or otherwise obtained from a component of the management system, a component from and/or associated with a different management system, a peripheral component of or associated with the management system, one or more sensors sensing a parameter of the patient, an image capturing device (e.g., a camera, a CT scanning machine, angiography machine, a MRI machine, X-ray machine, etc.), and/or other suitable data capturing devices configured to obtain and/or communicate data and/or information related to one or more parameters of the patient. Once received or otherwise obtained, the values, data, and/or information related to parameters of the patient may be stored or saved in the memory for access by a processor. The values, data, and information received and/or stored or saved in the memory may relate to a single parameter of the patient or two or more parameters of the patient.

In some cases, the data and/or information related to parameters of the patient may be received at the processor for processing from one or more input ports and/or from the memory. In one example of processing the data and/or information related to parameters of the patient, the processor may be configured to identify one or more locations in the image associated with one or more monitored patient parameters and based on the identified locations, identify and/or determine values of the one or more monitored parameters. In some cases, the processing of the images performed by the processor may utilize a computer vision algorithm. Such data and/or information related to parameters of the patient may be displayed in or on a screen as discussed in greater detail below.

Sensors, image scanners, databases, input devices, and/or other suitable devices in or otherwise connected to or in communication with the management system 10 may provide monitored measurements and/or information related to the physiological, anatomical, and/or demographic parameters of the patient. Example measurements of physiological and/or anatomical parameters that may be monitored include, but are not limited to, measurements of or related to intracranial hemorrhage (ICH) volume, subarachnoid hemorrhage (SAH) volume, total ventricular volume, ventricular CSF, intraventricular hemorrhage (IVH), brain inflammation, white blood cell count (WBC), blood glucose, body temperature (TMP), brain temperature, heart rate, heart rate variability (HRV), respiratory rate, photoplethysmography (PPG), mass effect on a brain, midline shift (MLS) from a CT scan, blood volume (VOL), edema volume (PHE), intracranial pressure (ICP), water in the brain, brain tissue compliance (CMP), National Institute of Health Stroke Scale (NIHSS), level of consciousness (LOC), eye measurements with a pupilometer, motor skills (MTR), sensations (SNS), language skills (LNG), fluid management, blood pressure (BP), diastolic BP, systolic BP, fluid input and output (I/O), cerebral perfusion pressure (CPP), sodium content (Na++), potassium content (K++), Charlson Comorbidity Index, injury size, an index of parameters (e.g., inflammation index, Glasgow Coma Scale (GCS) index, NIHSS index, mass effect index, a worsening index, and/or other suitable indices), and/or other suitable parameters) and/or measurements related to other suitable physiological and/or anatomical parameters. Additional and/or alternative information that may be provided may include information related to neurosurgical interventions of the patient, labs of the patient, medications administered or to be administered to the patient, electronic medical record information, etc.

Information related to patient demographic information or data may be obtained in any suitable manner. For example, information or data related to patient demographic information may be automatically obtained from a patient medical record, may be manually entered into memory of the system, may be obtained from one or more other management systems, may be obtained from a remote server (e.g., a remote database), and/or obtained in one or more other suitable manners.

As information related to parameters of the patient are obtained, such information stored in the memory may be processed 204. The information related to parameters of the patient may be processed using the processor of the management system and/or other suitable processor(s). The information related to parameters of the patient may be used by the management system to derive values related to parameters of the patient.

In some cases, the information related to parameters of the patient may be processed into one or more indexed values (e.g., the indexed values may be based on the values related to the physiological, anatomical, and/or demographic parameters of the patient), which may be indicative of a medical condition of the patient at a current time, indicative of how the condition has changed overtime, and/or indicative of how the condition is expected to change over a future time period. In some cases, the indexed value may be based, at least in part, on a value or values related to one (e.g., a single) physiological or anatomical parameter. Alternatively, the indexed value may be based, at least in part, on values related to two or more physiological and/or anatomical parameters.

Example indices and/or indexed values indicative of an inflammation condition or other medical condition of the patient are disclosed in U.S. patent application Ser. No. 16/536,239 filed on Aug. 8, 2019, and U.S. patent application Ser. No. 16/536,267 filed on Aug. 8, 2019, which were incorporated by reference, above, for all purposes. Further, an example index or index value that may be calculated or determined by the management system 10 may be a patient's ICH Score, which may take into account a patient's GCS, age, ICH volume, IVH presence, and an anatomic location of hemorrhage. The ICH score is discussed in greater detail in Hemphill III, J. C., Bonovich, D. C., Besmertis, L. Manley, G. T., Johnston, S. C., April 2001, The ICH Score, American Heart Association, Volume 32, Issue 4, pages 891-897, which is hereby incorporated by reference for all purposes. When the management system 10 is configured to determine a patient's ICH score, the GCS and age of the patient may be obtained from the patient's EMR and ICH, IVH, and an anatomic location of the patient's hemorrhage may be determined by analysis of received images of the patient's brain (e.g., via a computer vision algorithm trained to identify ICH, IVH, and an anatomic location of a hemorrhage. Other indices taking into account values of various received and/or calculated parameter data are contemplated.

The medical condition of the patient may be or may be related to a traumatic brain injury, a subarachnoid hemorrhage, intracranial hemorrhage, cranial tumors, intracranial aneurysm, and/or other patient condition causing inflammation in, around, and/or affecting a brain of a patient and the condition may be a level of that inflammation. Typically, such patient conditions may be difficult to assess, monitor, and/or manage and time may be of the essence. Use of the processed data and parameters of the patient, as discussed herein, may help medical providers understand the condition of the patient, determine treatment protocols that are likely to lead to successful outcomes, and/or assess the success of treatment protocols in a manner not previously contemplated.

In some cases, information of and/or related to the parameters of the patient (e.g., one or more monitored patient parameters) may be depicted or otherwise displayed on a user interface (e.g., the user interface 18 and/or other suitable user interface). Information (e.g., data, etc.) of and/or related to the parameters of the patient may be obtained by a controller (e.g., the controller 16 and/or other suitable controller) and the controller or a processor thereof may instruct a user interface (e.g., the user interface 18, a user interface of a mobile computing device, the user interface of a laptop, the user interface of a tablet, the user interface of a medical device, and/or other suitable user interface) to display values of the parameters of the patient. In some cases, the values of the one or more parameters of the patient may be displayed in trend lines, in numerical form, highlighted in an image, and/or displayed in one or more other suitable manners.

Figure 4:
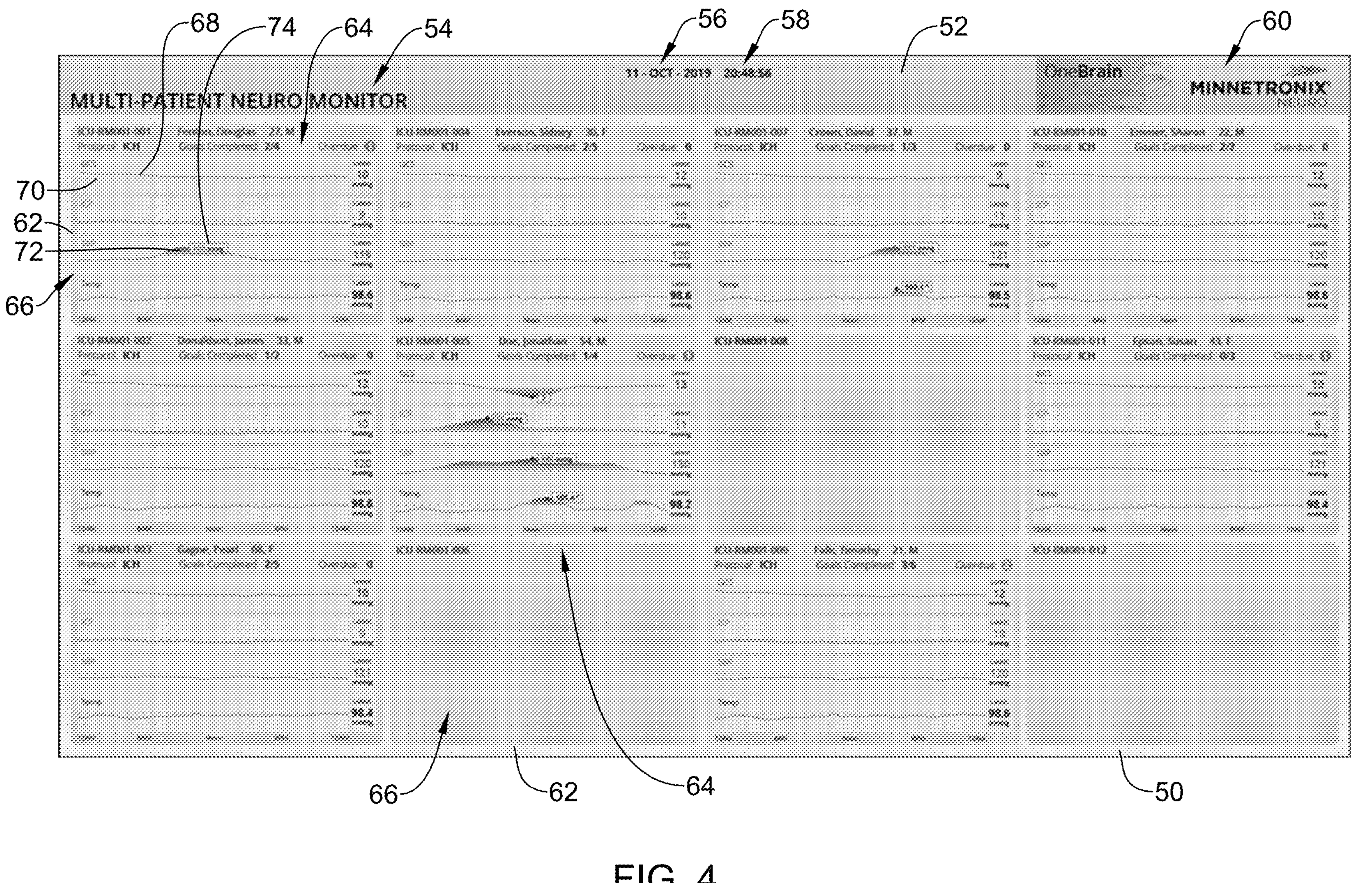
FIG. 4 is a schematic example patient overview screen for display on a user interface.
Figure 61:
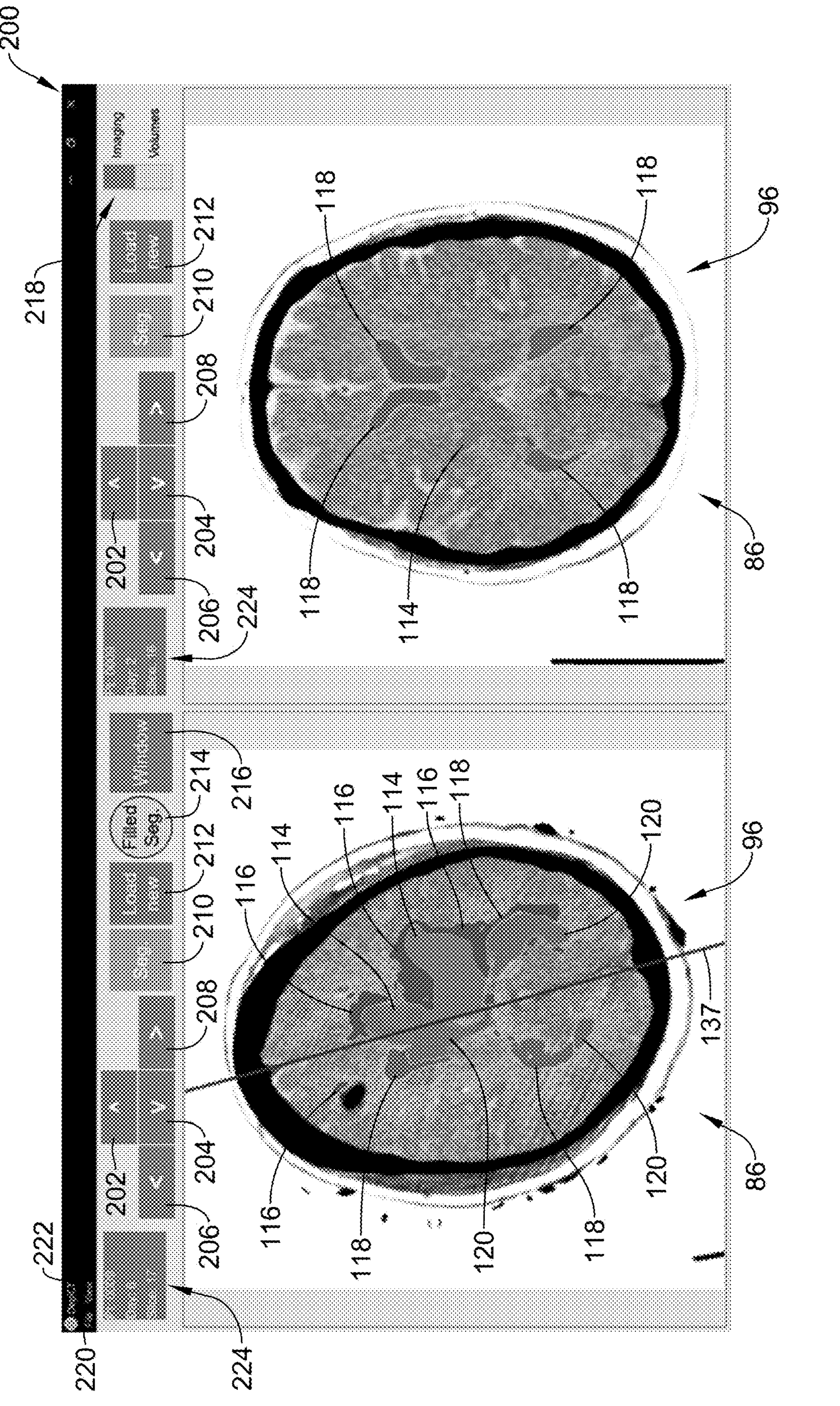

The information of and/or related to the parameters of the patient may be depicted on the user interface in a header, in one or more panes, with graphs of values versus time, with directional indicators indicating whether the respective value is increasing, decreasing, or not changing from a previous time, with ranges where the current value is shown relative to a possible range of values, with goals, within bounds, in or along a timeline, and/or depicted in one or more other suitable manners. Although other screens are contemplated, example screens of the user interface are depicted in FIGS. 4-61. Displaying values of and/or related to physiological and/or anatomical information of the patient in close proximity to one another and/or in close proximity to other information (e.g., patient images, patient demographic information, etc.) facilitates providing a medical provider with a context for values of the one or more parameters of the patient that the medical provider ordinarily would not have as such information is typically provided to the medical provider, if at all, via multiple machines and/or printouts making it difficult to understand a context of any piece of parameter information relative to the patient's condition. Further, the display configuration may facilitate a user understanding patient conditions in a relatively short amount of time (e.g., in a glance).

Based, at least in part, on the processed values related to one or more physiological parameters of the patient, the method 200 may include determining 206 whether a condition of the patient has reached a predetermined condition, such as a treatment condition, intervention condition and/or other suitable condition. In one instance, determining 206 whether a condition of the patient has reached the treatment condition or intervention condition may be based, at least in part, on one or more values determined during the processing 204 of the values of and/or related to the one or more physiological, demographic, and/or anatomical parameters of the patient.

A treatment condition or intervention condition of the patient may be a level of the condition of the patient at which a treatment or intervention should be implemented and/or may be indicative of when a treatment or intervention should occur in the future. Similar to the determined general condition of the patient, determining when the patient reaches the treatment condition or the intervention condition may be difficult to assess or define and use of the processed parameters of the patient and associated thresholds or ranges may facilitate determining when the condition of the patient has reached or will reach the treatment condition or intervention condition.

In one example technique, processed values related to one or more physiological and/or anatomical parameters of the patient may result in a value indicative of the patient's condition (e.g., an indexed value or other value indicative of the patient's condition) and when the value indicative of the patient's condition reaches a threshold value (e.g., a predetermined value, a trend level over time, a value based, at least in part, on one or more algorithms (e.g., a learning algorithm or other suitable algorithm) that use data from a plurality management systems or a global treatment protocol database, and/or other suitable threshold), it may be determined that the patient's condition has reached a treatment condition or will reach a treatment condition at a specifiable time in the future. In some cases, different determinations concerning a condition relative to a treatment condition may be made based on a value indicative of the patient's condition reaching different thresholds (e.g., different threshold levels) and/or based on a difference between the value and the threshold.

In some cases, a value of a threshold may be based, at least in part, on an algorithm that uses data from a plurality of management systems. Such data may be stored in a global database storing data from past implementations of treatment protocols from a plurality of local and/or remote management systems (e.g., such data may have information concerning, among other information, what treatment protocol was delivered for a patient condition, demographic information of the patient, when a treatment protocol was performed relative to an inflammation condition, what the values of any relevant indices were at the time of implementing or deciding to implement the treatment protocol, what the values of any relevant physiological parameters of the patient were at the time of implementing or deciding to implement the treatment protocol, etc.)

When it has been determined that the condition of the patient has reached a treatment condition based on the processed values related to the parameters of the patient, an indication that the condition of the patient has reached the treatment condition may be outputted 208. In some cases, the indication that the condition of the patient has reached the treatment condition may be outputted from the processor of the management system or other suitable processor via one or more ports in communication with the processor (e.g., the I/O ports 28, the communications ports 20, and/or other suitable port(s)). The outputting 208 of the indication may be performed automatically in response to identifying the condition of the patient has reached the treatment condition, but this is not required in all instances.

The outputted 208 indication that the condition of the patient has reached the treatment condition may be or may include any suitable indication. Example suitable indications include, but are not limited to, a control signal to a treatment module to initiate a treatment protocol, a control signal from the processor to a CSF management module (e.g., a control signal to one or more sub-modules 34 of the CSF management module 22 or other suitable components of a treatment module) to perform a treatment protocol on CSF of the patient for addressing the patient's condition, a control signal to a user interface (e.g., the user interface 18, a display 30 of the user interface, a display (e.g., the display 30 or other suitable display) on a mobile computing device, and/or other suitable user interface) to display a suggested treatment protocol for treatment of the patient's condition, a control signal to the user interface to display a value on the display of the user interface (e.g., a value of an index or other suitable value on a pane, such as the first pane or other suitable pane, of the display), a control signal configured to turn on and/or off a light (e.g., a light of the user interface or other suitable light), a control signal configured to turn on and/or off a sound (e.g., from a speaker of the user interface or other suitable speaker), a control signal initiating an appointment invite or other suitable scheduling mechanism to schedule a medical provider to initiate or perform a treatment (e.g., a predetermined treatment and/or other suitable treatment) at a time in the future, a control signal initiating an alert sent to or at a user's computing device (e.g., where the alert is at an application on a computing device, in a text message, in an email message, etc.), and/or one or more other suitable indications.

The treatment protocol may be a set of instructions or list of treatments for treating the patient's condition. Example treatment protocols may include, but are not limited to, establishing and/or adjusting patient goals, actuation of a treatment module, initiation of a surgical treatment protocol, etc.

When a treatment protocol is identified, suggested, or obtained, the processor may automatically select the treatment protocol based, at least in part, on processed values related to the parameters, a threshold reached, and/or a difference between the processed values and a threshold. Such treatment protocols may be automatically identified or selected by the processor from a database of treatment protocols associated in a predetermined manner with the various patient conditions and values of the processed values related to parameters of the patient. Alternatively or in addition, treatment protocols may be automatically identified or selected by the processor from the database of treatment protocols associated with the various patient conditions and values of the processed values related to patient parameters based on one or more algorithms (e.g., a learning algorithm or other suitable algorithm).

The treatment protocol database may be populated in any suitable manner. In one example, the treatment protocol database may be a global database storing data from past implementations of treatment protocols from a plurality of remote management systems and/or patients (e.g., such data may have information concerning, among other information, what treatment protocol was delivered for a patient condition, demographic information of the patient, when a treatment protocol was performed relative to an inflammation condition, what values of any relevant indices were at the time of implementing or deciding to implement the treatment protocol, what values of any relevant physiological parameters of the patient were at the time of implementing or deciding to implement the treatment protocol, etc.) that is usable by the one or more algorithms to determine associations between treatment protocols and the various patient conditions and processed values of the values related to the parameters of the patient that may be relevant to the patient's condition.

When it has been determined that the condition of the patient has not reached a treatment condition based on the processed values related to physiological, anatomical, and/or demographic parameters of the patient, the processed values related to parameters of the patient may be monitored 210 and the determining 206 of whether a condition of the patient has reached a treatment condition may be determined at a future time. In some cases, the steps 202-206 and 210 of the method 200 may be repeated and continuously performed at least until it has been determined the condition of the patient has reached the treatment condition. This, however, is not required. In some cases, the one or more steps of the method 200 may be repeated at predetermined time intervals and/or in response to manual actuation via the user interface or other suitable user interaction with the management system.

In a typical decision-making scenario, a medical provider may need to decide if a, when a, and/or what treatment protocol (e.g., a surgical intervention) should be initiated and makes the decision based on data received (e.g., data identifying the patient's status, risk profile, and potential outcomes), where the more personalized the information the more useful it is for deciding when to treat a patient. However, the medical provider may be inundated with information and/or data related to the patient's condition and potential outcomes of various treatment protocols from various resources and thus, the flood of data available may actually hinder the medical provider's decision-making process. As such, coupling treatment protocols (e.g., interventions) with improved decision support, as discussed herein, will lead to better patient outcomes.

Neurocritical care is one of the most data-intensive areas of the healthcare system. Utilization of the data related to neurocritical care, however, has been limited due to a lack of aggregating and/or cross-referencing relevant data in the industry in a manner that can be processed by a medical provider in a time sensitive scenario. For example, although CT scans of a patient may have been taken, a patient's medical history may be known, patient parameters may be sensed, data concerning results of other patients with similar conditions may be known, etc., there have been resource, technology and privacy challenges preventing or limiting medical providers from fully utilizing all available information when making care decisions in a time sensitive scenario. Furthermore, data concerning results of other patients, particularly outside of a given institution, has been limited to retrospective of prospective clinical trials and thus may only be applicable to patients that meet the criteria of those trials. This data may then be used to potentially determine guidelines, however, it can be difficult for medical providers to compare outcomes from the clinical trial to the patient at hand if the patient criteria differs from the criteria used for the clinical trials.

In another example, a disconnect between image acquisition and other relevant parameter data at and/or around the time of acquiring a patient image may result in limited analysis of a patient's condition. Illustratively, though a medical provider may receive an ICH volume and a midline shift indication when receiving a radiology report associated with a CT scan, there is no time alignment to other patient parameters, the report gives no context as to whether noted parameter values are increasing or decreasing over time, and often the report is completed well after the CT exam is performed, further decoupling the interpretation from the current clinical situation. Moreover, the radiology report does not typically have values for other parameters that may be identifiable from a CT scan including, but not limited to, an edema volume, a ventricular CSF volume, an IVH volume, etc. Thus, a full quantitative examination of the progression of a patient's status on CT imagery is not the standard of care.

The management system 10 may facilitate receiving, processing, organizing, and presenting information from one or more sources concerning one or more patients and/or one or more patient conditions. The user interface 18 and screens displayed thereon may facilitate a user's (e.g., a medical provider's, such as a surgeon's, intensivists', nurses', administrator's, a family's, etc.) understanding of the data in a manner not otherwise available to the user that facilitates decision making in time sensitive scenarios. In some cases, the user interface 18 may be configured to display one or more screens that facilitate the user identifying the patient's status, risk profile, and potential outcomes. Further, the user interface may facilitate the user understanding whether one or more treatment protocols will be, are, and/or were effective. A user may be able to view sequential images of a patient's brain and parameter values associated with the brain images and/or taken around the time the image was taken on one screen. In one example beneficial use of the management system, a user may be able to view sequential brain images of a patient and associated data prior to and post EVD implant clamping and if the ventricles increase in size post-clamping relative to prior to clamping, the user may be able to indicate with certainty that the patient has hydrocephalus and may need a shut. In another example beneficial use of the management system 10, a user may be able to view sequential brain images of a patient and associated data prior to and post evacuation of the ICH hematoma, enabling the user to evaluate the effectiveness of the evacuation as well as the volume of the remaining blood.

Screens of the user interface 18 of the management system 10 may be configured to aggregate patient-related data in a manner configured to facilitate making medical decisions and/or treatment determinations. In one example, the screens of the user interface 18 may aggregate data from patient images (e.g., the images, data extracted from digital images, etc.), past, current (e.g., real-time), and/or future (e.g., predicted trajectories) vitals and/or other sensed or calculated parameters of the patient, past, current, and potential future interventions performed and/or initiated on the patient, electronic medical record (EMR) data, and/or other suitable data.

FIGS. 4-61 depict various illustrative screens that are configured for display on the display 30 of the user interface 18 to facilitate a user's understanding of patient related data in order to improve decision making around a patient condition and assess treatment protocols. A controller (e.g., the controller 16 and/or other suitable controller) may be programmed to process data for display on the UI, to cause the user interface to display one or more of the illustrative displays, and/or receive interactions with the screens and/or displays. In some cases, the screens may be customizable to allow users to configure the screens in a manner that facilitates their personal understanding of the available data.

The controller 16 or other suitable controller may obtain data related to one or more monitored patient parameters (e.g., patient parameters related to a brain condition of the patient and/or other suitable patient parameters) and instruct or otherwise cause the user interface 18 and/or other suitable user interface to display values of the one or more monitored patient parameters. The controller may cause the values and/or indications of values to be displayed on an image of the patient's brain, in trend lines, in numerical representations, etc.

The screens are configured to facilitate a user's understanding of a patient's condition over time throughout care for the patient. In one instance, the screens may be configured to display data identifying the patient's status, goals, risk profile, and/or potential outcomes for an individual patient. Based, at least in part, on the displayed data, a medical provider may formulate a recommended treatment protocol. During the planning and implementation of the recommended treatment protocol and/or a management system suggested treatment protocol, the screens may provide context-sensitive data related to potential outcomes of the treatment protocol applied to the individual patient. Further, the screens may automatically asses and/or provide data facilitating the medical provider to assess the effectiveness of the applied treatment protocol, including if and/or when a patient condition deteriorates during a treatment protocol.

FIG. 4 depicts a patient overview screen 50 (e.g., a multi-patient monitor, as depicted in the example of FIG. 4). The patient overview screen 50 may provide an overview of all or some beds, patients, etc. associated with the management system 10.

The patient overview screen 50 may have a heading portion 52 (e.g., a heading bar, as depicted in FIG. 4, and/or other suitable configuration). The heading portion 52 may include, among other additional and/or alternative information, a screen title (e.g., MULTI-PATIENT NEURO MONITOR, etc.) 54, a date 56, a time 58, product name section 60, etc. Other screens may have the heading portion 52 providing similar and/or dissimilar sections and/or information.

The patient overview screen 50 may include one or more patient overview panes 62 (only some of the patient over view panes 62 are provided with reference numerals). In one example, the patient overview screen 50 may display patient overview panes 62 for patients and/or beds in a facility or unit of a facility. As depicted in FIG. 4, the patient overview panes 62 are organized by available bed in an intensive care unit (ICU) of a hospital, but the patient overview panes 62 may be organized in one or more other suitable manners. For example, each of the patient overview panes 62 is provided with a location heading 64, which at a minimum may provide a location in a facility or unit of a facility (e.g., ICU-RM001-001, ICU-RM001-006, etc.).

The patient overview panes 62 that are populated with patient information may be associated with beds of the ICU that are occupied with a patient, whereas the patient overview panes 62 that are not populated with patient information may be associated with empty beds of the ICU. Although patient overview panes 62 that are populated with patient information and that are not populated are displayed in the patient overview screen 50 of FIG. 4, this is not required and only patient overview panes 62 that are populated with patient information may be displayed.

In addition to or as alternative to providing a location of a bed or patient, the location heading 64 may provide other data related to the bed or patient associated with the patient overview pane. For example, patient identifying information (e.g., patient name, age, sex, etc.), patient-specific treatment protocol, goals status information, overdue actions indicator, etc. may be provided in the location heading 64.

The patient overview panes 62 may include a parameter portion 66. The parameter portion 66 may provide data related to one or more patient parameters (e.g., anatomical parameter, physiological parameter, demographic parameter, etc.). Although other data may be displayed (e.g., as selected by a user, such as a medical provider and/or other suitable user) in the parameter portion 66, data related to the GCS, ICP, SBP, and temperature (TEMP) (e.g., body temperature) of the patient may be displayed. The parameter portion 66 may be empty or blank when a patient is not associated with the bed or location of the patient overview pane 62.

In some cases, as depicted in FIG. 4, the data in the parameter portion 66 may be displayed over time and a timeline may be provided. One or more timelines may be provided. In some cases, a single timeline may be provided that is common to two or more trend lines of parameter data (e.g., of monitored patient parameters) and may be located below the parameter data, though other locations of the timeline(s) are contemplated.

Generally, the parameter portion 66 of the patient overview panes 62 may include parameter data relevant to a user understanding a current condition of the patient. Even so, any suitable data related to a parameter of the patient may be displayed in the parameter portion 66.

As depicted in FIG. 4, each parameter displayed in the parameter pane or portion 66 may include data over time (e.g., with data values on the y-axis and time on the x-axis), a trend line 68 of the parameter data over time, a parameter goal or threshold line 70 (e.g., as represented by a dashed line) indicating a threshold value, and a current or latest reading of the parameter. In some cases, positioning a current or latest reading of a sensed parameter at an end of the parameter data over time may facilitate a user quickly reviewing the patient overview pane 62 and determining how a patient's current condition compares to the patient's condition over time and relative to a parameter goal, whereas the user would otherwise need to review a chart and/or multiple screens to obtain this information and analysis of the information obtained via charts or multiple screens may be perceived as being burdensome to the extent that the analysis does not occur as frequently as is needed for best-practices care of the patient.

The controller 16 of the management system 10 may be configured to automatically take an action in response to a value of monitored data related to the patient exceeding the threshold value (e.g., a threshold value that may be represented by the threshold line 70). In one example, the controller 16 may be configured to provide a notification, initiate a treatment protocol, display a particular screen, and/or take other suitable actions if the value of monitored data reaches or goes beyond (e.g., exceeds) a threshold value. Example notifications and/or actions, may include, but are not limited to, highlighting the trend line 68 on the display (e.g., highlighting an entirety of the trend line 68 and/or a portion of the trend line 68), highlighting deviations of parameter data from the parameter goal or threshold line 70, sounding an alarm, providing a notification on the patient overview screen 50, outputting a notification to a remote computing device (e.g., a mobile or other computing device of a user, a central monitoring computing device, a central database, etc.), outputting a control signal to cause a treatment protocol to be effected, establish a recommend treatment protocol based on the parameter exceeding the threshold, schedule a treatment protocol, and/or one or more other suitable notifications and/or actions.

Further, as the parameter portion 66 may highlight parameter deviations from the parameter goal or threshold line 70. In one example, the parameter portion 66 may highlight parameter deviations from the parameter goal or threshold line 70 by color coding a space 72 between the parameter trend line 68 and the parameter goal or threshold 70 with different colors as a size of the space increases and/or decreases. Alternatively or additionally, the color of the trend line 68, the thickness of the trend line 68, and/or other suitable highlighting of data may occur to highlight parameter deviations from the parameter goal or threshold line 70. The color coding may be determined by comparing parameter data and/or a difference between parameter data and a goal to one or more thresholds and/or may be determined in one or more other suitable manners. Although not required, a peak value 74 (e.g., 160 mmHg for the SBP of the patient, as depicted in FIG. 4) of the parameter data may be noted along the trend line 68 on the patient overview pane 62.

Figure 5:
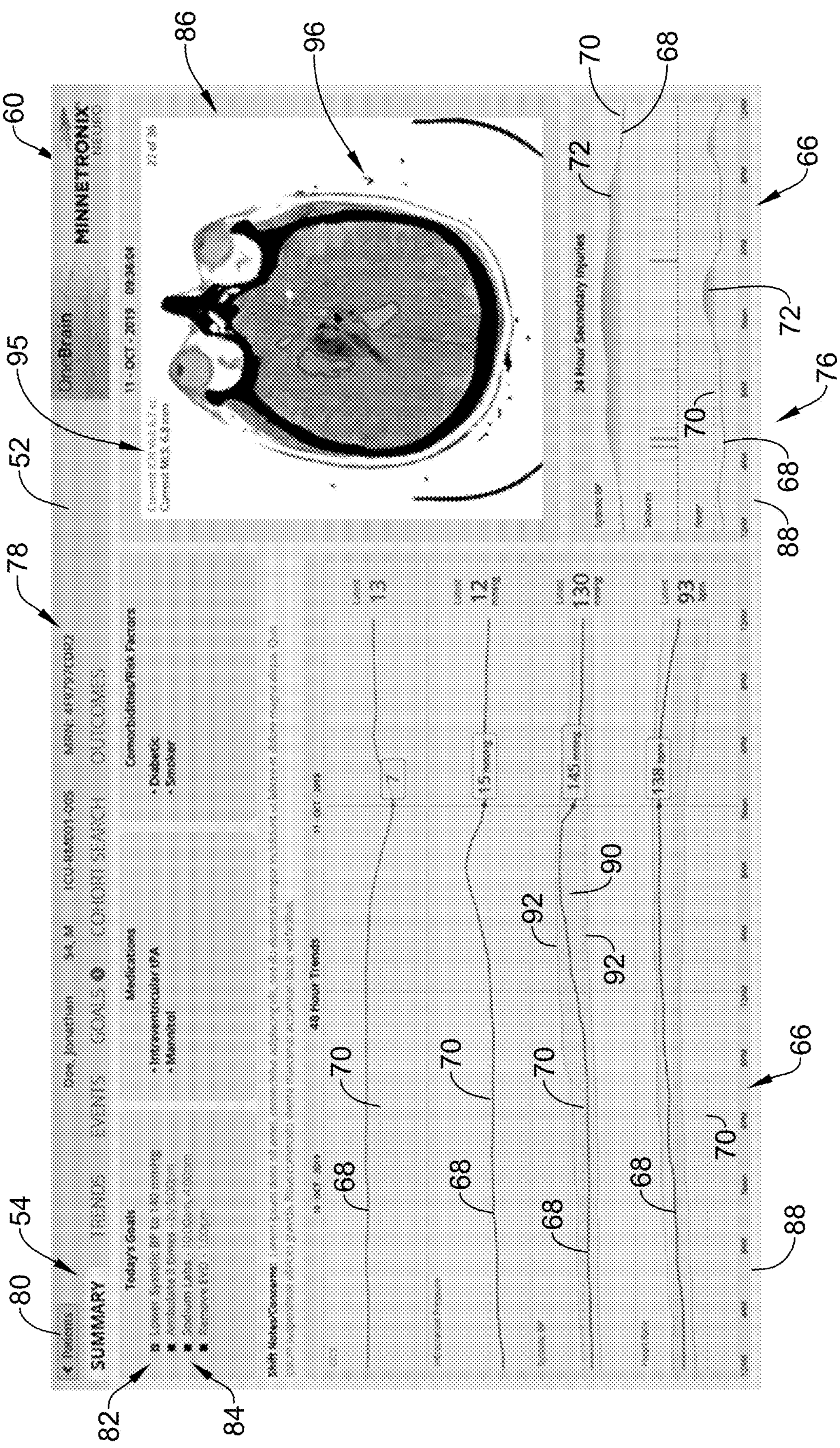
FIG. 5 is a schematic example patient condition screen for display on a user interface.

In some cases, the patient overview pane 62 may be selected (e.g., by clicking on the desired patient over view pane 62 and/or selecting in one or more other suitable manners) to display patient condition screen 76, such as the patient condition screen 76 displayed in FIG. 5. As depicted in FIG. 5, the patient condition screen 76 may include the heading portion 52.

The heading portion 52 may include any suitable information and/or selectable buttons. As depicted in FIG. 5, the heading portion 52 may include the screen title 54 (e.g., a highlighted one of screen options, which may include SUMMARY, TRENDS, EVENTS, GOALS, COHORT SEARCH, OUTCOMES, etc.), the date 56, the time 58, the product name section 60, patient identifying information 78 (e.g., patient name, age, sex, location, medical record number (MRN), etc.), one or more selectable buttons 80 (e.g., a back button or other suitable indicated button (e.g., labeled "Patients", as in FIG. 5) selectable to go to a previous page), and/or one or more other suitable pieces of information and/or selectable buttons.

In some cases, one or more of the screen titles 54 may be selectable to go to a sub-screen associated with the selected title. Selecting a screen title 54 labeled SUMMARY, may cause a sub-screen providing a summary of data related to a selected patient to be displayed. Selecting a screen title 54 labeled TRENDS may cause a sub-screen providing data over time and related to the selected patient to be displayed. Selecting a screen title 54 labeled EVENTS may cause a sub-screen providing data related to events (e.g., surgical events, medical events, imaging events, medication events, etc.) involving the selected patient to be displayed. Selecting a screen title 54 labeled GOALS may cause a sub-screen providing goals associated with the selected patient and/ providing an opportunity for a user to set goals for the selected patient to be displayed. Selecting a screen title 54 labeled COHORT SEARCH may cause a sub-screen providing data related to patients with similar conditions as the selected patient to be displayed. Selecting a screen title 54 labeled OUTCOMES may cause a sub-screen providing data related to potential outcomes for the selected patient based on a condition of the selected patient to be displayed.

One of the sub-screens may be a default sub-screen. For example, in response choosing a patient by selecting a patient overview pane 62 in the patient overview screen 50, a summary sub-screen 82 may be automatically displayed on the patient condition screen 76. In some cases, the sub-screen set as the default may be modified by a user and/or automatically selected based on data received by the controller 16.

When a screen title 54 is selected to go to an associated sub-screen, the heading portion 52 may remain the same, save for denoting (e.g., with a highlight, such as a color change and/or other suitable highlight, etc.) the selected screen, and the portions or panes below the heading portion 52 may change with the selected screen title 54. Alternatively or additionally, the heading portion 52 may change in one or more manners depending on which screen title 54 is selected.

In FIG. 5, the SUMMARY label or screen title 54 has been selected (e.g., automatically or manually) from the heading portion 52, which may cause a summary sub-screen 82 to be displayed in the patient condition screen 76. The summary sub-screen 82 may include any suitable panes or portions for providing a summary of the selected patient's conditions. The summary sub-screen 82 may include, among other suitable panes or portions, a summary portion or pane 84, an image pane or portion 86, and/or one or more patient parameter panes or portions 66 (e.g., two patient parameter panes or portions 66, as depicted in FIG. 5).

The summary portion or pane 84 of the summary sub-screen 82, as depicted in FIG. 5, may include a goals section, a medications section, a comorbidities/risk factors section, a notes section (e.g., shift notes/concerns, as depicted in FIG. 5), and/or one or more other suitable patient summary sections providing an overview or background information on the patient. In some cases, when the information in the summary portion or pane 84 is viewed in combination with the information in the other portions or panes of the summary sub-screen 82, users may be able to ascertain a context of the values of sensed data in the other portions or panes of the summary sub-screen 82. For example, a goal listed in the goals section of the summary portion or pane 84 may help provide context to a current value of one or more displayed images, displayed parameters, and/or a trend line of one or more displayed parameters, and vice versa.

As depicted in FIG. 5, two parameter panes or portions 66 are provided in the illustrative summary sub-screen 82. A first of the two parameter panes or portions 66 is titled "48 Hour Trends", which shows values of sensed or calculated data for one or more patient parameters (e.g., GCS, Intracranial Pressure, Systolic BP, and Heart Rate, as depicted in FIG. 5) along a timeline 88. As depicted in FIG. 5, the values of data may be connected by or otherwise represented by the trend line 68 and/or the goal or threshold line 70 may be provided along the timeline 88 and/or the trend line 68, but these lines are not required over the past forty-eight hours. The timeline 88, when included, may be a common timeline for multiple trendlines and/or a timeline 88 may be provided for each of two or more trend liens 68. Further, a current value of the depicted patient parameter may be provided (e.g., the current value of the depicted patient parameter may be provided at an end of the trend line 68).

In some cases, a range 90 of values of the patient parameters may be provided along the trend line 68 or the timeline 88 to show or otherwise demonstrate a variability of the represented parameter. The range 90 may have lines 92 marking the upper and lower values of parameter represented by the range 90. Although not required, the area between the lines 92 may be shaded to facilitate visually representing the range to a user and to facilitate the user quickly ascertaining the variability of the parameter. In the instance of a heart rate patient parameter, understanding the variability of the patient's heart rate may facilitate determining a condition of or changes in the patient's autonomic nervous system. Understanding the variability of other patient parameters may similarly or differently facilitate understanding the patient's condition.

The first parameter pane or portion 66 may include a line 94 representing a selected time along the timeline 88. The line 94 may extend through one or more of the trend lines 68 representing the values of the depicted parameters and a value of the respective parameter at the point the line 94 crosses the trend lines 68 may be displayed (e.g., in FIG. 5, at the location associated with the location of the line 94 the GCS has a value of 7, the intracranial pressure has a value of 15 mmHg, the systolic blood pressure has a value of 145 mmHg, and the heart rate has a value of 138 beats per minute). In some cases, the line 94 may be selected and adjusted by a user to different locations along the timeline 88 and the value at the points the line crosses the trend lines 68 may be adjusted in real time.

A second of the two parameter panes or portions 66 is titled "24 Hour Secondary Injuries", which shows values of sensed or calculated data for one or more patient parameters (e.g., Systolic BP, instances of seizures, and a patient temperature or fever, as depicted in FIG. 5) along a timeline 88 of the past twenty-four hours. As depicted in FIG. 5, the values of data may be connected by or otherwise represented by the trend line 68, the goal threshold line 70 may be provided along the timeline 88 or the trend line 68, and/or data may be represented by bars indicating occurrences of the parameter (e.g., an occurrence of a seizure), but these lines or bars are not required. Similar to as discussed above with respect to the patient overview pane 62, spaces 72 associated with parameter deviations from the parameter goal or threshold line 70 or other suitable threshold value may be highlighted. Although not required, a peak value of the parameter data may be noted along the trend line 68.

The image pane or portion 86 may depict an image 96 of the patient (e.g., a two-dimensional slice of a three-dimensional image in the instance of a CT scan and/or other suitable image) along with information identifying the image 96. The image 96 may be a two-dimensional image, a three-dimensional image, and/or other suitable type of image. In some cases, a user may be able to select the image 96 or the image pane or portion 86 to rotate, pan, tilt, and/or zoom the image.

Viewing images of slices of a CT scan may be a typical manner of viewing CT scan images. In some cases, all slices of a CT scan may be provided to or obtained/received by the management system 10 and viewable by a user. Alternatively or additionally, only a subset of the slices of a CT scan may be viewable by a user. In one example of facilitating viewing less than all of the slices of a CT scan, a thickness of each slice of a CT scan may be normalized. For example, if a CT scanner is a one (1) millimeter (mm) scanner and produces approximately 150 slices per brain scan, it may be possible to normalize a slice thickness to five (5) mm via averaging every five (5) slices, which may allow for creating a sub-set of thirty (30) CT scan slices that are viewable by a user for the original CT scan image. Other techniques may be utilized to reduce a number of images of slices from a CT scan that are viewable by a user. The management system 10 may be configured to reduce the number of images of slices of a CT scan that are viewable by a user and/or the management system 10 may be configured to receive the reduced sub-set of images of slices of the CT scan for viewing by users. Alternatively or in addition, a user may be able to manually adjust a number of images of slices of the CT scan that are viewable depending on the user's need for detail in making a patient condition determination.

The image pane or portion 86 may be configured to and/or positioned in a screen to facilitate a user interpreting data of or related to the image 96. In some cases, the image pane or portion 86 may include a parameter value portion 95 where values for one or more parameters represented in the image 96 may be located. As depicted in FIG. 5, the values of the ICH of the patient in the depicted image is 6.7 cc and the MLS of the patient in the depicted image is 6.8 mm. In some cases, the image 96 depicted in the image pane or portion 86 may be positioned adjacent trend lines 68 in the parameter portion 66 to facilitate a user's understanding of the monitored data displayed in the parameter portion 66 and/or to more precisely interpret the image 96 than is otherwise possible with only the monitored data displayed or only the image 96 displayed, as at least some of the monitored data may be obtained from and/or otherwise relate to the image 96.

The image 96 may be selected for display based on any suitable factors and may be selected automatically and/or manually. In one example, the image 96 may be automatically selected based on being a most-recent image available for display, but this is not required. When the image 96 is from a CT scan, the image of the slice depicted from the CT scan may be automatically selected (e.g., based on an image of a slice showing a largest ICH location, based on an image of a slice in which a midline shift is computed and/or displayed, such as a slice depicting the largest midline shift captured in the CT scan, and/or based on one or more other suitable factors). In some cases, the three-dimensional image of the CT scan may be separated into images of a plurality of two-dimensional slices of the scan and a number of the depicted slice displayed relative to the plurality of slices may be displayed (e.g., the image 96 in FIG. 5 is the $22^{nd}$ slice of 36 slices having images associated with the CT scan and available to be displayed).

A date and/or time may be displayed in the image pane or portion 86 that is representative of a date and/or time at which the image was taken. In some cases the line 94 of the selected time may be associated with the date and/or time at which the image 96 was taken and/or may adjust as the image changes and vice versa. Connecting the image to the line 94 may facilitate displaying information that allows a user to gain an understanding of a patient's condition over time relative to various goals from a single screen and in a timely manner.

Figure 6:
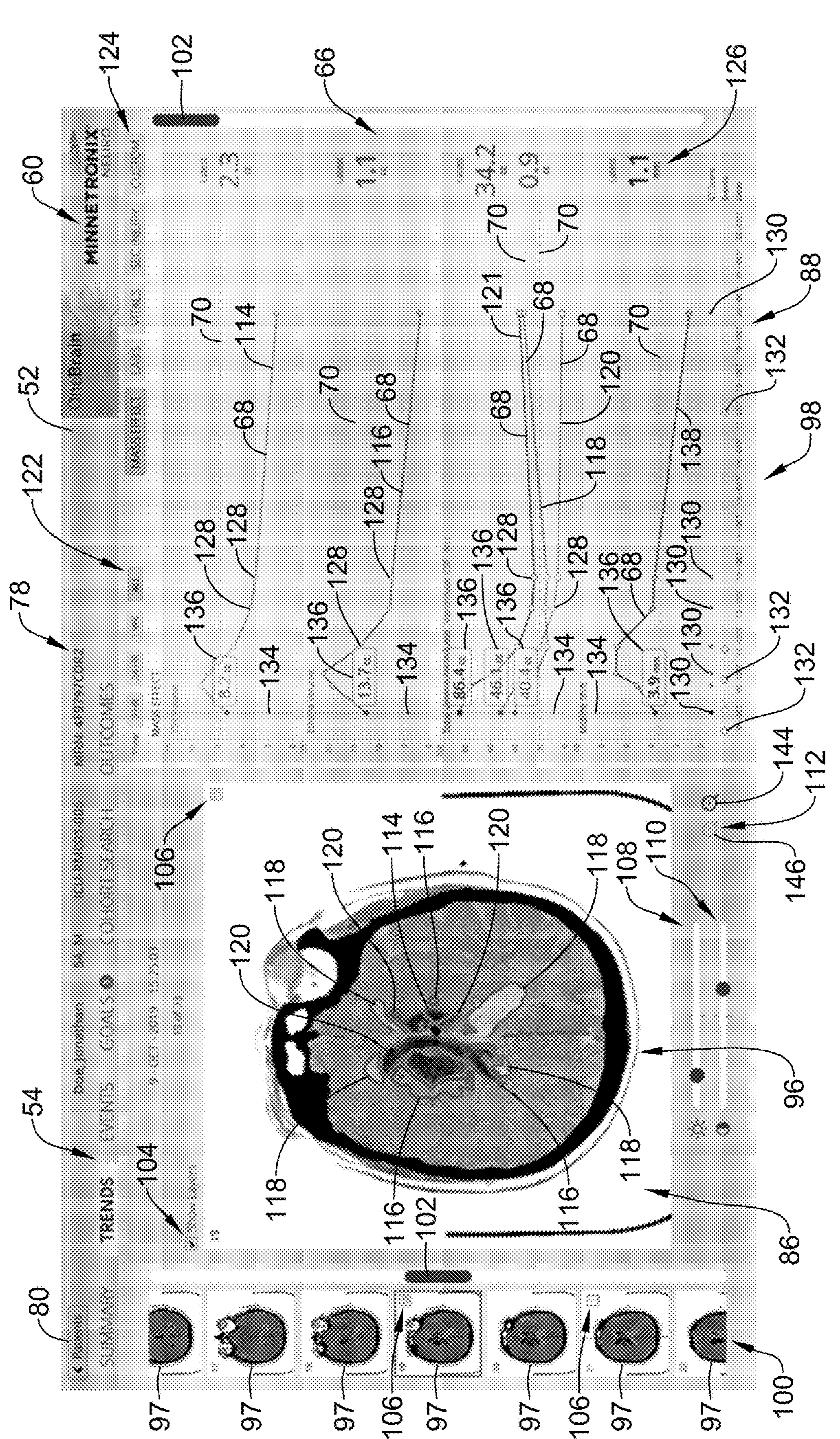
FIGS. 6-20 are schematic examples of trend sub-screens for display on a user interface and depicting information related to mass effect of a selected patient.

The summary sub-screen 82 depicted in FIG. 5 and/or other similar summary screens may be configured to provide a user a general understanding of a patient's condition. To facilitate obtaining a more in-depth understanding of the patient's condition, a user may select the screen title 54 labeled "TREND" from the heading portion or pane 52 to advance to a trend sub-screen 98, for example as depicted in FIG. 6. Alternatively or additionally, a user may select the image 96, the image pane or portion 86 and/or other patient-specific portion of the summary sub-screen 82 to move or otherwise switch to the trend sub-screen 98 and/or other sub-screen.

FIG. 6 depicts an illustrative trend sub-screen 98 depicting values related to a mass effect. The trend sub-screen 98 may include any suitable configuration of panes and/or information. In the example configuration depicted in FIG. 6, the trend sub-screen 98 may display a heading portion or pane 52, a parameter portion or pane 66, an image portion or pane 86, a selectable images portion or pane 100, and/or one or more other suitable portions or panes displaying data and/or information. As discussed in further detail below, the parameter portion or pane 66, the image portion or pane 86, and the selectable images portion or pane 100 may be interconnected such that adjustments of or user interactions with one portion or pane may affect what is displayed in another pane in a manner that is configured to allow the management system 10 to provide a user with contextual data and/or information the user would not otherwise have in one location.

The selectable images portion or pane 100 of the trend sub-screen 98 may depict a plurality of selectable images 97 of the patient. The selectable images 97 may be images of slices of CT scans of the patient, as depicted in FIG. 6, and/or other suitable medical images (e.g., MRI images, x-ray images, two-dimensional images, three-dimensional images, etc.) of the patient. Alternatively or additionally, the selectable image portion or pane 100 may include selectable images 97 taken over time. The plurality of selectable images 97 may be listed in chronological order, sequential order from a top to bottom or bottom to top when viewing two-dimensional images of slices of a three-dimensional image, a user-determined order, or other suitable logical order.

The actual selectable image 97 of the plurality of selectable images 97 may be displayed in the selectable images portion or pane 100, as depicted in FIG. 6. Alternatively or additionally, a name or title of the selectable image 97 or data file for the selectable image 97 may be displayed and selectable in the selectable images portion or pane 100.

Further, when a parameter of note has been identified in the selectable image 97 (e.g., in an automated and/or manual manner), one or more parameter indicators 106 may be provided in the selectable image 97 of the plurality of selectable images 97 of the selectable images portion or pane 100 to provide an indication of which selectable images 97 depict parameters of note relative to other selectable images 97. In one example, an image of slice "19" may have a parameter indicator 106 indicating that the selectable image 97 of slice "19" depicts the largest location representing an ICH volume of any of the images of slices of the CT scan and an image of slice "21" may have a parameter indicator 106 indicating that the selectable image 97 of slice "21" depicts the greatest midline shift of any of the images of slices of the CT scan. In some cases, the parameter indicators 106 are automatically added to the images in response to an automated or manual identification of the parameter in the selectable image 97. Alternatively or additionally, the parameter indicators 106 may be added to an image in response to a user manually noting the parameter(s) represented by the one parameter indicators 106 are of particular note in that selectable image 97.

In some cases, a scroll bar 102 may be provided to scroll through the plurality of selectable images 97. Alternatively or additionally, a user may be able to use arrow-buttons on a keyboard, arrow buttons on the screen, and/or other direction adjusting mechanisms to adjust the images viewable in the selectable images portion or pane 100 and/or to adjust which selectable image 97 of the selectable images 97 is selected.

A user may select a selectable image 97 of the plurality of selectable images 97 in the selectable images portion or pane 100 to cause the selected image 96 and/or associated data to be displayed in the image portion or pane 86. The selected image 96 of the plurality of selectable images 97 may be selected in any suitable manner. In one example, a user may click on a selectable image 97 to display the image 96 in the image portion or pane 86 and/or select the selectable image 97 in any other suitable manner.

Similar to the image portion or pane 86 discussed above with respect to FIG. 5, the image portion or pane 86 may depict an image 96 of the patient along with associated data. For example, the image portion or pane 86 may display or otherwise provide a number of the depicted image relative to the plurality of similar images 96 depicted in the selectable images portion 100 and a date and/or time representative of a date and/or time at which the selected image 96 was taken. Additionally, the image portion or pane 86 may include a selectable layers button 104 to show layers of the displayed image 96 (e.g., highlighting or other indications of areas of note in the displayed image 96), one or more parameter indicators 106 indicating parameters of note in the displayed image, a brightness adjustment area 108, a tint adjustment area 110, a zoom adjustment area 112 (e.g., having a zoom-in button 144 and a zoom-out button 146, as depicted), and/or one or more other suitable features and/or areas. The brightness adjustment area 108, the tint adjustment area 110, and the zoom adjustment area 112, and/or other suitable features and/or areas may include one or more selectable buttons or features to adjust a brightness level, a tint level, and a zoom level, etc., respectively. Although certain configurations are depicted for adjusting the brightness level, the tint level, and the zoom level, other suitable configurations are contemplated.

In some cases, the numerical values that are embedded in the imagery are representative of physical parameters (e.g. Hounsfield Units mapped from black to white in a CT scan image) and are mapped to distinct intensity values on the display. In this case, adjusting the brightness or tint in the image portion or pane 86 may be replaced and/or supplemented with the capability to window or otherwise redefine the contrast mapping curve of those physical units to display values.

The selectable layers button 104 may be selected or deselected to display and/or remove layers or indications of notable areas in the image 96. In FIG. 6, the selectable layers button 104 is selected and areas of note are highlighted with different line types representative of a type of noted area. The areas of note depicted in FIG. 6 represent an ICH volume 114, an edema volume 116, a ventricular CSF volume 118, and an IVH volume 120. Although volume (three-dimensional) parameters are identified from the images 96, the volumes are represented as noted areas (two-dimensional) in the images 96 that are representative of volumes taken at the particular slice of the CT scan in the displayed image 96. Alternatively or additionally, area parameters may be identified from and highlighted in two-dimensional images.

As depicted in FIG. 6, the areas of volumes 114, 116, 118, 120 in the image 96 may be outlined. In one example, the ICH volume 114 may be outlined with an orange line, the edema volume 116 may be outlined with a blue line, the ventricular CSF volume 118 may be outlined with a green line, and the IVH volume 120 may be outlined with a purple line. Additionally or alternatively, a line indicative of a midline shift may be identified in the displayed image 96, along with other suitable parameters.

Figure 25:
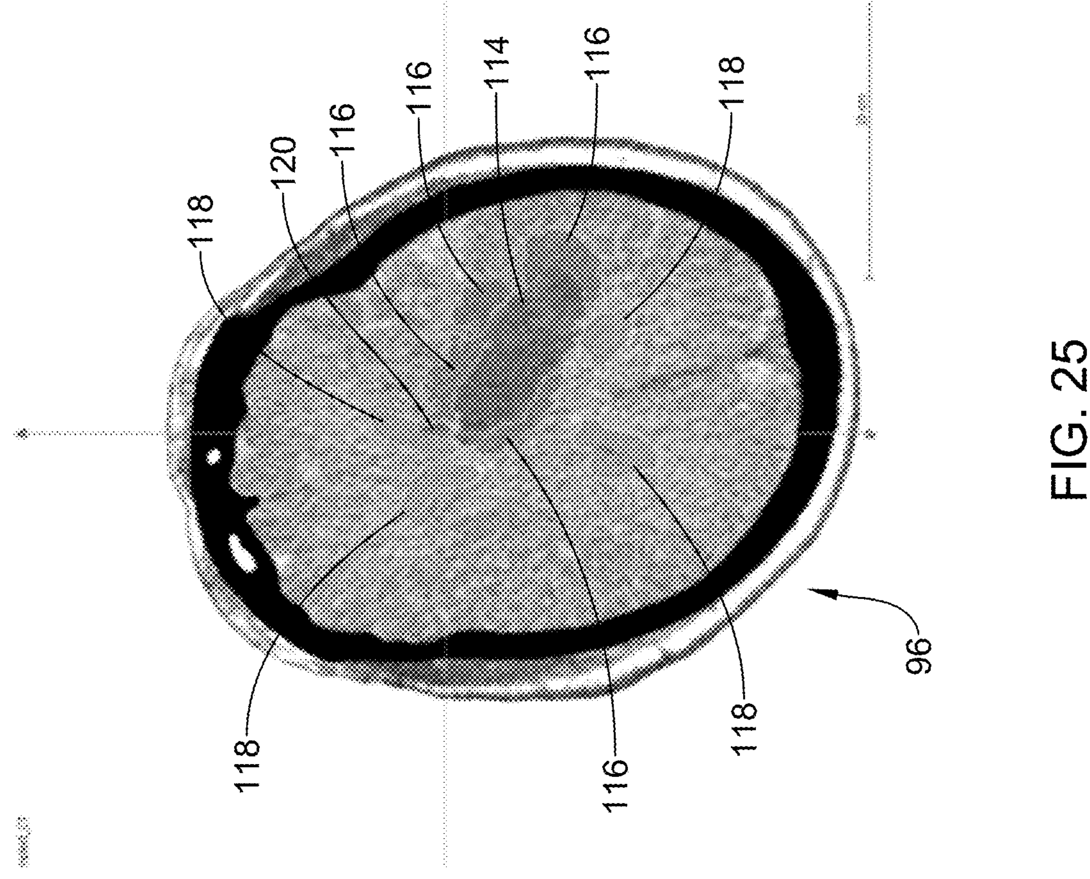
FIG. 25 is a schematic example of an image with areas of interested shaded.

In some cases, areas of note may be highlighted by modifying the area of note. For example, FIG. 25 depicts areas of different types of volumes in different shades or colors. In one instance, the area of the ICH volume 114 may be shaded or filled in with an orange color, the area of the edema volume 116 may be shaded or filled in with a blue color, the area of the ventricular CSF volume 118 may be shaded or filled in with a green color, and the area of the IVH volume 120 may be shaded or filled in with a purple color. In some cases, shading an area of note rather than outlining the area of note may save processing power. Even so, the areas of note may be outlined and shaded or filled in or identified in one or more other suitable manners.

The areas of note may be identified in any suitable manner. For example, a user may be able to review an image 96 and manually identify areas and/or features in the image 96 that are of note and then label such areas and/or features.

The areas and/or features of note may then be saved with the image 96. Alternatively or additionally, a computer vision algorithm may be applied to the data of the image 96 to identify specified areas and/or features of note. When a computer vision algorithm is used separate from or in addition to a manual identification, the computer vision algorithm may be automatically applied to all of the images 96 of the patient and/or to predetermined ones of the images 96 to identify areas of interest.

Although other computer vision algorithms are contemplated, the computer vision algorithm may include a segmentation algorithm configured to analyze CT scans. In one example, the segmentation algorithm may utilize a 3D U-Net architecture, which has previously been proven to accurately perform segmentation tasks on medical images. The 3D U-Net consists of two paths: 1) an analysis path, and 2) a synthesis path. On the analysis path, the more heavily weighted segmentation classes were amplified, thus masking unlabeled voxels, which were given weights of zero. On the synthesis path, upsampling was performed between layers to increase resolution, while connections to layers in the analysis path provided context from the amplified weighted segmentation classes.

To train the computer vision algorithm, manually segmented scans may be used. During training, a number of epochs may be performed with a weighted cross-entropy loss function before switching to a Tversky loss function for another similar number of epochs. For preprocessing, each CT scan used for training may have its spacing normalized, may have a bounding box created around the skull, and may have this box subdivided into overlapping voxel 3D patches. By dividing training CT scans into patches, the algorithm may be able to have a uniform input size and may have an increased number of training cases. Accompanying each training CT scan may be a copy of the scan with segmentation classes labeled, a file with the volumes of the labeled segmentation classes, and a file with layers and the labeled midline shift coordinates in those layers. In addition to the segmentation algorithm, an algorithm to predict the midline shift may be trained, which may also a 3D U-Net.

Prior to undergoing a segmentation prediction, CT scans may undergo the same preprocessing described above. In addition to predicting the locations of hemorrhages, ventricles, and edema, the segmentation prediction may also predict the midline shift of the scan. The outputs from the algorithm's segmentation prediction may include: 1) a resampled version of the input CT scan, 2) a segmented CT scan with the same size as the original input CT scan, 3) a segmented CT scan with the same size as the resampled input CT scan, 4) a file with the calculated volumes of each predicted segmentation class, the predicted midline shift offset, and the layer containing the predicted midline shift, 5) a file with the area of each predicted segmentation class's outline on each layer, and the layer containing the predicted midline shift, and 6) image files of each layer, the outlines or shading of each predicted hemorrhage, ventricle, and edema, and the predicted midlife shift line.

Example areas (e.g., locations) of interest include, but are not limited to, areas associated with a midline, a midline shift, an ICH volume, edema volume, ventricular CSF volume, IVH volume, anatomic hemorrhage volume, and/or other areas associated with parameters identifiable from an image. In some case, the computer vision algorithm may be trained or otherwise configured to identify relative locations of the noted areas (e.g., ventricle locations, gridline locations, locations from other noted areas, location relative to an outline of a brain, etc.).

Full quantitative examination of the progression of a patient's status on CT imagery is not the standard-of care due to the length of time it takes to manually review sequential CT images. However, utilization of the computer vision algorithm to analyze the patient brain images (e.g., to identify and/or calculate relevant anatomic and volumetric factors over time), as discussed herein, may facilitate a user quantitatively examining the progression of a patient's status using imagery (e.g. CT imagery and/or other suitable imagery) as the areas of interest are identifiable by the algorithm in an automated manner, which saves users large amounts of time over a fully manual review. Further, such quantitative examination of patient images will allow users to improve decision making around what treatment protocols to initiate and when to initiate the treatment protocols.

When one or more areas of interest have been identified, or in some cases particularly noted by a user, one or more parameter indicators 106 may be displayed in the image portion or pane 86, as discussed above. As depicted in FIG. 6, the parameter indicator 106 may indicate that image 96 is the selectable image 97 of a slice of a CT scan that includes the largest location associated with an ICH volume. Additional or alternative parameter indicators 106 representing other parameters of note may be displayed in the image portion or pane 86.

The parameter portion or pane 66 of the trend sub-screen 98 may, generally, be similar to the parameter pane 66 depicted in FIGS. 4 and 5 and/or may include additional or alternative features. The parameter portion or pane 66 may provide data related to one or more patient parameters (e.g., demographic parameters, anatomical parameters, physiological parameters, lab parameters, patient vitals, parameters related to a secondary condition, customized parameters, indexed parameters, etc.).

The parameter portion or pane 66 of the trend sub-screen 98 may have a selectable view area 122. The selectable view area 122 may allow a user to select an amount of data that may be displayed. In one example, the amount of data that is displayed may be adjusted based on a selected amount of time from which data is to be obtained (e.g., adjust a length of a chart's time window/timeline). In the example of FIG. 6, the selectable view area 122 may have selectable buttons for viewing the last three (3) hours of data, the last twenty-four (24) hours of data, the last week of data, and all of the data. Other options for selecting an amount of data may be provided. The amount of data selected in FIG. 6 is ALL data, but this selection is not required.

From a selected parameter data set, a user may be able to zoom in and/or zoom out to cause the amount of data and/or granularity of the data over time to change. In one example, zooming in on a data related to a patient's heart rate may cause a trendline and indications of a patient's heart rate variability to be displayed. In the example, zooming out on the data related to the patient's heart rate may result in the display of a current heart rate value, a minimum heart rate value, a maximum heart rate value, a heart rate variability indication, etc.

Medical providers may desire to have access to data related to one or more sets of parameters (e.g., clusters of parameter data). Example sets of parameters may be predetermined and/or customized and may be or include parameters associated a patient's vitals, ICP, mass effect, GCS, NIHSS, fluids status, secondary injury, labs, and/or other suitable sets of parameter data.

The parameter portion or pane 66 of the trend sub-screen 98 may have a selectable parameter data area 124. The selectable parameter data area 124 may allow a user to select a predetermined set of parameter data to be displayed. Example sets of parameter data to be displayed include, but are not limited to, data sets related to a patient's MASS EFFECT condition, LABS, VITALS, potential secondary injury (SEC INJURY), CUSTOM parameter set customized by a user, and/or one or more other patient-related data sets. These headings are represented as example parameter set headings in the selectable parameter data area 124 in FIG. 6. In some cases, a user may be able to add and/or change the headings for the selectable parameter data area 124 and/or select different parameters to be associated with the different parameter data sets.

As depicted in FIG. 6 and FIGS. 7-20, the patient's MASS EFFECT parameter data has been selected. When MASS EFFECT has been selected in the parameter data area 124, the parameter portion or pane 66 may display data related to volumes and/or midline shift trends based on automated and/or manual analyses of segmented CT scans. In one example, a computer vision algorithm used to identify areas of note, as discussed above, may provide data from which the controller 16 may calculate values of parameters associated with the identified noted areas.

In some cases, the data in the parameter portion 66 may be calculated from images taken over time and displayed over time and the timeline 88 may be associated therewith. One or more timelines 88 may be provided. In some cases, a single timeline 88 may be provided and may be located below the parameter data for multiple parameters, though other locations of the timeline(s) are contemplated. As ALL data has been selected for viewing from the selectable view area, the timeline 88 may span or may be adjustable to show time spanning the entire range of time associated with the captured and displayable data.

If the data over the range of the timeline does not fit on the screen, the timeline 88 may be selectably slid left and/or right to adjust the time and/or dates viewable on the screen. Additionally or alternatively, other mechanisms such as a scroll bar 102 or other suitable selectable feature for adjusting what is displayed may be utilized.

As the MASS EFFECT parameter data has been selected from the selectable parameter data area 124, parameter data related to a patient's MASS EFFECT condition may be displayed in the parameter portion or pane 66. In one example, data related to the patient's MASS EFFECT condition may include, but is not limited to, ICH volume 114, Edema volume 116, ventricular CSF volume 118, IVH volume 120, total ventricular volume 121, and midline shift 137. A scroll bar 102 or other adjustment mechanism may be provided to scroll to data not viewable on the screen due to size constraints and/or due to other reasons.

In some cases, additional or alternative data may be displayed including, but not limited to, data separated out by ventricle of the patient's brain. In such cases, indicating volume measurements by ventricle may facilitate a medical provider identifying particular locations of patient conditions and how the patient conditions are affected by a treatment. For example, understanding the IVH volume and total ventricle volume for the third and fourth ventricle of a patient's brain may assist a medical provider in identifying obstructive hydrocephalus.

As depicted in FIG. 6, each parameter displayed includes data over time, a trend line 68 of the parameter data over time, one or more parameter goal thresholds or lines 70 (e.g., as represented by a dashed line), and a current or latest reading of the parameter may be viewed in a current parameter value area 126. As discussed above, positioning a current or latest reading of a sensed parameter at an end of the parameter data over time may facilitate a user quickly reviewing the parameter portion or pane 66 and determining how a patient's current condition compares to the patient's condition over time and relative to a parameter goal.

As discussed, the data displayed may be based on and/or otherwise representative of the highlighted or noted volumes 114, 116, 118, 120 in the image 96. As such, the trend lines 68 may be graphically depicted in a manner that depicts an association with the highlighted or noted volumes 114, 116, 118, 120 in the image 96. Illustratively, the graphically depicted association may be a coding (e.g., applying a similar feature to associated items, such as color coding, line thickness coding, etc.) of the outline of areas of volumes 114, 116, 118, 120 in the image 96 with associated trend lines 68. For example, the area of the ICH volume 114 and the associated trend line 68 of the ICH volume 114 may be noted with orange lines, the area of the edema volume 116 and the associated trend line 68 of the edema volume 116 may be noted with blue lines, the area of the ventricular CSF volume 118 and the associated trend line 68 of the ventricular CSF volume 118 may be noted with green lines, and the area of the IVH volume 120 and the associated trend line 68 of the IVH volume 120 may be graphically noted with purple lines, but other associations may be utilized, as desired.

One or more indicators 128 may be provided on or along the trend line 68 (not all indicators along the trend line 68 are noted in FIG. 6). In one example, the indicators 128 may indicate when an image of the patient (e.g., an image of a brain of the patient) was or will be taken. Further, the indicators 128 may be indicative of or a display of a value of the parameter associated with the trend line 68 at the location of the indicator 128. Utilizing the one or more indicators 128 may facilitate time synchronizing data across multiple platforms, including imagery.

In FIG. 6, the indicators 128 are depicted as open circles, filled-in circles, and open stars, however, the indicators 128 may have one or more other suitable configurations. In some cases, different configurations (e.g., different shapes, sizes, colors, etc.) of the indicators 128 may indicate different occurrences along the timeline 88. In the example of FIG. 6, the open circles are representative of when a CT scan occurred and the CT scans that are not currently displayed, the filled-in circles are representative of a selected data point associated with a CT scan (e.g., the image 96 of the CT scan displayed), and the open stars are representative of a most current CT scan. FIGS. 6-12 respectively depict a trend sub-screen 98 for each of the indicators 128 (e.g., and the associated CT scan) in chronological order, originally depicted in FIG. 6.

Further, the parameter portion or pane 66 may provide an indicator 130 on or along the timeline 88 of when an image (e.g., CT scan and/or other suitable image) was or will be taken and/or an indicator 132 of when an event related to one or more of the displayed parameter data sets occurred. Illustrative events include, but are not limited to, labs that are of note, surgical procedures, medication taken/provided, last round of the medical provider, and/or other suitable notable events. The indicators 130 and/or 132 may be displayed along the timeline 88, as depicted in FIG. 6, but this is not required and the indicators 130 and/or 132 may be displayed elsewhere. Configurations of different indicators may be representative of different types of events, but this is not required. Although indicators 130 and indicators 132 are noted, only a single set of indicators may be utilized, as desired.

In some cases, a vertical line 134 or other suitable indicator may facilitate indicating which data point is being observed. In some cases, a user may select a time on the timeline 88, which may associate the vertical line 134 or other suitable indicator with a data point on one or more of the trend lines 68 at the selected time. The vertical line 134 may be specific to a parameter data set and/or extend through two or parameter data sets. In some cases, a value 136 of a parameter data point may be displayed when the vertical line 134 extends through the data point. As depicted in FIG. 6, at the time selected the value 136 of an ICH volume 114 is 8.2 cc, the value 136 of an edema volume 116 is 13.7 cc, the value 136 of a ventricular CSF volume 118 is 46.1, the value 136 of an IVH volume 120 is 40.4 cc, the value 136 of a total ventricular volume 121 is 86.4 cc, and the value 136 of a midline shift is 3.9 mm. Additionally, when the vertical line 134 lines up with an indicator 128, an associated indicator 130 of a CT scan may be highlighted (e.g., colored, filled-in, etc.) so as to be distinguishable from other indicators 130 of CT scans.

Figure 7:
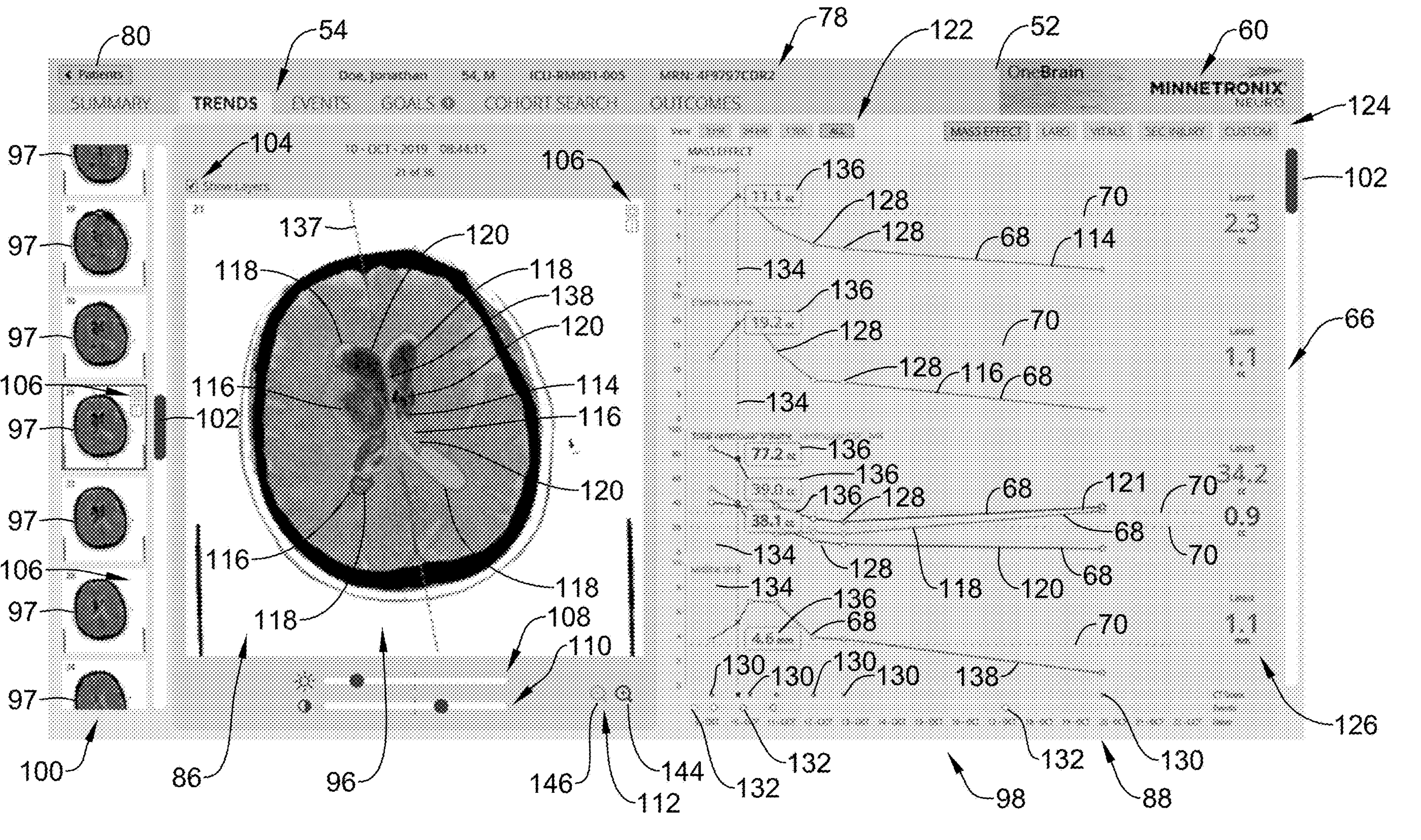

FIG. 7 depicts the trend sub-screen 98 similar to as depicted in FIG. 6, but with the image 96 taken on Oct. 10, 2019 at 08:44:15 depicted (e.g., the selectable image 97 representing slice "21" of "36" slices of the CT scan may have been selected from the selectable images portion or pane 100). The displayed image may be selected in any suitable manner. For example, a user may select the displayed image 96 by selecting an indicator 128 along the trend lines 68, an indicator 130 of a CT scan, using arrow keys on the display and/or a keyboard to switch between images, swiping the screen on a touchscreen device, and/or in any other suitable manner.

The parameter indicator 106 indicates that the depicted image 96 is the image of a slice of the CT scan that depicts the largest ICH cross-sectional area and depicts the largest midline shift. As is shown in FIG. 7, in addition to the area of the ICH volume 114 highlighted similar to as in FIG. 6, a midline 137 and a midline shift line 138 are depicted on the image 96. Although not required, an arrow 139 may be associated with the midline shift line 138 to demonstrate the direction of the midline shift. In some cases, a user may be able to manually apply the midline 137 and/or the midline shift line 138. Additionally or alternatively, when a midline shift is detected using a computer vision algorithm and/or other suitable image analyses, the midline 137 and/or the midline shift line 138 may be automatically applied to the image 96. When the midline shift line 138 has been automatically applied, a user may be able to adjust the midline shift line 138 based on its understanding of the image, but this is not required.

Similar to as in FIG. 6, the area of the ICH volume 114, the area of the edema volume 116, the area of the ventricular CSF volume 118, and the area of the IVH volume 120 in the displayed image 96 may be highlighted and/or noted. It is noted that the sizes and/or shapes of the area of the volumes 114, 116, 118, 120 depicted in the displayed image 96 of FIG. 7 differ from the sizes and/or shapes of the area of the volumes 114, 116, 118, 120 depicted in the displayed image 96 of FIG. 6, which is an image of a CT scan taken prior to the CT scan producing the image in FIG. 7. The changes in area of the volumes 114, 116, 118, 120 are also evident from changes in the values 136 noted in the parameter portion or pane 66 and graphically associated with the volumes 114, 116, 118, 120 in the image 96, where the values of the volumes at the time image 96 depicted in FIG. 7 was taken are an ICH volume 114 of 11.1 cc, an edema volume 116 of 19.2 cc, a ventricular CSF volume 118 is 39.0 cc, an IVH volume 120 of 38.1 cc, a total ventricular volume 121 of 77.2 cc, and a related midline shift is 4.6 mm. These changes may be at least partially due to the identified volumes changing in size and/or shape over time and as such, a user may be able to quickly switch between images 96 from different CT scans to view the changes in shape and/or sizes of the volumes 114, 116, 118, 120 in addition to comparing precise values presented in the parameter portion or pane 66.

Figure 8:
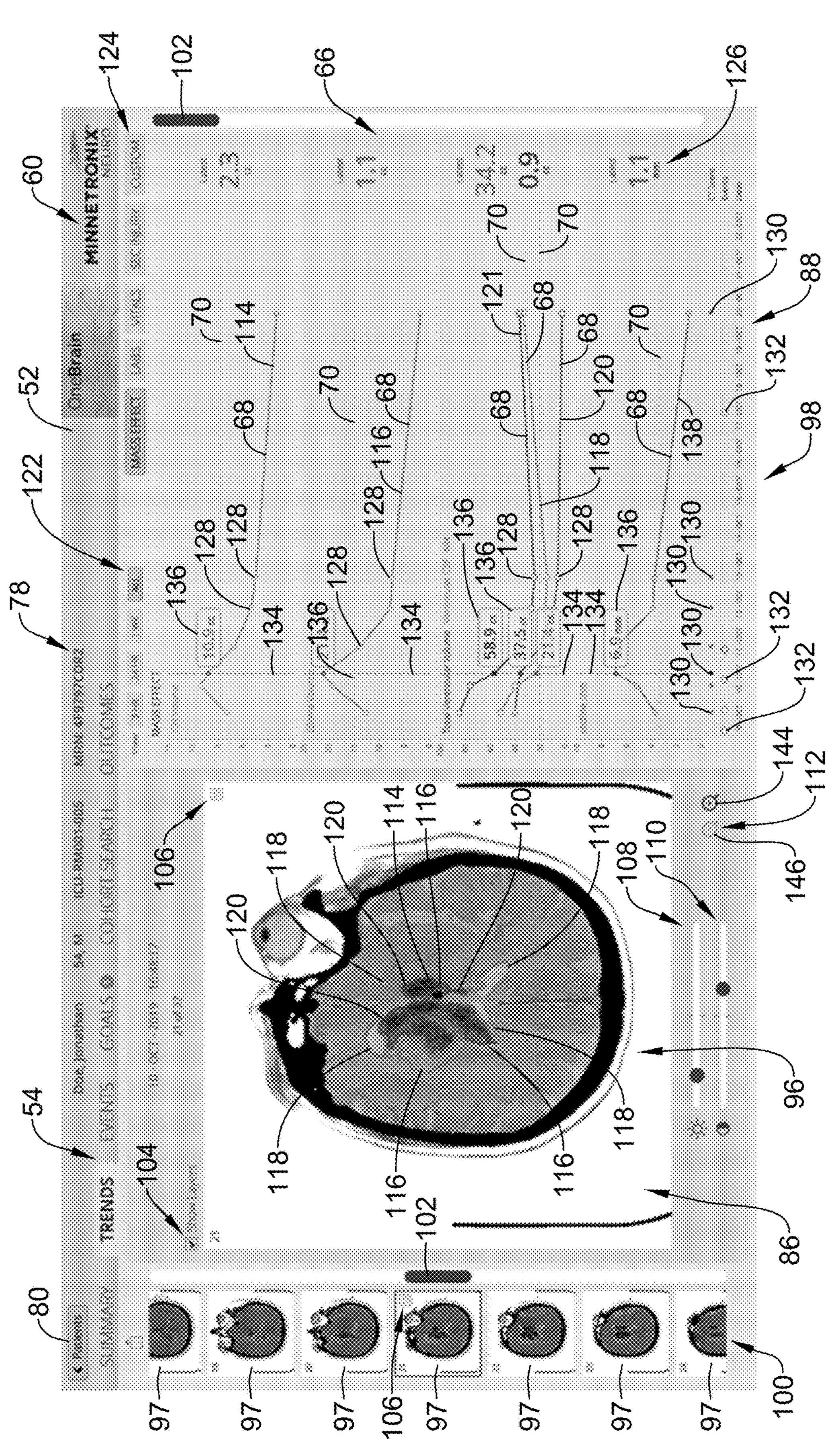

FIG. 8 depicts the trend sub-screen 98 similar to as depicted in FIGS. 6 and 7, but with image 96 taken on Oct. 10, 2019 at 16:48:17 depicted (e.g., the selectable image 97 representing slice "21" of "36" slices of the CT scan may have been selected from the selectable images portion or pane 100). As discussed above, the displayed image 96 may be selected for display in one or more of a variety of ways.

Similar to the changes seen between the image 96 displayed in FIG. 6 and the image 96 displayed in FIG. 7, the area of the ICH volume 114, the area of the edema volume 116, the area of the ventricular CSF volume 118, and the area of the IVH volume 120 in the image 96 displayed in FIG. 8 differ from the sizes and/or shapes of the area of the volumes 114, 116, 118, 120 depicted in the displayed image 96 of FIGS. 6 and 7, which are images of CT scans taken prior to the CT scan producing the image 96 in FIG. 8. The changes in volumes 114, 116, 118, 120 are also evident from changes in the values 136 noted in the parameter portion or pane 66, where the values of the volumes at the time the image 96 depicted in FIG. 8 was taken are an ICH volume 114 of 10.9 cc, an edema volume 116 of 21.4 cc, a ventricular CSF volume 118 is 21.4 cc, an IVH volume 120 of 37.5 cc, a total ventricular volume 121 of 58.9 cc, and a related midline shift of 6.9 mm. These changes are at least partially due to the identified volumes changing in size and/or shape over time and as such, a user may be able to quickly switch between images 96 from different CT scans to view the changes in shape and/or sizes of volumes 114, 116, 118, 120 in addition to comparing precise values presented in the parameter portion or pane 66.

Figure 9:
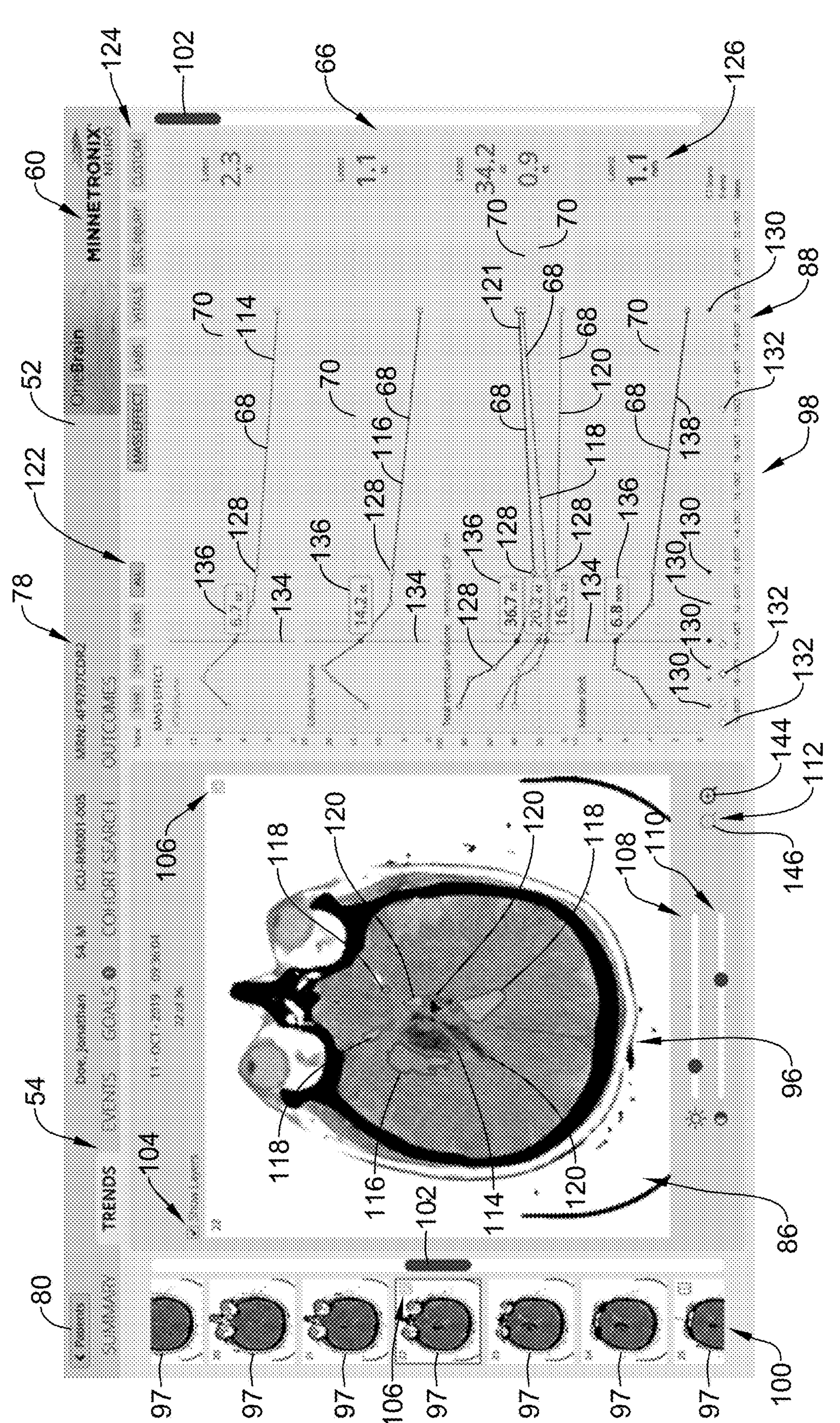

FIG. 9 depicts the trend sub-screen 98 similar to as depicted in FIGS. 6-7, but with image 96 taken on Oct. 11, 2019 at 09:36:04 depicted (e.g., the selectable image 97 representing slice "22" of "36" slices of the CT scan may have been selected from the selectable images portion or pane 100). As discussed above, the displayed image 96 may be selected for display in one or more of a variety of ways.

Similar to the changes seen between the images 96 displayed in FIGS. 6-8, the area of the ICH volume 114, the area of the edema volume 116, the area of the ventricular CSF volume 118, and the area of the IVH volume 120 in the image 96 displayed in FIG. 9 differ from the sizes and/or shapes of the area of the volumes 114, 116, 118, 120 depicted in the displayed image 96 of FIGS. 6-8, which are images of CT scans taken prior to the CT scan producing the image 96 in FIG. 9. The changes in volumes 114, 116, 118, 120 are also evident from changes in the values 136 noted in the parameter portion or pane 66, where the values of the volumes at the time the image 96 depicted in FIG. 9 was taken are an ICH volume 114 of 6.7 cc, an edema volume 116 of 14.2 cc, a ventricular CSF volume 118 is 16.5 cc, an IVH volume 120 of 20.2 cc, a total ventricular volume 121 of 36.7 cc, and a related midline shift of 6.8 mm. These changes are at least partially due to the identified volumes changing in size and/or shape over time and as such, a user may be able to quickly switch between images 96 from different CT scans to view the changes in shape and/or sizes of volumes 114, 116, 118, 120 in addition to comparing precise values presented in the parameter portion or pane 66.

Figure 10:
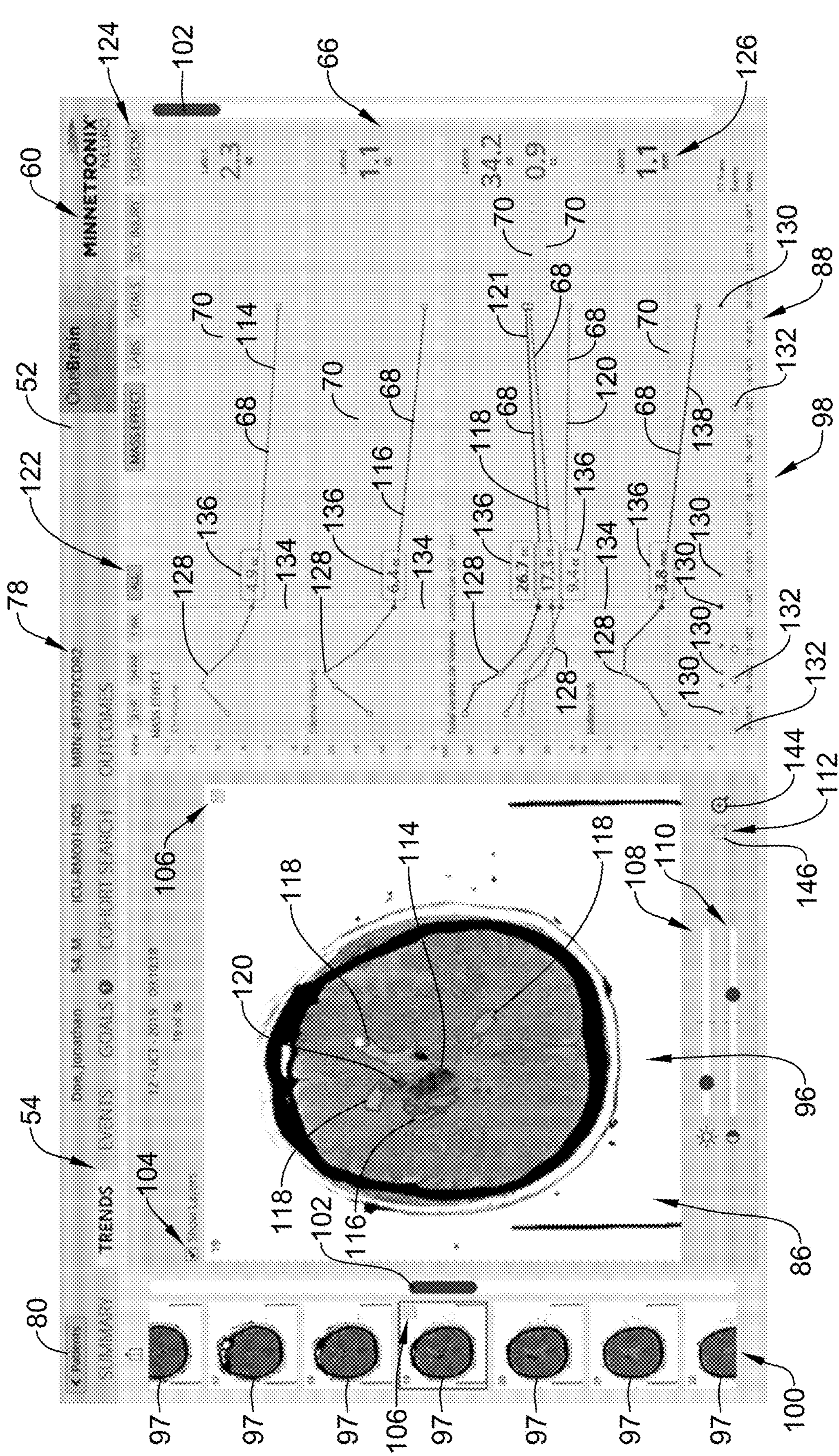

FIG. 10 depicts the trend sub-screen 98 similar to as depicted in FIGS. 6-9, but with image 96 taken on Oct. 12, 2019 at 09:10:18 depicted (e.g., the selectable image 97 representing slice "19" of "36" slices of the CT scan may have been selected from the selectable images portion or pane 100). As discussed above, the displayed image 96 may be selected for display in one or more of a variety of ways.

Similar to the changes seen between the images 96 displayed in FIGS. 6-9, the area of the ICH volume 114, the area of the edema volume 116, the area of the ventricular CSF volume 118, and the area of the IVH volume 120 in the image 96 displayed in FIG. 10 differ from the sizes and/or shapes of the areas of the volumes 114, 116, 118, 120 depicted in the displayed image 96 of FIGS. 6-9, which are images of CT scans taken prior to the CT scan producing the image 96 in FIG. 10. The changes in volumes 114, 116, 118, 120 are also evident from changes in the values 136 noted in the parameter portion or pane 66, where the values of the volumes at the time the image 96 depicted in FIG. 10 was taken are an ICH volume 114 of 4.9 cc, an edema volume 116 of 6.4 cc, a ventricular CSF volume 118 is 17.3 cc, an IVH volume 120 of 9.4 cc, a total ventricular volume 121 of 26.7 cc, and a related midline shift of 3.8 mm. These changes are at least partially due to the identified volumes changing in size and/or shape over time and as such, a user may be able to quickly switch between images 96 from different CT scans to view the changes in shape and/or sizes of volumes 114, 116, 118, 120 in addition to comparing precise values presented in the parameter portion or pane 66.

Figure 11:
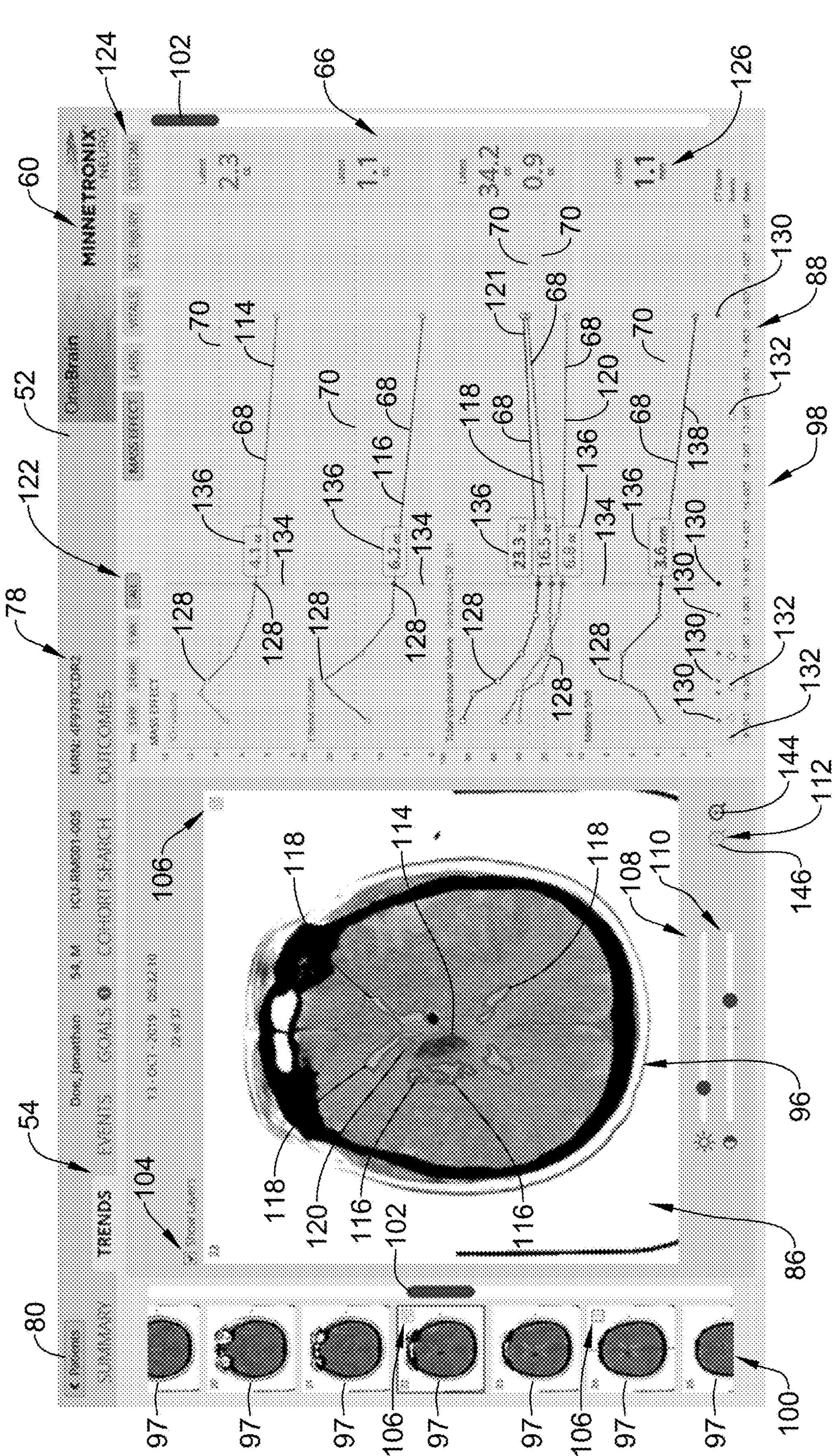

FIG. 11 depicts the trend sub-screen 98 similar to as depicted in FIGS. 6-10, but with image 96 taken on Oct. 13, 2019 at 05:32:10 depicted (e.g., the selectable image 97 representing slice "22" of "37" slices of the CT scan may have been selected from the selectable images portion or pane 100). As discussed above, the displayed image 96 may be selected for display in one or more of a variety of ways.

Similar to the changes seen between the images 96 displayed in FIGS. 6-10, the area of the ICH volume 114, the area of the edema volume 116, the area of the ventricular CSF volume 118, and the area of the IVH volume 120 in the image 96 displayed in FIG. 11 differ from the sizes and/or shapes of the areas of the volumes 114, 116, 118, 120 depicted in the displayed image 96 of FIGS. 6-10, which are images of CT scans taken prior to the CT scan producing the image 96 in FIG. 11. The changes in volumes 114, 116, 118, 120 are also evident from changes in the values 136 noted in the parameter portion or pane 66, where the values of the volumes at the time the image 96 depicted in FIG. 11 was taken are an ICH volume 114 of 4.1 cc, an edema volume 116 of 6.2 cc, a ventricular CSF volume 118 is 16.5 cc, an IVH volume 120 of 6.8 cc, a total ventricular volume 121 of 23.3 cc, and a related midline shift of 3.6 mm. These changes are at least partially due to the identified areas of the volumes changing in size and/or shape over time and as such, a user may be able to quickly switch between images 96 from different CT scans to view the changes in shape and/or sizes of volumes 114, 116, 118, 120 in addition to comparing precise values presented in the parameter portion or pane 66.

Figure 12:
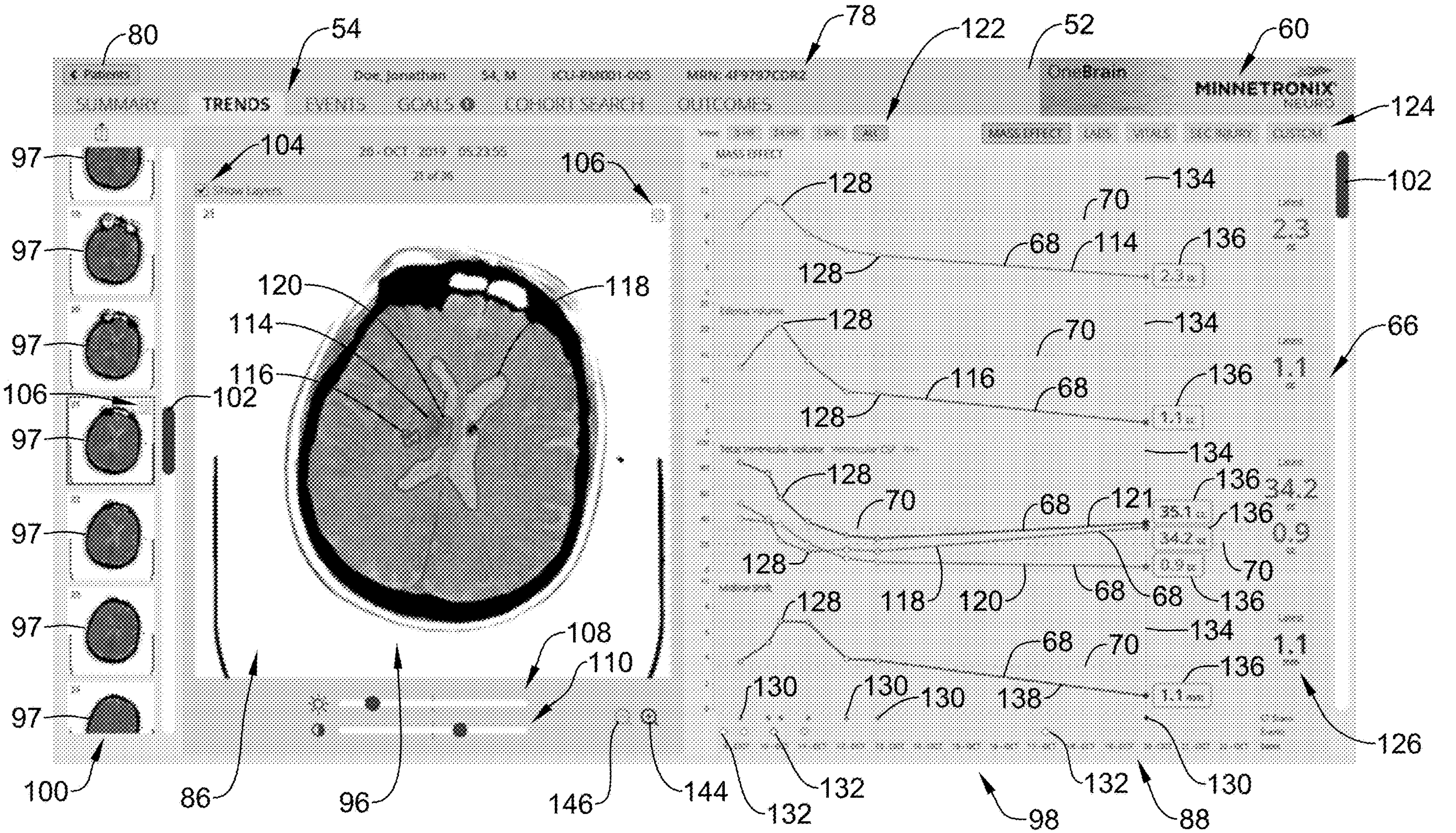

FIG. 12 depicts the trend sub-screen 98 similar to as depicted in FIGS. 6-11, but with image 96 taken on Oct. 20, 2019 at 05:23:55 depicted (e.g., the selectable image 97 representing slice "21" of "36" slices of the CT scan may have been selected from the selectable images portion or pane 100). As discussed above, the displayed image 96 may be selected for display in one or more of a variety of ways.

Similar to the changes seen between the images 96 displayed in FIGS. 6-11, the area of the ICH volume 114, the area of the edema volume 116, the area of the ventricular CSF volume 118, and the area of the IVH volume 120 in the image 96 displayed in FIG. 12 differ from the sizes and/or shapes of the areas of the volumes 114, 116, 118, 120 depicted in the displayed image 96 of FIGS. 6-11, which are images of CT scans taken prior to the CT scan producing the image 96 in FIG. 12. The changes in volumes 114, 116, 118, 120 are also evident from changes in the values 136 noted in the parameter portion or pane 66, where the values of the volumes at the time the image 96 depicted in FIG. 12 was taken are an ICH volume 114 of 2.3 cc, an edema volume 116 of 1.1 cc, a ventricular CSF volume 118 is 34.2 cc, an IVH volume 120 of 0.9 cc, a total ventricular volume 121 of 35.1 cc, and a related midline shift of 1.1 mm. These changes are at least partially due to the identified volumes changing in size and/or shape over time and as such, a user may be able to quickly switch between images 96 from different CT scans to view the changes in shape and/or sizes of volumes 114, 116, 118, 120 in addition to comparing precise values presented in the parameter portion or pane 66.

Figure 13:
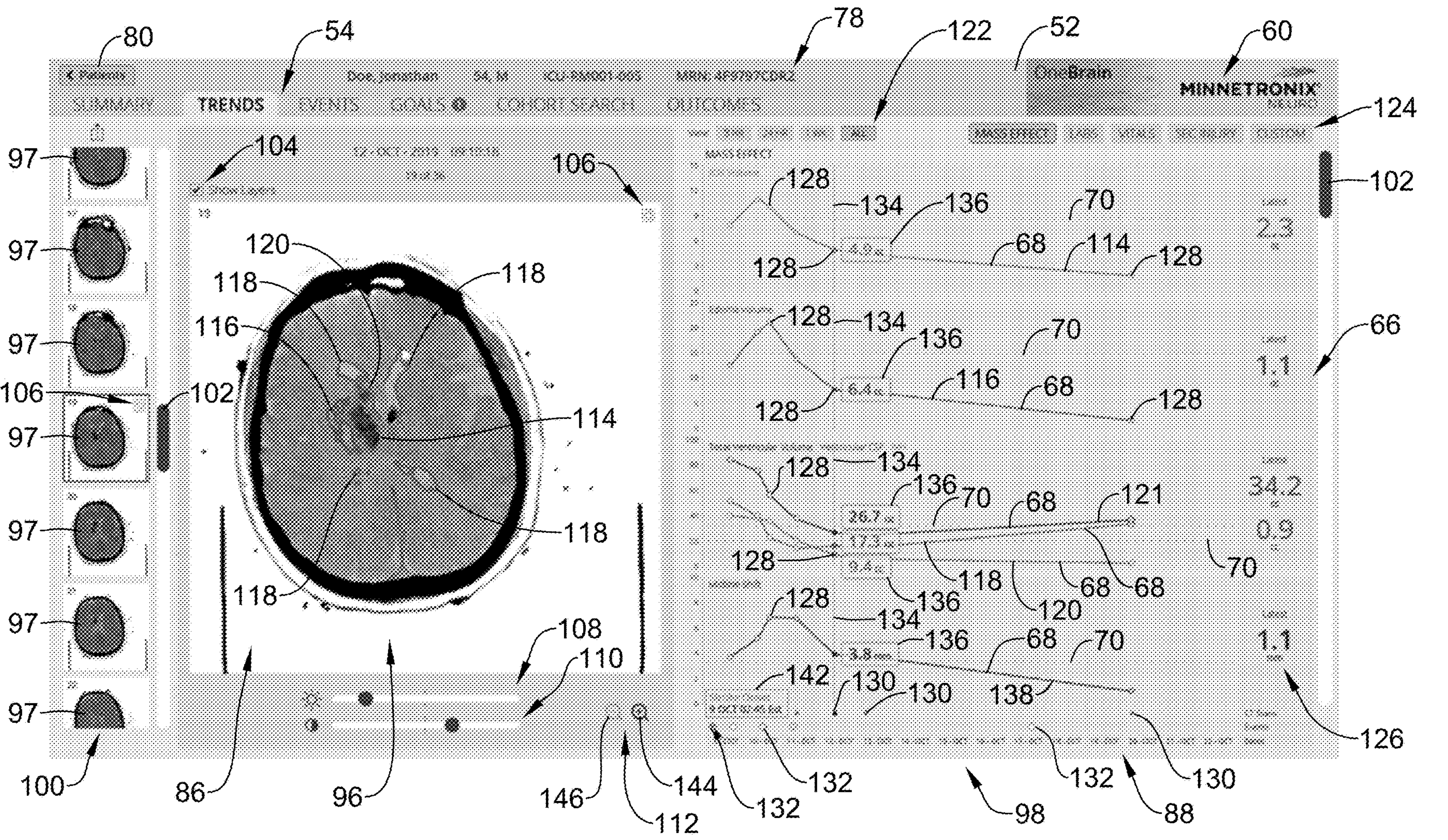

FIGS. 13-17 depict the trend sub-screen 98 of FIG. 10, but with event indicators 132 selected. FIG. 13 depicts the trend sub-screen 98 with a first (if viewed in chronological order from left to right) event indicator 132 selected. A selected event may be indicated by a filled-in indicator 132, but this is not required and one or more other suitable indications of a selected indicator 132 may be provided. In some cases, a user may select an event indicator (or other suitable selectable element) via cursor 140 and/or other suitable selecting mechanism.

In response to selecting the first event indicator 132, a pop-up box 142 may be displayed that displays information related to the noted and selected event. In some cases, the pop-up box 142 may indicate a type of event occurrence (e.g., a stroke onset, etc.), a date of the event, a time of the event, and/or other relevant information concerning the event. As depicted in the pop-up box 142 of FIG. 13, the event is a stroke onset occurring on October 9$^{th}$ at 02:45 Eastern Standard Time (EST).

In some cases, the event indicators 132 may be color coded, shape coded, or otherwise have a configuration associated with a particular event, but this is not required. In one example, an indicator 132 associated with a stroke onset event (e.g., from the left to right, the first indicator 132 depicted in FIGS. 13-17) may be orange, an indicator 132 associated with a surgical event (e.g., from the left to right, the second and fifth indicators 132 depicted in FIGS. 13-17) may be blue, and an indicator 132 associated with a medical event (e.g., from the left to right, the third and fourth indicators 132 depicted in FIGS. 13-17) may be purple. Other types of coding configurations may be utilized for indicating a type of event with which the event indicators 132 are associated, as desired.

Figure 14:
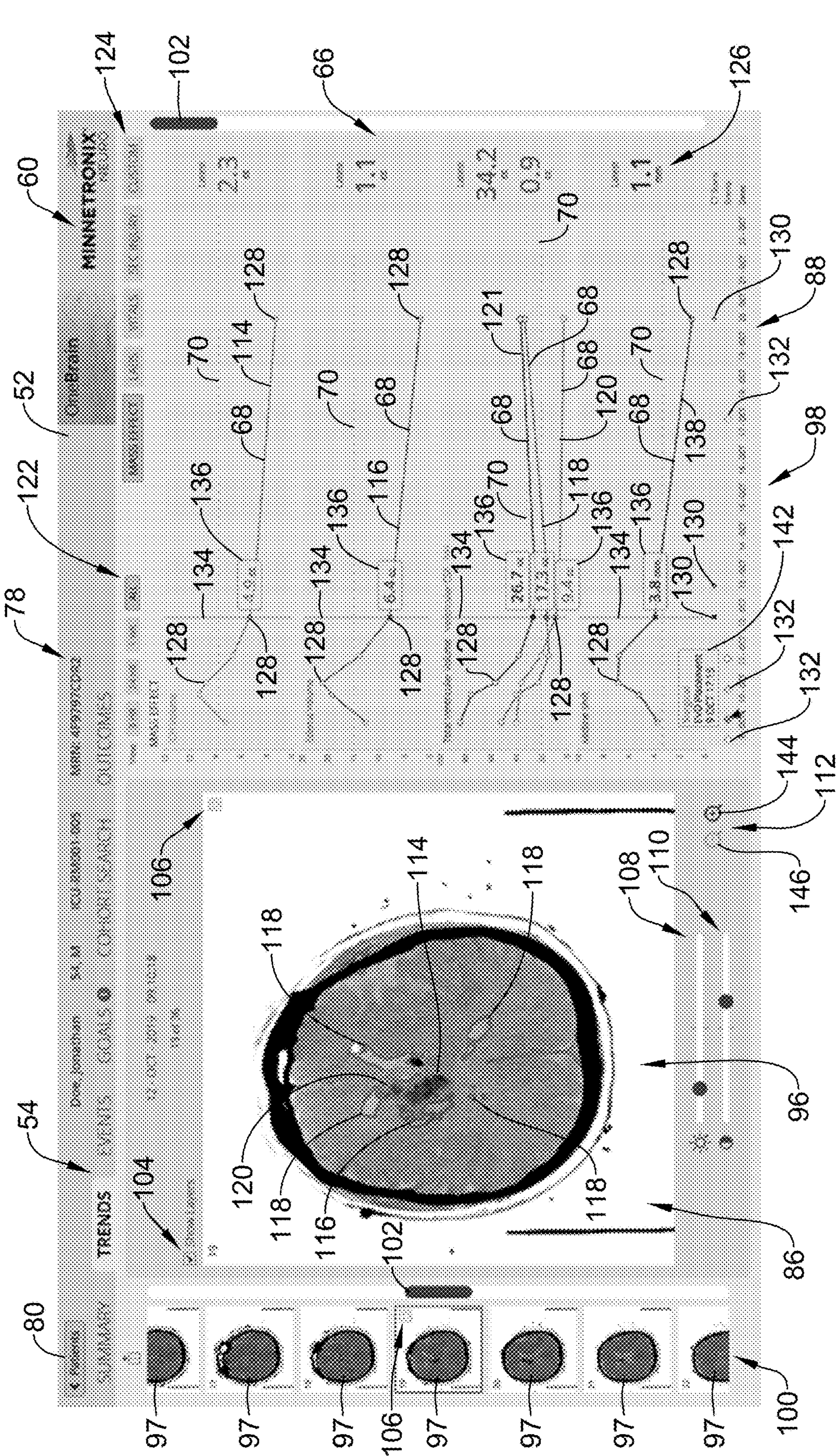

FIG. 14 depicts the trend sub-screen 98 with a second event indicator 132 selected, which has a configuration indicating the event is a surgical event. In response to selecting the second event indicator 132, a pop-up box 142 may be displayed that displays information related to the noted and selected event. As depicted in the pop-up box 142 of FIG. 14, the event is a surgical event in which an external ventricular drain (EVD) was placed, which occurred on October 9 at 17:15 EST.

Figure 15:
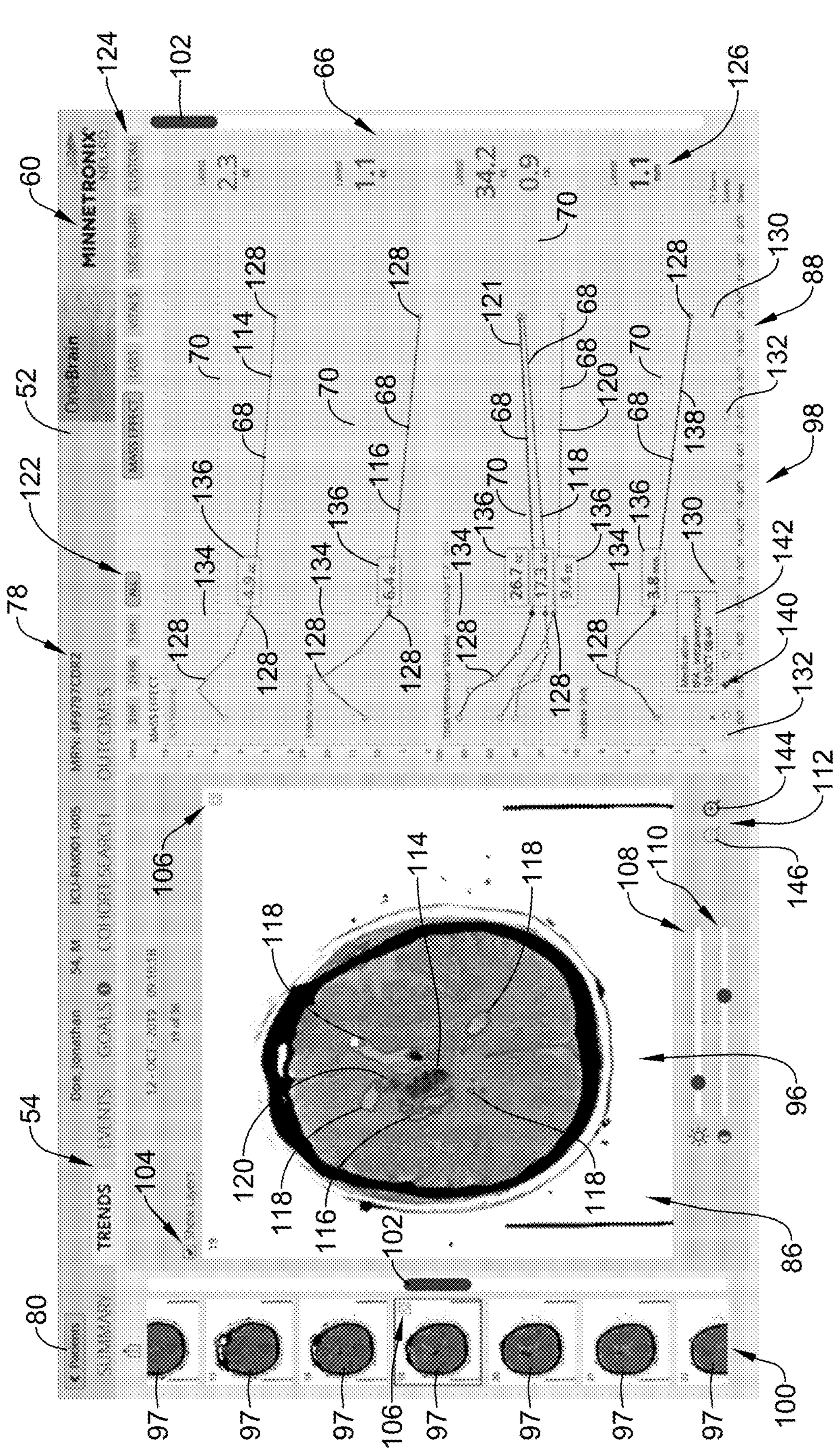

FIG. 15 depicts the trend sub-screen 98 with a third event indicator 132 selected, which has a configuration indicating the event is a medication event. In response to selecting the third event indicator 132, a pop-up box 142 may be displayed that displays information related to the noted and selected event. As depicted in the pop-up box 142 of FIG. 15, the event is a medication event in which tPA was administered intraventricularly on October $10^{th}$ at 08:44 EST.

Figure 16:
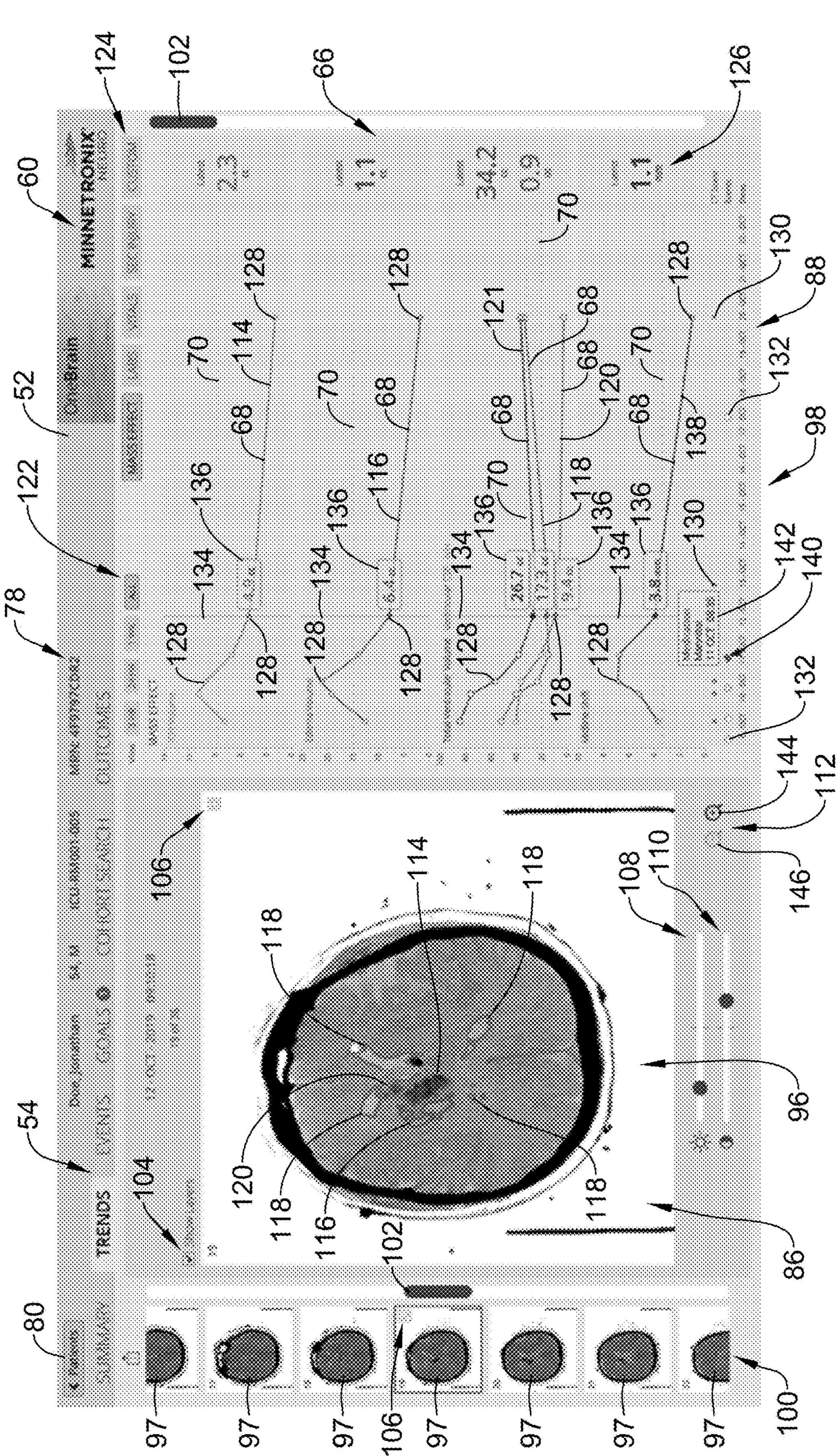

FIG. 16 depicts the trend sub-screen 98 with a fourth event indicator 132 selected, which has a configuration indicating the event is a medication event. In response to selecting the fourth event indicator 132, a pop-up box 142 may be displayed that displays information related to the noted and selected event. As depicted in the pop-up box 142 of FIG. 16, the event is a medication event in which Mannitol was administered on October $11^{th}$ at 08:35 EST.

Figure 17:
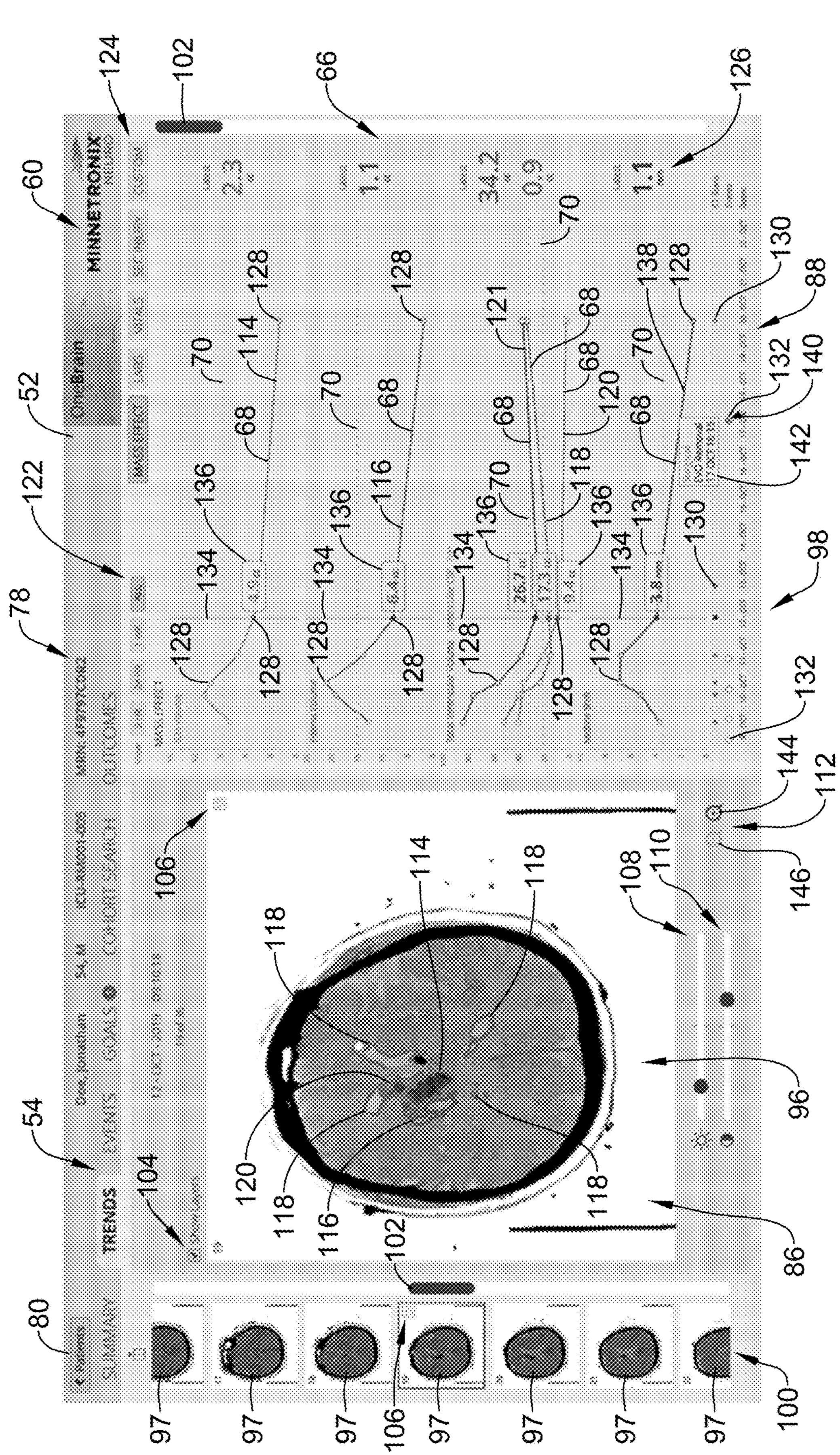

FIG. 17 depicts the trend sub-screen 98 with a fifth event indicator 132 selected, which has a configuration indicating the event is a surgical event. In response to selecting the fifth event indicator 132, a pop-up box 142 may be displayed that displays information related to the noted and selected event. As depicted in the pop-up box 142 of FIG. 17, the event is a surgical event in which the previously placed EVD was removed on October 17 at 16:15 EST.

Figure 18:
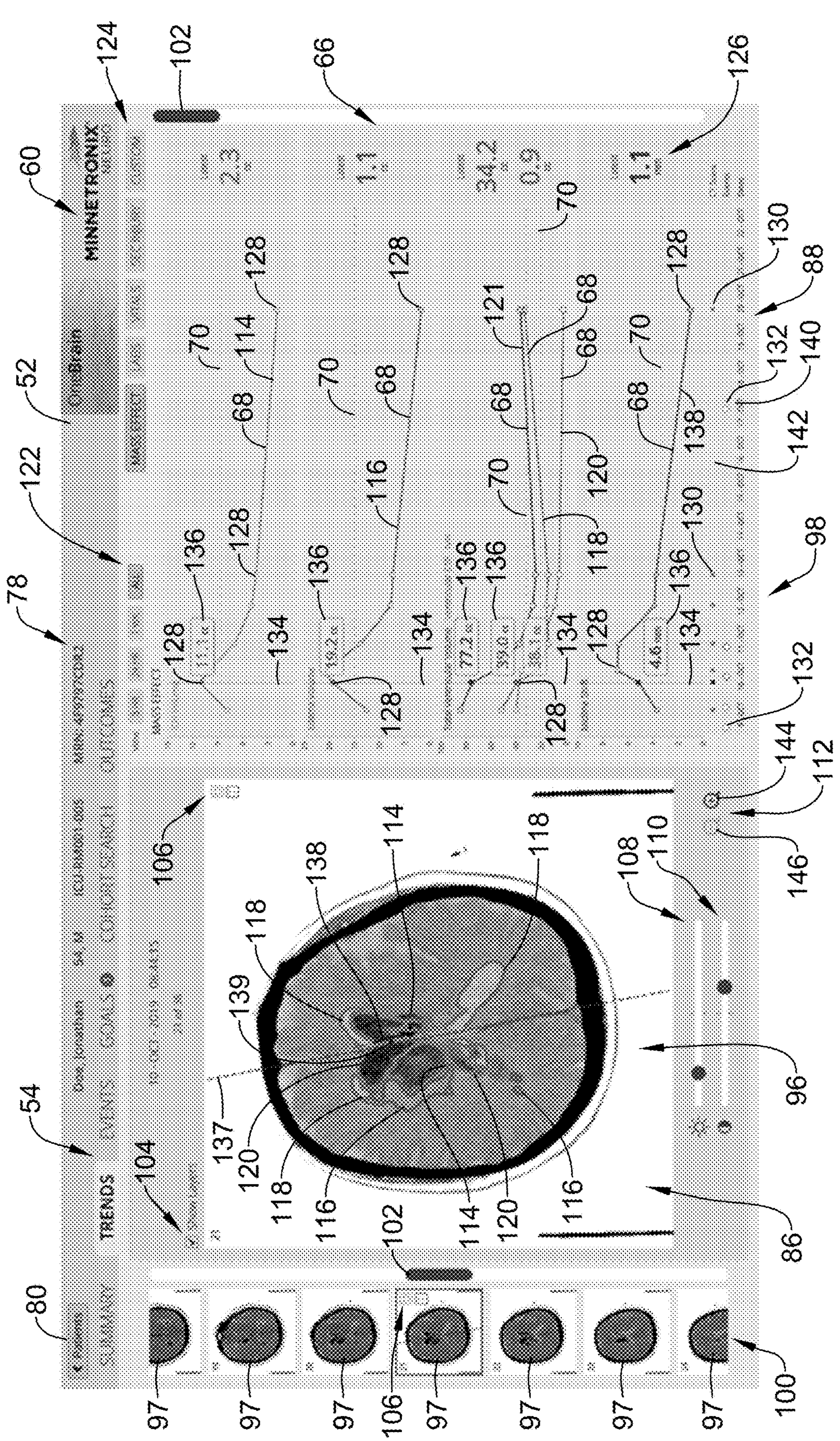
Figure 19:
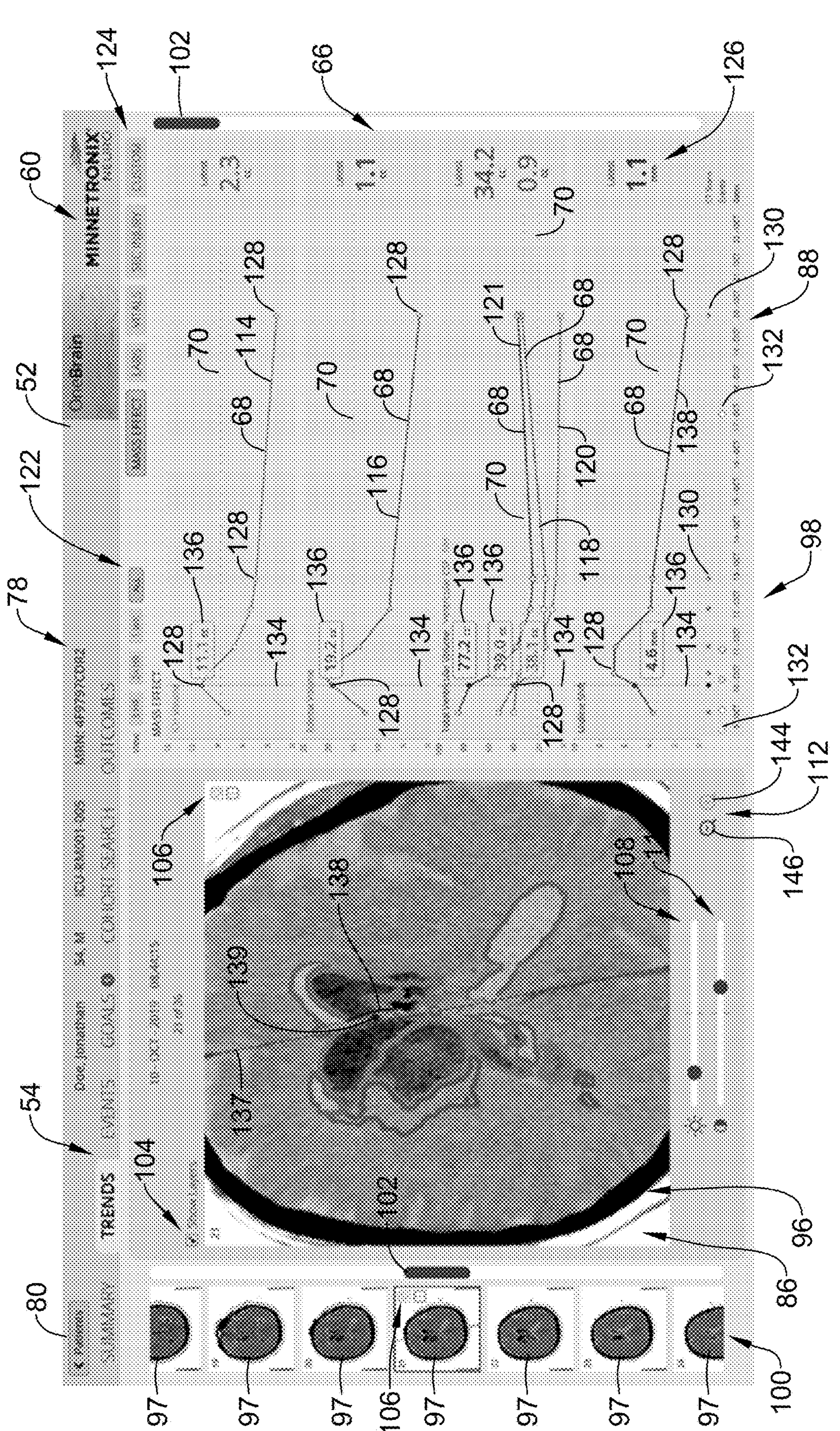

FIGS. 18 and 19 depict an illustrative interaction with the zoom adjustment area 112 of the image pane or portion 86, having a selectable zoom-in button 144 and a selectable zoom-out button 146. Although the zoom-in and zoom-out features are depicted as selectable buttons, the zoom-in and/or zoom-out features may take on one or more other suitable selectable configurations to adjust a zoom level of the depicted image 96 including, but not limited to, a zoom bar with a selectable slider.

FIG. 18 is substantially the same trend sub-screen 98 view that is depicted in FIG. 7, in which the image 96 is zoomed all of the way out as evidenced by the zoom-out button 146 being shown in a dark gray. As such, a user may select the zoom-in button 144 to zoom-in on the image 96.

FIG. 19 is the trend sub-screen 98 view depicted in FIG. 18, but with the image 96 zoomed all of the way in as evidenced by the zoom in button 144 being shown in dark gray. As such, a user may select the zoom-out button 146 to zoom-out on the image 96. Although FIGS. 18 and 19 depicted the image 96 zoomed all of the way out on and all of the in on, respectively, the selectable zoom-in button 144 and the selectable zoom-out button 146 may be utilized to zoom to any desired zoom level.

Further, although not depicted, a user may be able to select the image 96 and pan the image 96 up and down and/or side-to-side, but this is not required. When an ability to pan an image is provided, the panning may occur at any selected zoom level.

Figure 20:
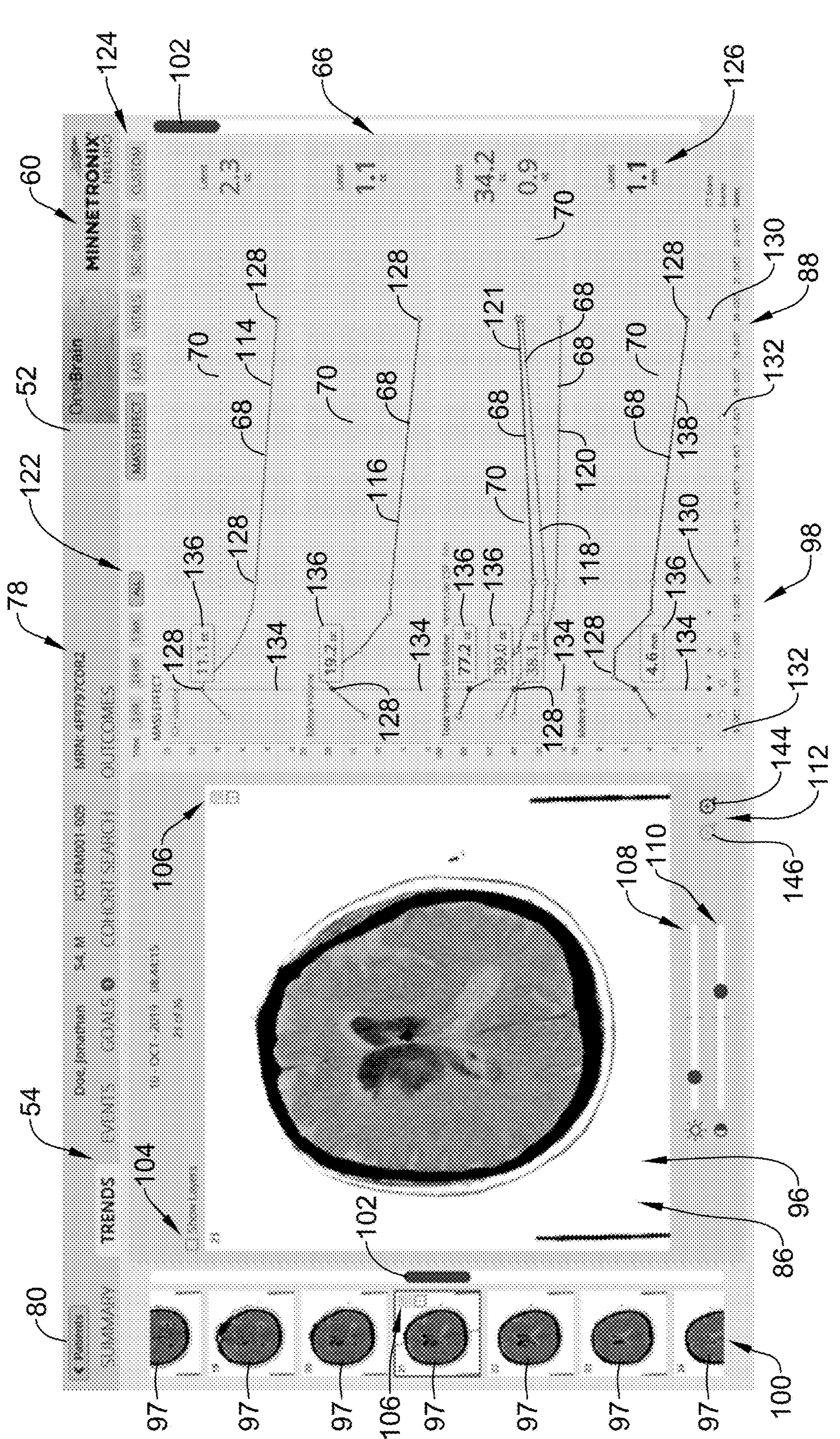

FIG. 20 depicts an illustrative interaction with the layers button 104 in the trend sub-screen 98, similar to as depicted in FIG. 7. In the screen of FIG. 7, the layer button 104 is selected, which may cause the area of the ICH volume 114, the area of the edema volume 116, the area of the ventricular CSF volume 118, the area of the IVH volume 120, the midline 137, the midline shift line 138, and the midline shift arrow 139 to be highlighted or otherwise depicted on or overlapping the image 96.

As shown in FIG. 20, the layer button 104 may be de-selected, which may cause the highlighting of the area of the ICH volume 114, the area of the edema volume 116, the area of the ventricular CSF volume 118, the area of the IVH volume 120, the midline 137, the midline shift line 138, and the midline shift arrow 139 to be removed from the screen. Even when the layers button 104 is not selected or is unchecked, the values of the parameter determined by or in conjunction with the image 96 may be provided in the parameter pane or portion 66, as discussed herein. Further, although selecting the layers button 104 may cause all parameter areas to be displayed and de-selecting the layers button 104 may cause none of the parameter areas to be displayed, the layers button 104 may include one or more selectable features to facilitate displaying some, but not all parameter areas to facilitate displaying only information a user determines is relevant to their analysis.

Figure 21:
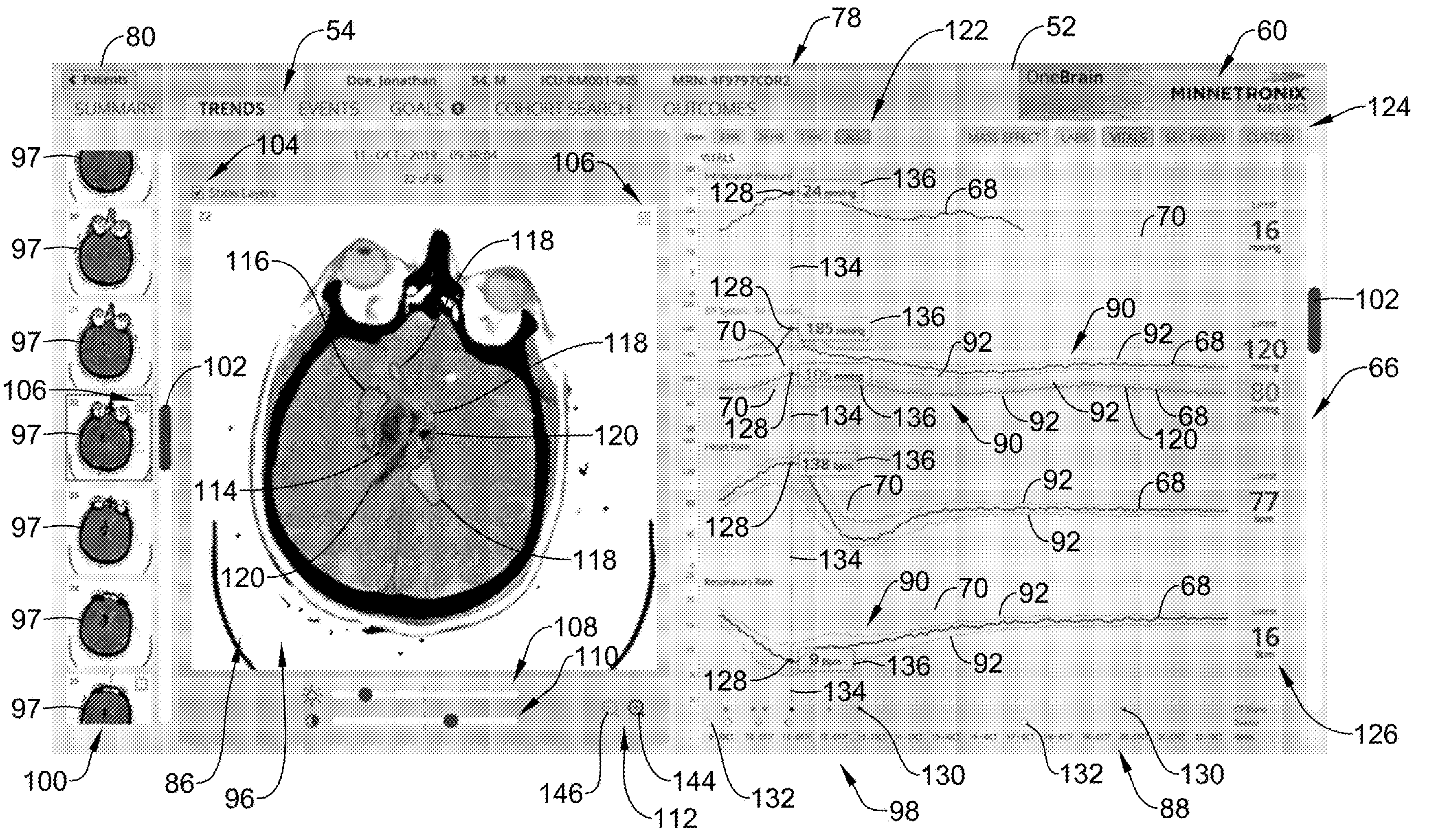
FIG. 21 is a schematic example of a trend sub-screen for display on a user interface and depicting information related to vitals of a selected patient.

FIG. 21 depicts the trend sub-screen 98 in which a VITALS option in the selectable parameter data area 124 of the parameter pane or portion 66 is selected. In some cases, the VITALS option may be configured to display data and/or trends of data related to a patient's vital signs. Other than the types of data displayed in the parameter pane or portion 66, the trend sub-screen 98 may include features similar to those discussed above with respect to the trend sub-screens 98 of FIGS. 6-20.

The parameters related to vitals of a patient that are displayed in the parameter pane or portion 66 may be any suitable type of vitals-related parameters. As depicted in FIG. 21, the parameters displayed in the parameter pane or portion 66 may include, but is not limited to, intracranial pressure (ICP), BP systolic, BP diastolic, heart rate, and respiratory rate.

Similar to as discussed with respect to other parameters, the data related to the depicted parameters may be presented in trend lines 68, but this is not required and the data may be presented in one or more other suitable formats. In some cases, a range 90 of values of the patient parameters may be provided along the trend line 68 or the timeline 88 to show or otherwise demonstrate a variability of the parameter. The range 90 may have lines 92 marking upper and lower values, or variability, of the range 90. Although not required, the area between the lines 92 may be shaded to facilitate visually representing the range to a user. As discussed above with respect to heart rate variability, a user being able to quick grasp a variability of a parameter may facilitate the user understanding a patient's overall condition. Further, a user may be able to zoom-in and/or zoom-out on the range 90 to get different granularity of data.

Similar to as depicted in the other trend sub-screens 98, each parameter displayed includes data over time, a trend line 68 of the parameter data over time, one or more parameter goal thresholds or lines 70 (e.g., as represented by a dashed line), and a current or latest reading of the parameter may be viewed in a current parameter value area 126. As discussed above, positioning a current or latest reading of a sensed parameter at an end of the parameter data over time may facilitate a user quickly reviewing the parameter portion or pane 66 and determining how a patient's current condition compares to the patient's condition over time and relative to a parameter goal.

Figure 22:
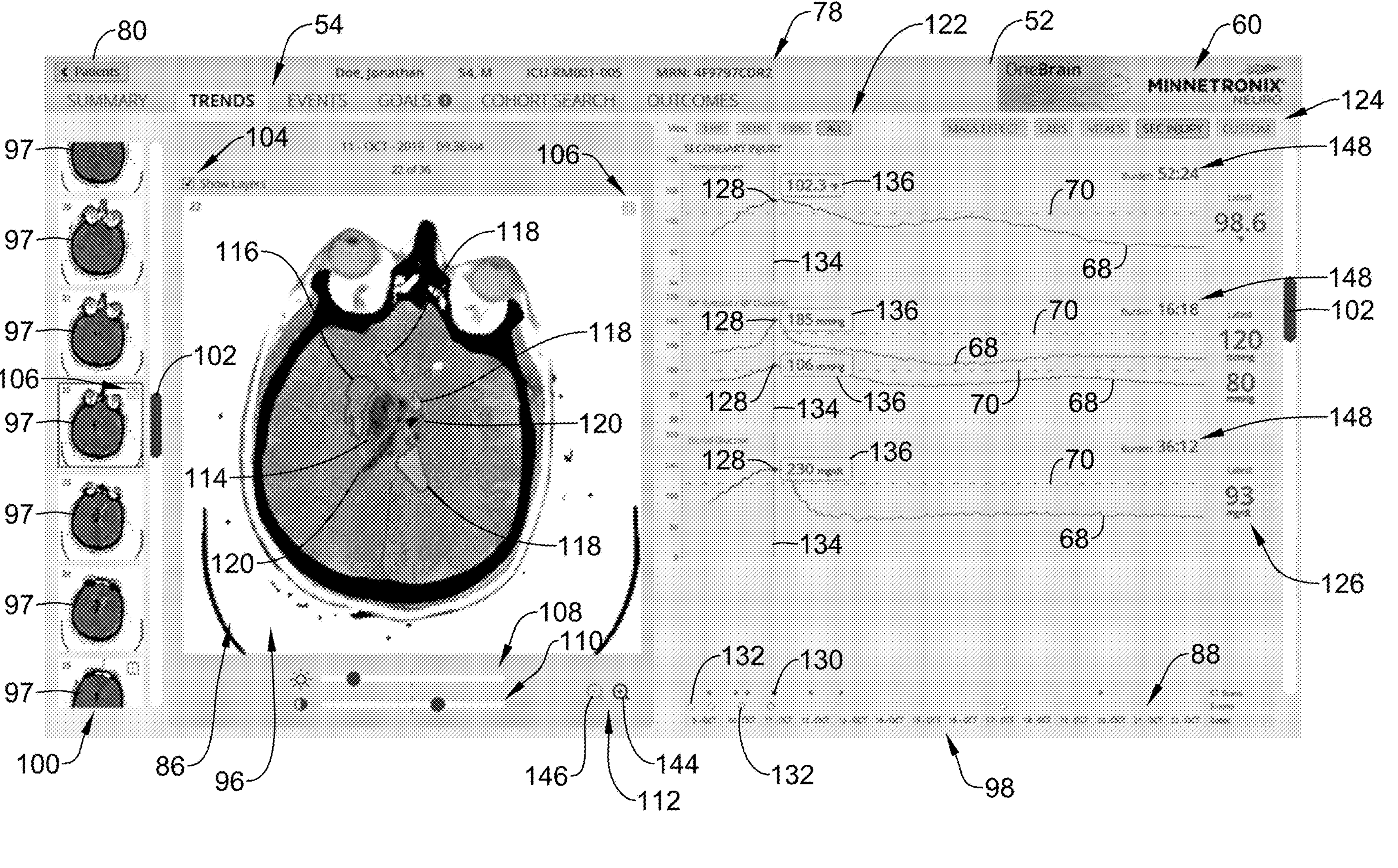
FIG. 22 is a schematic example of a trend sub-screen for display on a user interface and depicting information related to a secondary injury of a selected patient.

FIG. 22 depicts the trend sub-screen 98 in which a SEC INJURY option in the selectable parameter data area 124 of the parameter pane or portion 66 is selected. In some cases, the SEC INJURY option may be configured to display data and/or trends of data related to a patient's potential secondary injuries. Other than the types of data displayed in the parameter pane or portion 66, the trend sub-screen 98 may include features similar to those discussed above with respect to the trend sub-screen 98 of FIGS. 6-21.

The parameters related to secondary injuries of a patient that are displayed in the parameter or portion 66 may be any suitable types of secondary injury-related parameters. As depicted in FIG. 22, the parameters displayed in the parameter pane or portion 66 may include, but are not limited to, body temperature, BP systolic, BP diastolic, and blood glucose.

Similar to as discussed with respect to other parameters, the data related to the depicted parameters may be presented in trend lines 68, but this is not required and the data may be presented in one or more other suitable formats. Although not depicted, a range of values of the patient parameters may be provided along the trend line 68 or the timeline 88 to show or otherwise demonstrate a variability of the parameter.

Similar to as depicted in the other trend sub-screens 98, each parameter displayed includes data over time, a trend line 68 of the parameter data over time, one or more parameter goal thresholds or lines 70 (e.g., as represented by a dashed line), and a current or latest reading of the parameter may be viewed in a current parameter value area 126. In some cases, the trend lines 68 may be coded to provide a visual indication of a value of the parameter relative to the parameter goal threshold or line 70. For example, the trend line 68 may get brighter, get darker, change color, get thicker, get thinner, etc. as it reaches and/or goes beyond the goal threshold or line 70. Similar coding may be provided with other trend lines 68 discussed herein and may be consider a notification to a user of approaching, reaching, and/or going beyond a threshold or goal. Further, one or more of the parameters displayed (and/or one or more parameter displayed in other screens) may include an area of elapsed time 148 that provides an accumulated amount of time (e.g., which may be a notification) the trend line 68 and/or the data associated with the parameter has reached or gone beyond or otherwise exceeds the threshold 70. As depicted in FIG. 22, the area of elapsed time 148 may be labeled "Burden", but this is not required and the area of elapsed time 148 may have no label or may have a different label. Similar to the positioning of the latest parameter measurement value, including the area of elapsed time 148 and/or coding the trend lines 68 based on positioning relative to a threshold or goal may facilitate a user quickly reviewing the parameter portion or pane 66 and determining a patient's condition.

Figure 23:
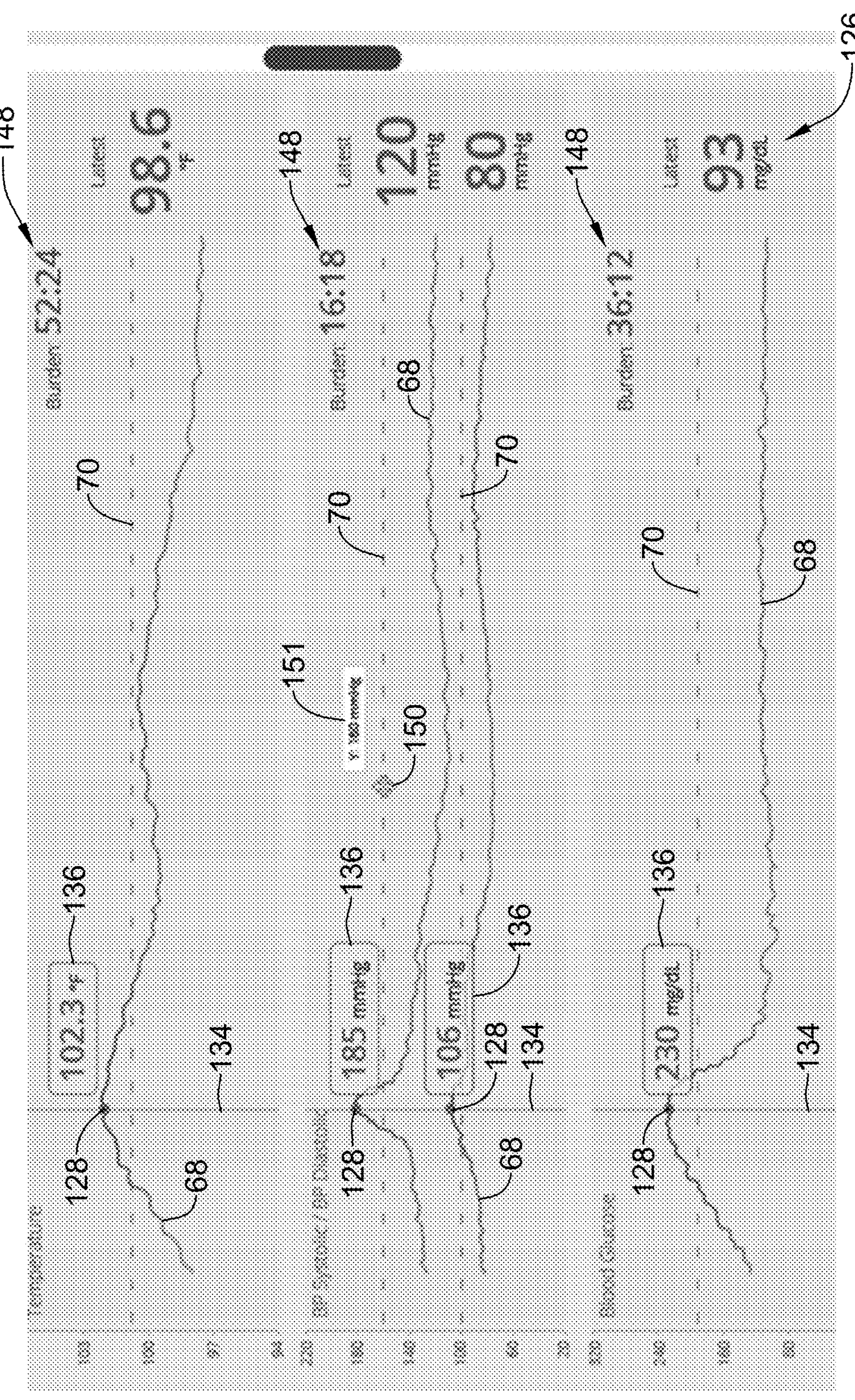
FIG. 23 is a schematic example of an ability to adjust a goal threshold from a trend sub-screen.

The goal thresholds or lines 70 may be standard goals/thresholds and/or may be customized for a certain patient and/or customized based on a condition of the patient. As depicted in FIG. 23, the goal thresholds or lines 70 may be customized from the trend sub-screen 98. In one example, a user may select a goal threshold or line 70 using a selector 150 and may adjust the goal threshold or line 70 up or down as desired. In response to adjusting the goal threshold or line 70, a value at the area of elapsed time 148 may be adjusted in view of the new goal threshold, but this is not required. Further, in some cases, selecting a goal threshold or line 70 may result in a current value 151 of the goal threshold or line 70 selected. The current value 151 of the goal threshold or line 70 selected may be updated as a user adjusts the goal threshold or line 70 to facilitate a user understanding at what level the threshold is set.

Figure 24:
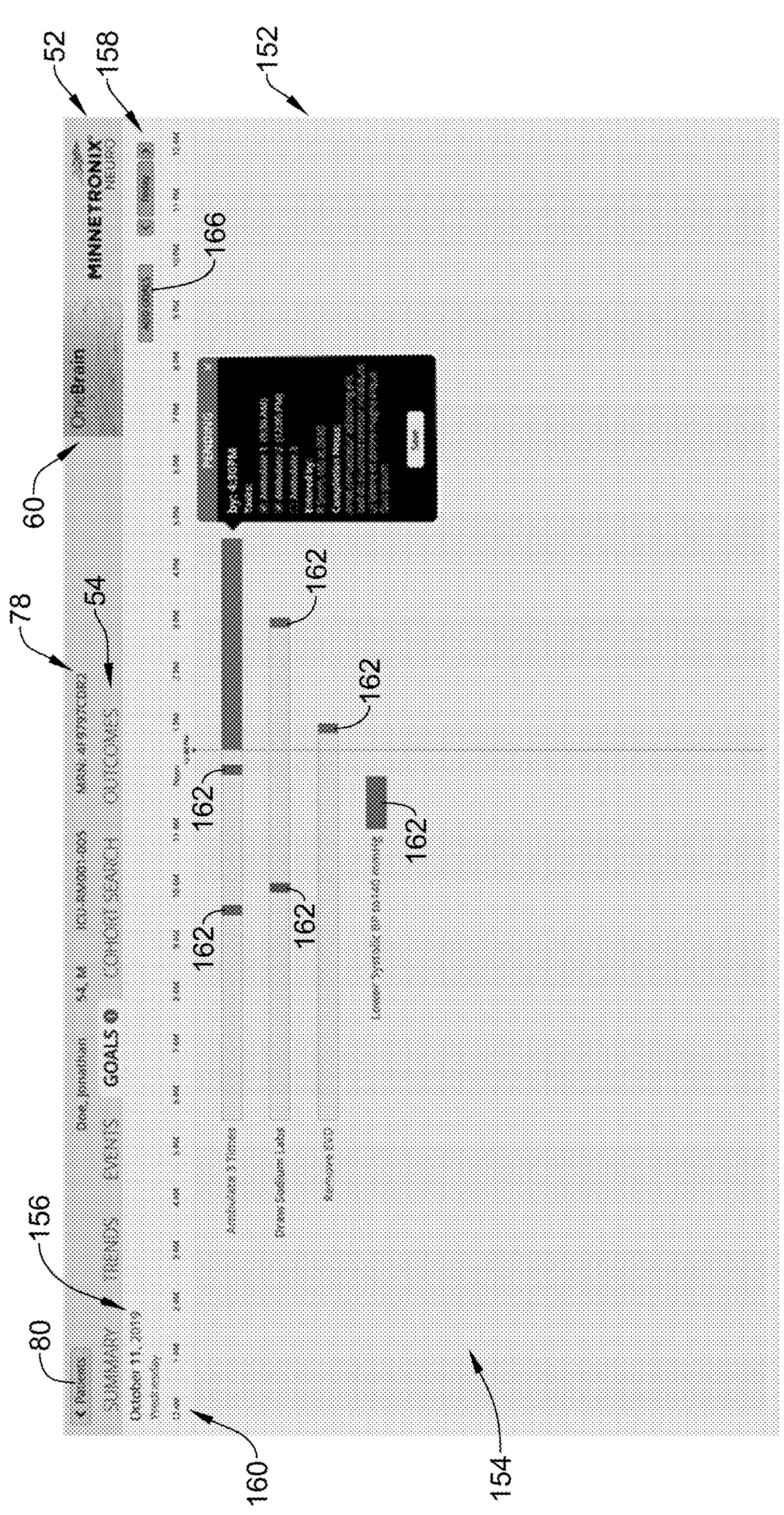
FIG. 24 is a schematic example of a goals sub-screen for display on a user interface.

To facilitate viewing goals of and/or setting goals for a selected patient, a user may select the screen title 54 labeled "GOALS" from the heading portion or pane 52 to advance to a goals sub-screen 152, for example as depicted in FIG. 24. FIG. 24 depicts an illustrative goals sub-screen 152 depicting previously established goals for a selected patient and providing a user an opportunity to adjust the previously established goals and/or set new goals for the selected patient.

The goals sub-screen 152 may include any suitable configuration of panes and/or information. In the example configuration depicted in FIG. 24, the goals sub-screen 152 may display the heading portion or pane 52, a goal portion or pane 154, and/or one or more other suitable portions or panes displaying goal related settings, data, and/or information. As discussed in further detail below, the goal portion or pane 154 may have one or more selectable features configured to facilitate a user viewing, adjusting, and/or setting goals for the selected patient.

The goals sub-screen 152 may include a date portion 156 configured to display a date for which any goals in the goal portion or pane 154 are set. In an example as depicted in FIG. 24, the date portion 156 may be Wednesday, Oct. 11, 2019, and/or one or more other suitable dates, and any goals listed in the goal portion or pane will have been set for at least the date in the date portion 156.

In some cases, the goal sub-screen 152 may include a selectable date change feature 158. The date change feature 158 may be selected to advance the date in the date portion 156 by a predetermined amount of time (e.g., 1 day, 1 week, etc.), to adjust the date in the date portion 156 backward by a predetermined amount of time, to select a date from a calendar, and/or to adjust the date in the date portion 156 in one or more other suitable manners.

The date change feature 158 may have any suitable configuration. In the example depicted in FIG. 24, the date change feature 158 may include a forward pointing arrow selectable to advance the date in the date portion 156, a backward pointing arrow selectable to adjust the date in the date portion 156 backward, and a middle button (e.g., labeled "Today" in FIG. 24) selectable to cause a calendar to be displayed form which a user may selected a desired date. Additionally or alternatively, a user may utilize arrows on a keyboard or on the display, swiping via a touchscreen display, and/or other suitable directional mechanisms to switch between dates.

Further, in some cases, the goals may be displayed in time durations other than by a single day. For example, goals may be displayed as extending over two or more days, a week, two or more weeks, etc.

The goals sub-screen 152 may include a goals timeline 160 for the selected day and/or other suitable time duration. The set goals for the patient may be listed along the goals timeline 160, which may allow a user to view a time at which or during which the goals are to be met. For example, as depicted in FIG. 24, a first goal may be to ambulate three (3) times on Oct. 11, 2019, a second goal may be to draw sodium labs, a third goal may be to remove EVD, and a fourth goal may be to lower systolic BP to 140 mmHg. Other suitable goals and/or other suitable numbers of goals are contemplated.

As depicted in FIG. 24, a box may be utilized adjacent a goal to indicate a start time and a time by which the goal should be achieved. For example, the first goal of ambulating three (3) times is to start at 5:30 AM and to be achieved by 4:30 PM.

In some cases, the goals may include an indicator 162 of when a goal has been achieved and/or of when a goal is to be achieved. Although not required, a configuration of the indicator 162 may be different depending on what it is intended to indicate to a user. For example, the indicator 162 may have a first configuration (color, shading, shape, etc.) when it is indicating an instance of achieving the goal, a second configuration when it is indicating an instance of when a goal was not met, and a third configuration when it is indicating an instance of when a goal is to be achieved.

That is, the indicator 162 may provide different indications depending on whether a goal has been met, is to be met at a future time, and/or the goal should have been met and has not been met. In some cases, when a goal should have been met and has not been met, the management system 10 may provide a notification in addition to or as an alternative to adjusting the indictor 162. The notification may be an alert on the management system 10 and/or a message outputted to a user (e.g., an email, a text message, a sound, etc.).

In response to selecting (e.g., scrolling over, clicking on, etc.) a goal listed in the goal portion or pane 154, a goal summary 164 may be displayed that is associated with the selected goal. The goal summary 164 may be a summary page that provides a user an overview of whether and/or when a goal was met without the need to go to a full patient summary page or a trends page and review date to assess whether the goal has been met.

As depicted in FIG. 24, the goal summary 164 may include a deadline for the goal to be completed (e.g., 4:30 PM), tasks associated with the goal (e.g., Ambulate 1, Ambulate 2, Ambulate 3), an indication as to whether the goal was achieved (e.g., checks in check boxes and/or other suitable indications of completing a task), a time at which a task was competed (e.g., 9:30 AM, 12:05 PM), an indication of a user that entered the goal and/or goal related information (e.g., R. Smith MD), a notes area with for entering notes related to the goal (e.g., notes for meeting the goal, notes related to attempts at meeting the goal, etc.), and/or other suitable goal-related information. Further, the goal summary may have a save button or other selectable button to save any information added to the goal summary by a user.

The goal sub-screen 152 may include an add goals feature 166. The add goals feature 166 may be selectable to allow a user to add one or more goals to a selected patient. In some cases, common goal templates (e.g., standard sets of orders or goals dependent on patient condition, etc.) may be provided and a user may modify such goal templates to meet needs of the selected patient. In some cases, a set of goal templates may be suggested to a user in response to the user selecting the add goals feature 166, where the suggested goal templates may be based on a condition of the selected patient (e.g., based on one or more values of patient parameters). Alternatively or in addition to a user being presented with goal templates, a user may be able to customize one or more goals for the selected patient.

Figure 26:
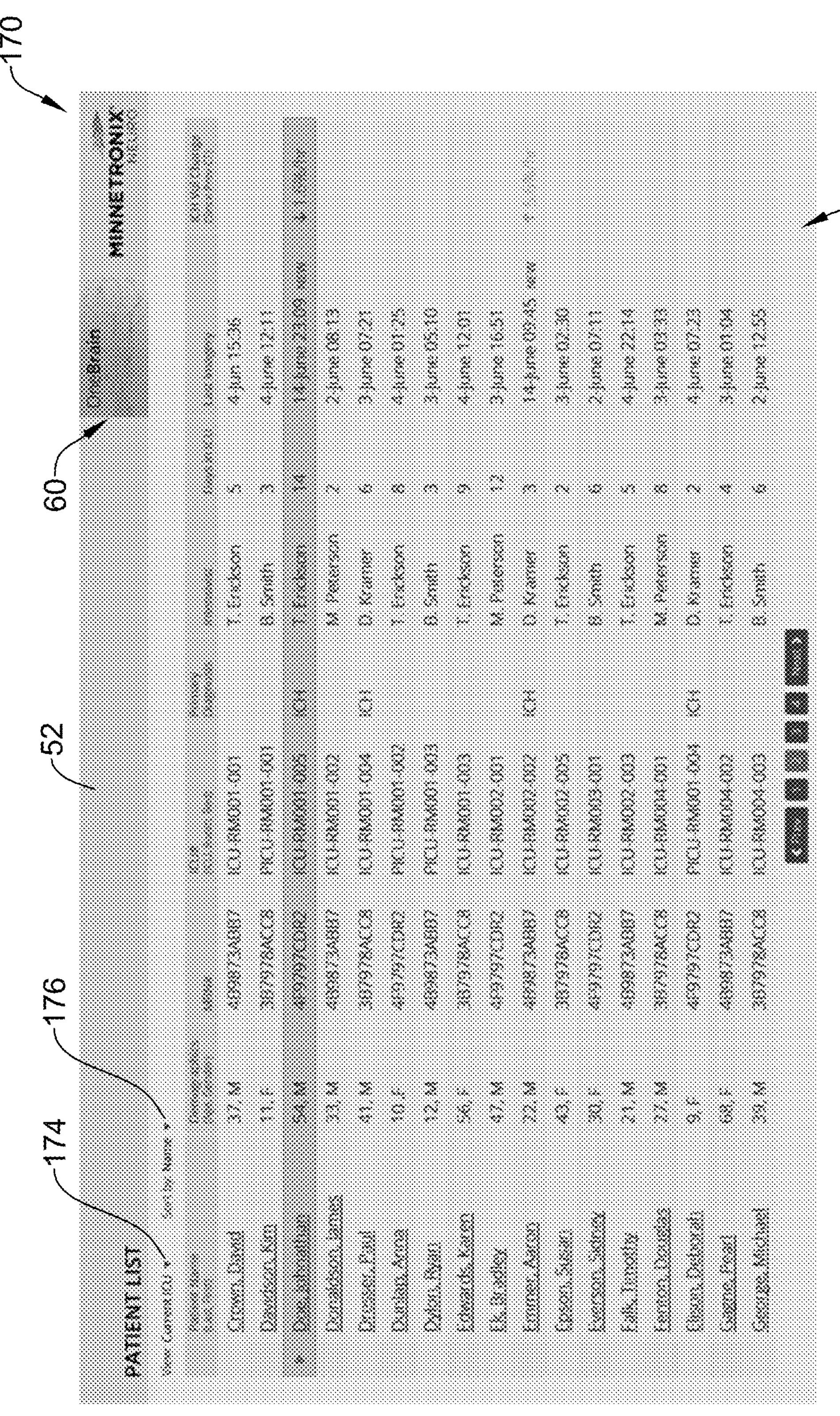
FIG. 26 is a schematic example patient list screen for display on a user interface.

FIG. 26 is a schematic illustration of a patient list screen 170 and may include a heading portion 52 similar to as discussed herein. The patient list screen 170 may include a patient list portion 172. The patient list portion 172 may list data associated with the patient including, but not limited to, age, gender, medical record number (MRN), diagnosis, medical provider (e.g., intensivist), days in ICU, a date of last imagery, indications of new imagery, changes in hemorrhage volume (e.g., ICH volume change), and/or other suitable data. Selecting a patient may bring the user to a summary sub-screen 82 on the patient condition screen 76, as depicted in FIG. 5, and/or other sub-screen, but this is not required.

The patient list portion 172 may list patients associated with a department (e.g., ICU) of a medical facility, as depicted in FIG. 26, a medical provider, a facility, and/or in one or more other suitable groupings. In some cases, a selectable list option 174 may be provided that a user may select to choose a set of patients to display in the patient list portion 172.

The patient list portion 172 may list patients in any suitable order. In some cases, the patient list screen 170 may include a selectable sort option 176 that may allow a user to select how the patients listed in the patient list portion 172 are ordered. As depicted in FIG. 26, the selectable sort option 176 indicates the patients are sorted by name. Other options for sorting the patients in the patient list portion 172 may include, but are not limited to, by age, by gender, by medical record number (MRN), by diagnosis, by medical provider (e.g., intensivist) by days in ICU, by a date of last imagery, an indication of new imagery, by changes in hemorrhage volume (e.g., ICH volume change), and/or patients may be sorted based on other sortable data. Further, in some cases, the headings indicating the patient data in an associated column may be modified and/or moved based on user preferences and/or other suitable factors.

FIGS. 27-61 depict a patient viewer screen 200 that may be configured to or may include features similar to the trend sub-screen 98 depicted in FIGS. 6-22. For example, the patient viewer screen 200 may include an image pane or portion 86 and a parameter pane or portion 66 depicting trend lines 68 of volumes for various patient parameters (e.g., ICH, IVH, edema volume, total ventricular volume, midline shift, and/or other suitable patient parameters) over a timeline 88 (e.g., a timeline of days since admission, as depicted, but other timelines are contemplated), and/or take one or more other suitable configurations.

Figure 27:
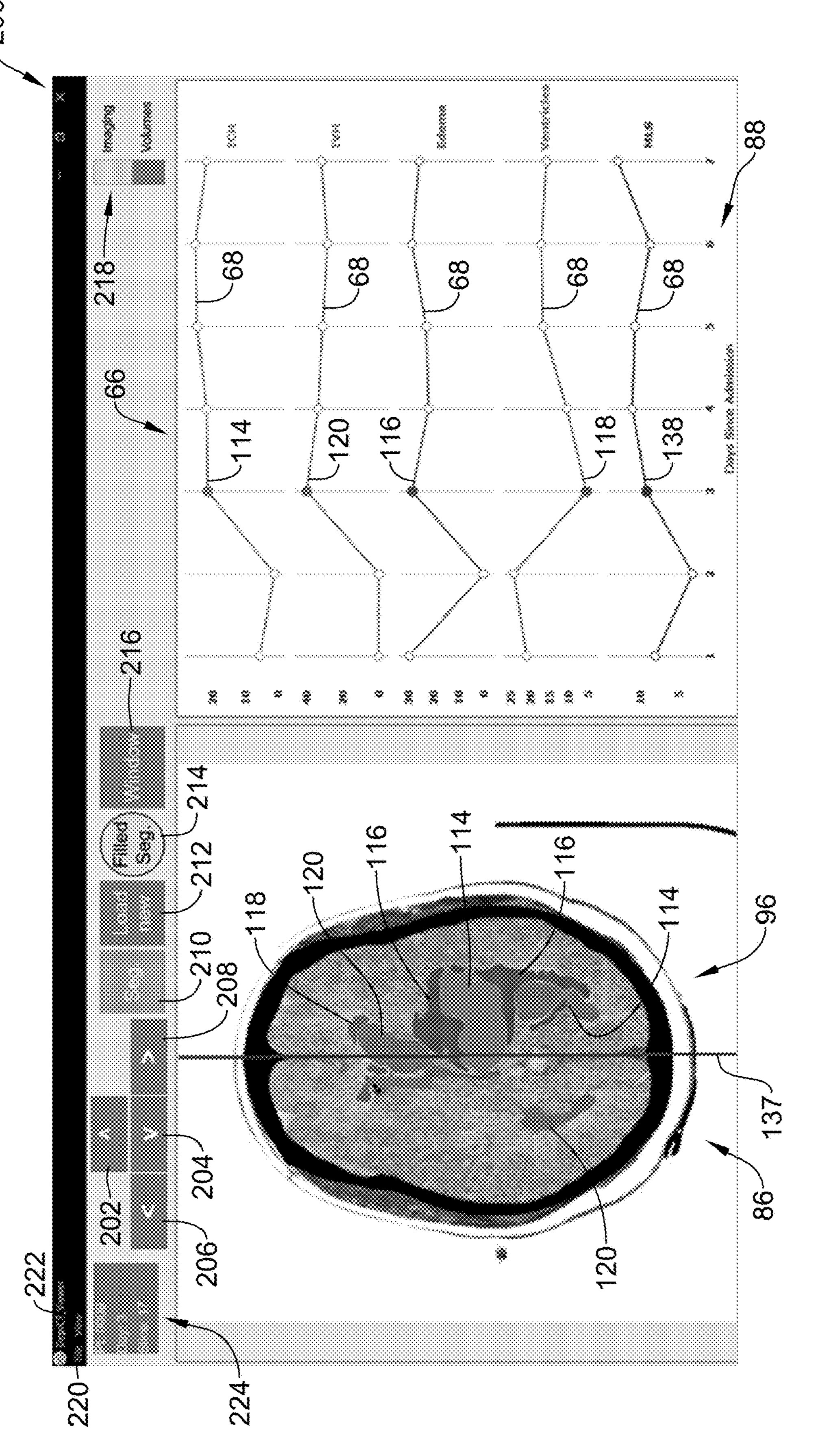
FIGS. 27-61 are schematic examples of patient viewer screens for display on a user interface and depicting information related to a patient condition.

In addition to or as an alternative to the tools and/or selectable options depicted in the screens of FIGS. 4-26, the patient viewer screen 200 may include various selectable tools or options. As depicted in FIG. 27, for example, the patient viewer screen 200 may include, among other selectable features, an up arrow 202, a down arrow 204, a back arrow 206, a forward arrow 208, a segmenting button 210, a load new patient button 212, a segment fill button 214, a windowing button 216, an image/parameter button 218, a File button 220, and a View button 222. Further, the patient viewer screen 200 may include patient and image information 224. In some cases, the patient and image information 224 may provide information identifying the patient (e.g. patient 0009 and/or other suitable information) associated with an image and/or patient parameters depicted, a day or date and/or time the depicted image was taken (e.g., day 3 and/or other suitable date and/or time at which the image was taken), a slice number of a CT scan (e.g., slice 17 and/or other suitable slice) that is being depicted, and/or other suitable information related to the patient and depicted image.

Similar to as discussed above with respect to panes of the screens, images and information on the patient viewer screens 200 may be updated in real time in response to incoming data, patient scans, and/or measurements as the data, as the patient scans, and/or measurements are received and/or updated. For example, patient scans, trend lines, and/or timelines in the patient viewer screens 200 may be updated in real time as data related to monitored parameters is received and processed by the controller 16 and/or other suitable controllers, as a user interacts with the screen, and/or in one or more other suitable instances.

In operation, a user may select the load new patient button 212 to initiate depicting an image of a patient and parameter values associated with the image of the patient. In some cases, selecting the load new patient button 212 may result in a file system popping up from which a patient, a scan of the patient (e.g., a CT scan and/or other suitable scan of the patient), a slice of a scan of the patient, and/or other suitable patient related data or file may be selected. Other techniques for loading patient data is contemplated.

Figure 28:
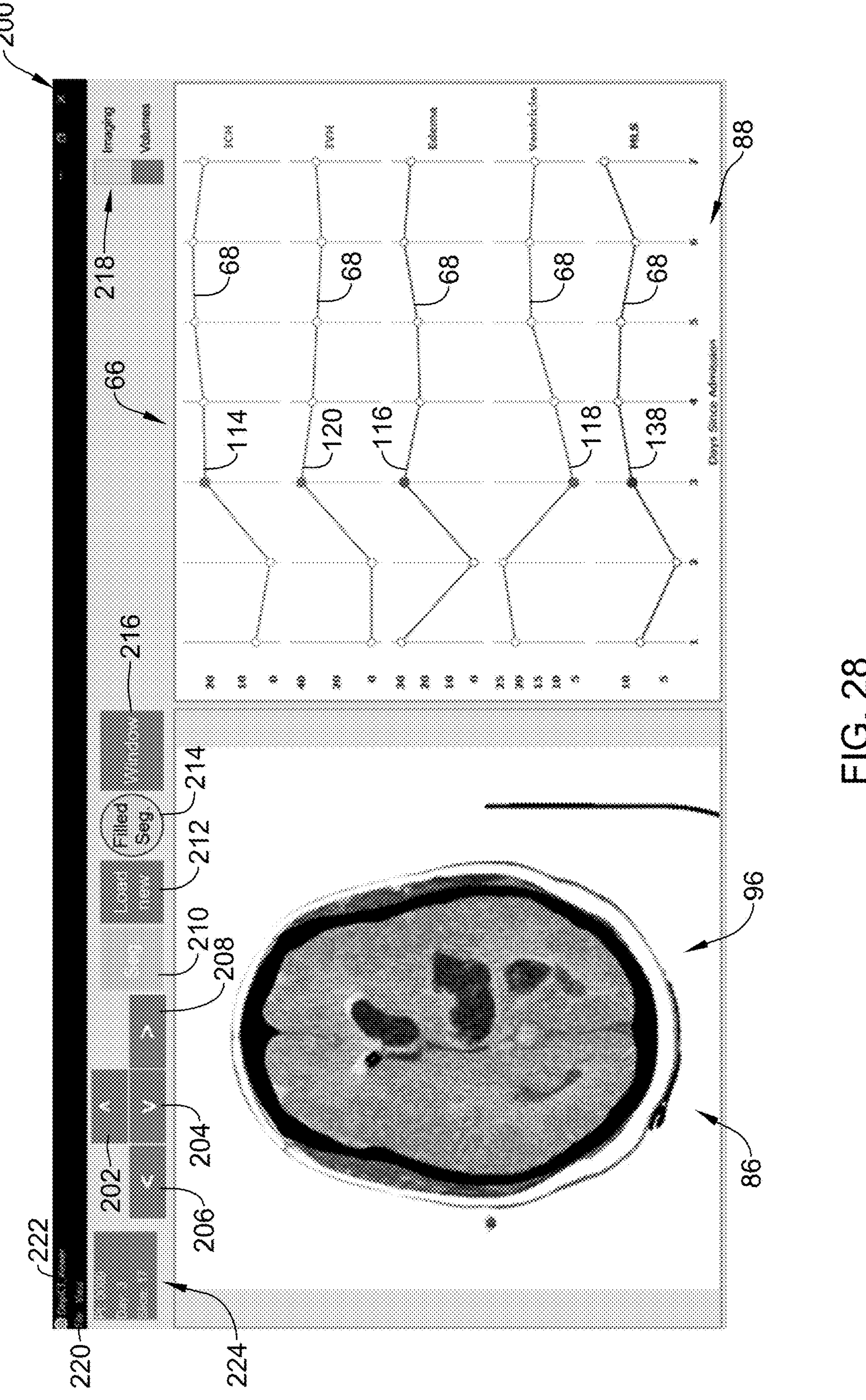

FIGS. 27 and 28 depict switching between a screen 200 with an image 96 having segmenting-identified parameters (e.g., identification of the area of the ICH volume area of the 114, the area of the edema volume 116, the area of the ventricular CSF volume 118, the area of the IVH volume 120, midline 137, and/or other suitable parameters identifiable in the image 96) depicted (e.g., as in FIG. 27) and a screen 200 having an image 96 without segmenting-identified features depicted. In the configuration of the screen 200, a user may select the segmenting button 210 to toggle between displaying the segmenting-identified parameters on the image 96 (e.g., as depicted in FIG. 27) and not displaying the segmenting-identified parameters on the image 96 (e.g., as depicted in FIG. 28). In some cases, the segmenting button 210 may change color and/or change in one or more other manners to provide feedback that the button 210 has been selected. Other suitable configurations are contemplated for switching between displaying and not displaying the segmenting on the image 96.

Figure 29:
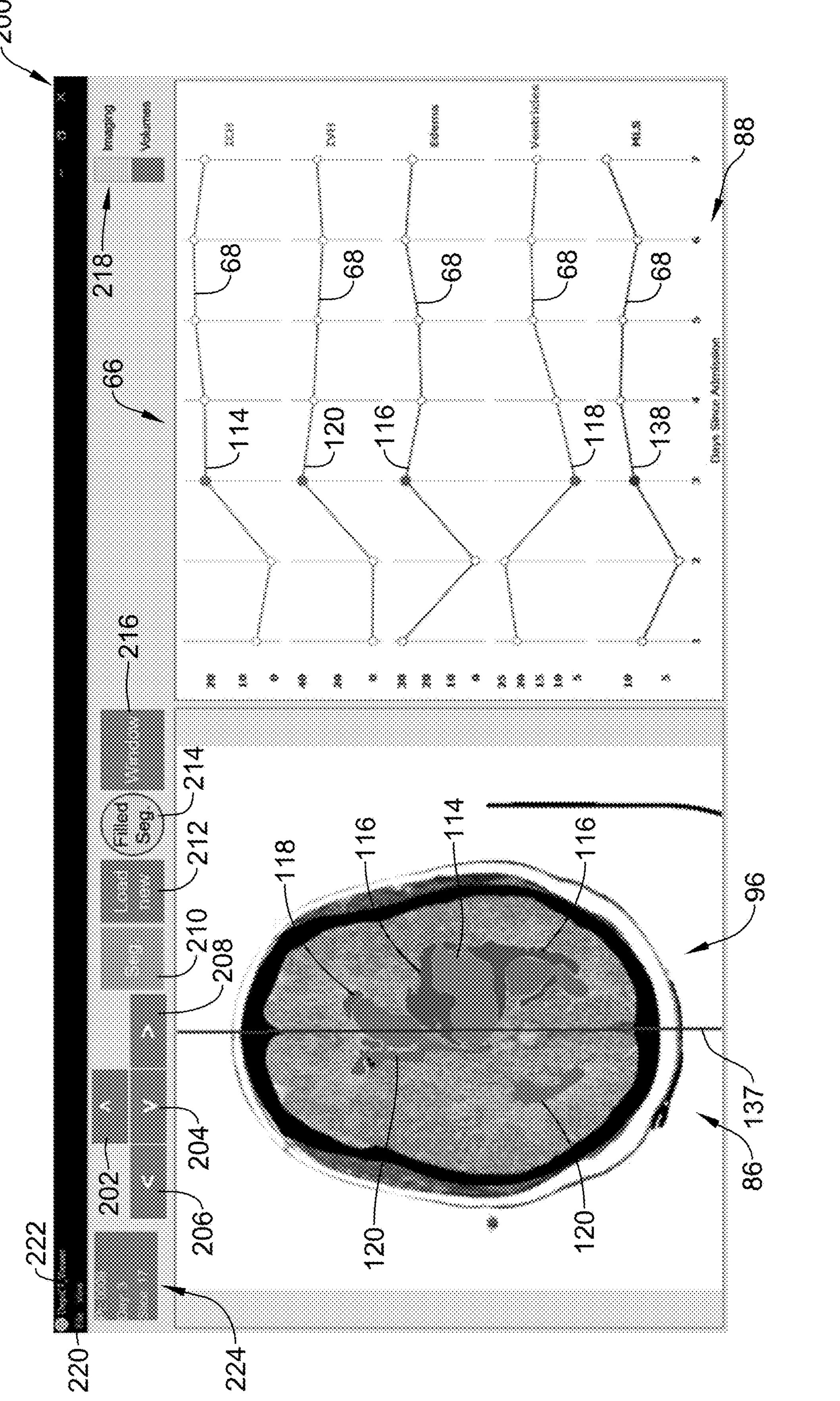
Figure 30:
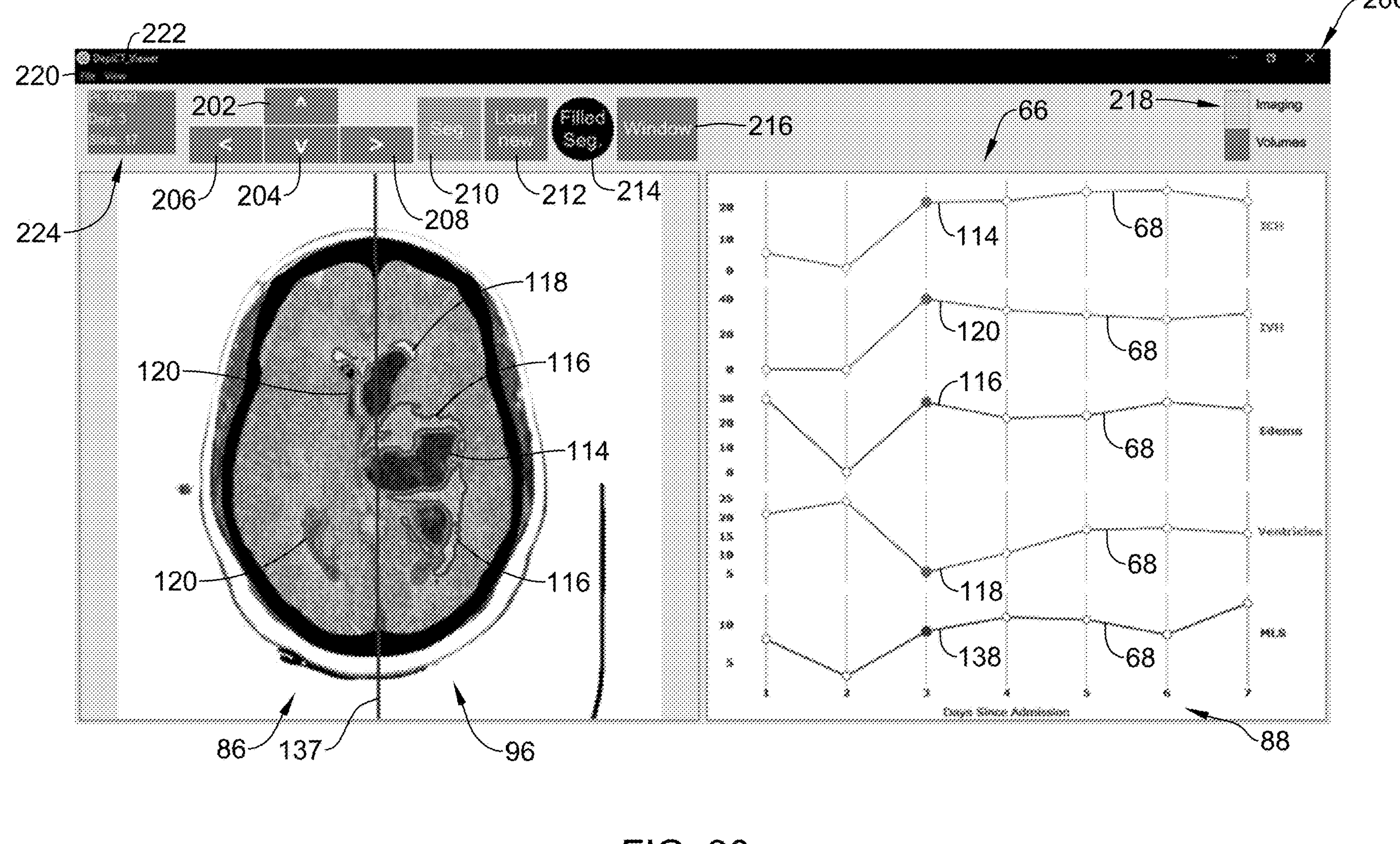

FIGS. 29 and 30 depict switching between a screen 200 with an image 96 having filled-in segmenting-identified parameters thereon and a screen 200 with an image 96 having outlined or non-filled-in segmenting-identified parameters thereon. In the configuration of the screen 200, while the segmenting button 210 is selected to cause a display of segmenting-identified parameters, a user may select the filled segmenting button 214 (e.g., labeled "Filled Seg." in FIGS. 29 and 30 or otherwise labeled) to toggle between displaying filled-in segmenting-identified parameters on the image 96 (e.g., as depicted in FIG. 29) and displaying outlined segmenting-identified parameters on the image 96 (e.g., as depicted in FIG. 30). In some cases, the filled segmenting button 214 may change color and/or change in one or more other manners to provide feedback that the button 214 has been selected. Other suitable configurations are contemplated for switching between displaying filled-in segmenting-identified parameters and outlined segmenting identified parameters on the image 96.

FIGS. 31-34 depict an illustrative configuration for changing an opacity of the segmenting-identified parameters depicted on the image 96. Other configurations for changing an opacity of the segmenting-identified parameters depicted on the image 96 are contemplated. In some cases, changing the opacity of the segmenting-identified parameters depicted on the image 96 may facilitate identifying other features in the image 96 behind the segmenting-identified parameters that are depicted.

Figure 31:
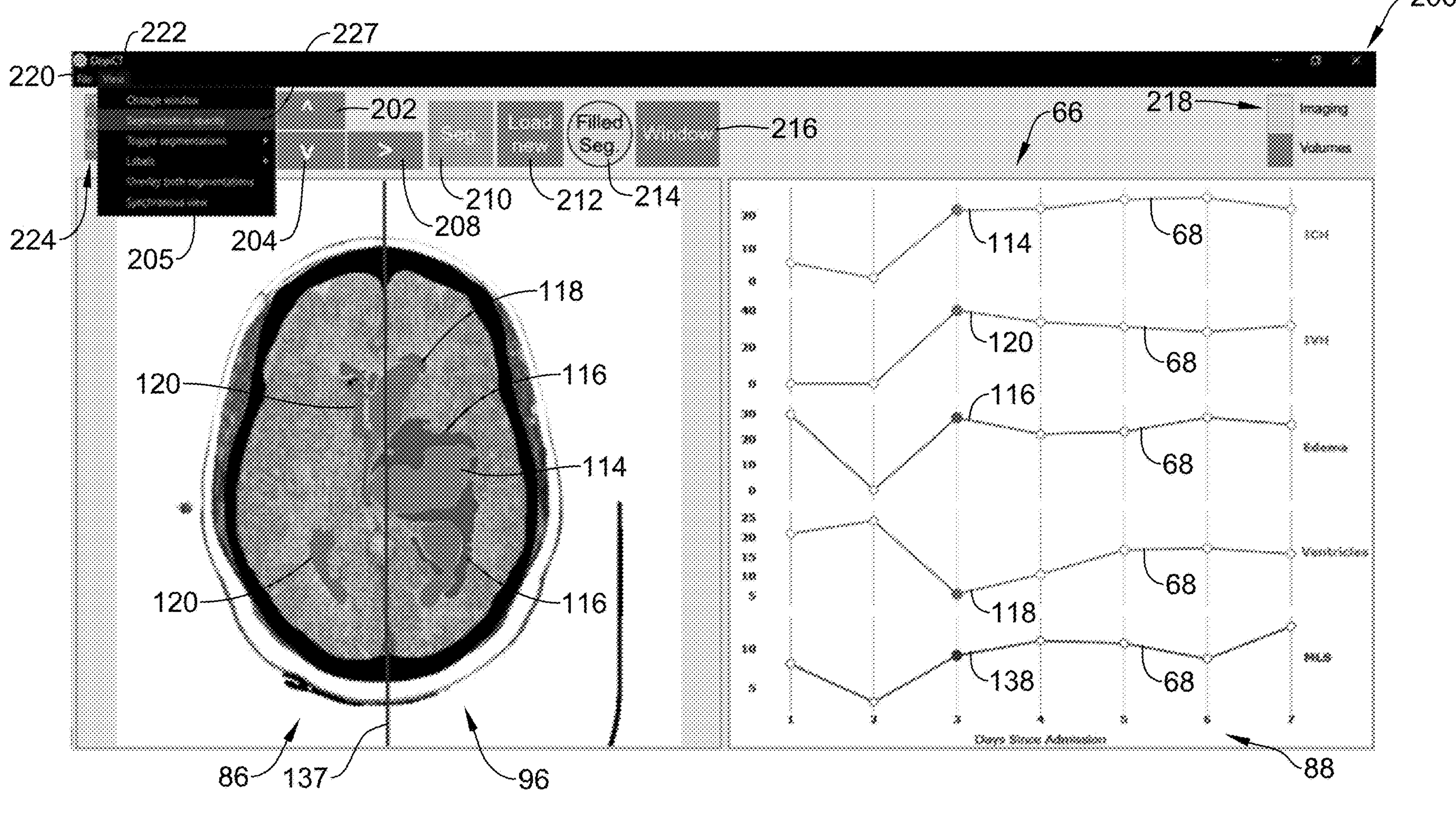

In the depicted configuration of the screen 200, a user may select the View button 222 to cause a dropdown View window 225 to appear on the screen 200. The dropdown View window 225 may include one or more selectable options including, but not limited to "Change Window", "Segmentation Opacity", "Toggle Segmentations", "Labels", "Overlay Both Segmentations", etc. A user may select the Segmentation Opacity option 227 by clicking on the option 227, touching the option 227, or otherwise selecting the option 227, as depicted in FIG. 31.

Figure 32:
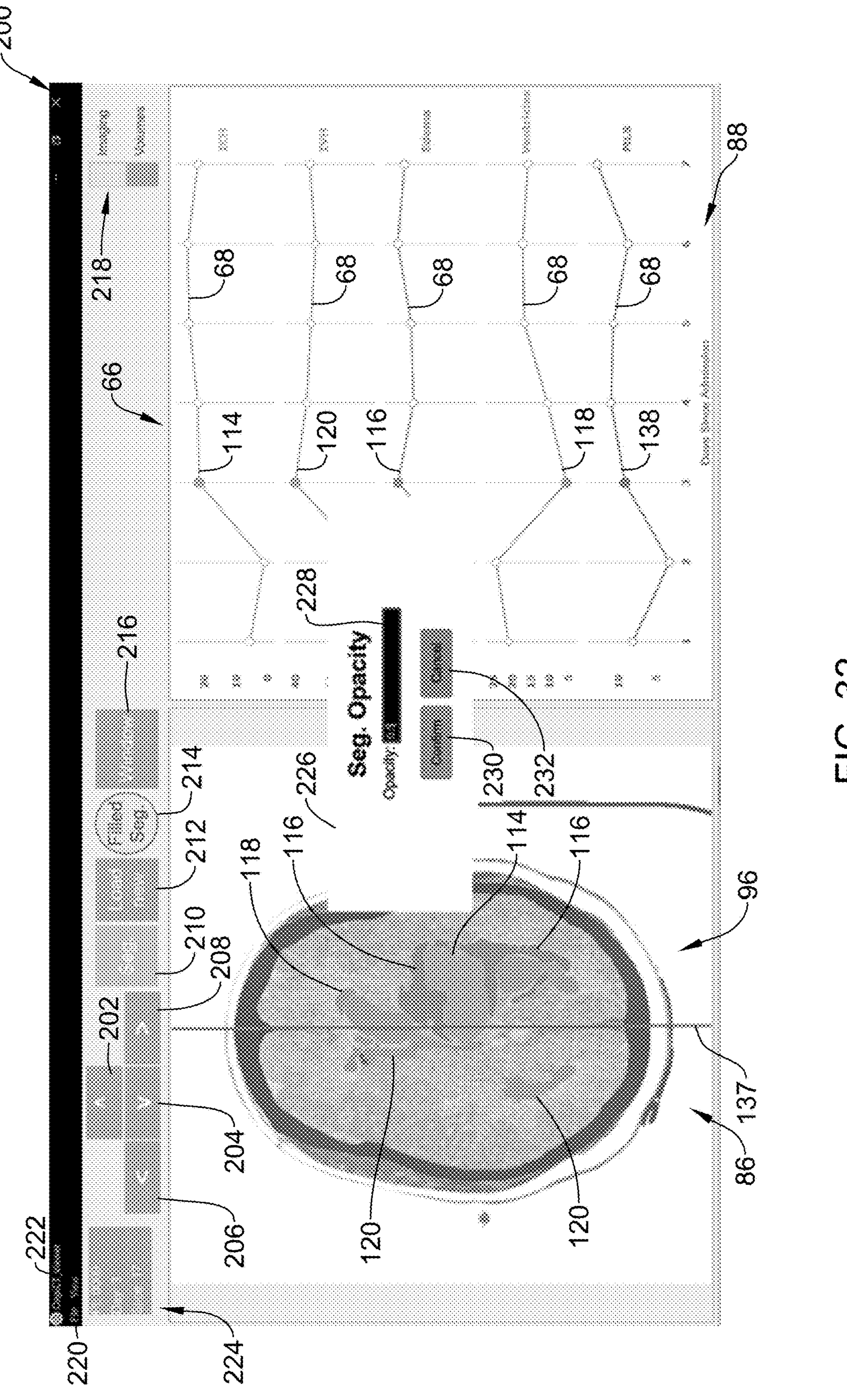

Once the Segmentation Opacity option 227 has been selected, a segmentation opacity window 226 (e.g., labeled Seg. Opacity") may pop-up, as depicted in FIG. 32. A user may enter an opacity value in an opacity value box 228 of the segmentation opacity window 226, where the entered value is proportional to an opaqueness of the depicted segmenting-identified parameters on the image 96. For example, a user may enter a number between zero (0) and one (1) (other suitable ranges including percentages, etc. are contemplated), where zero (0) may result in the segmenting-identified parameter not being viewable on the image 96 because it is completely transparent and one (1) may result in the segmenting-identified parameter being completely opaque. Once a desired opacity value (e.g., 0.5 in FIG. 32) is entered in the opacity value box 228, a user may select the Confirm button 230 to move forward with the entered opacity value or the Cancel button 232 to move forward with a previously selected opacity or a default opacity. Although the opacity selection technique depicted in FIGS. 31 and 32 includes entering the opacity value, other configurations for adjusting the opacity of the depicted segmenting-identified parameters displayed may utilize, among other suitable additional or alternative features, a slide bar, arrow keys, swiping, pinching, etc.

Figure 33:
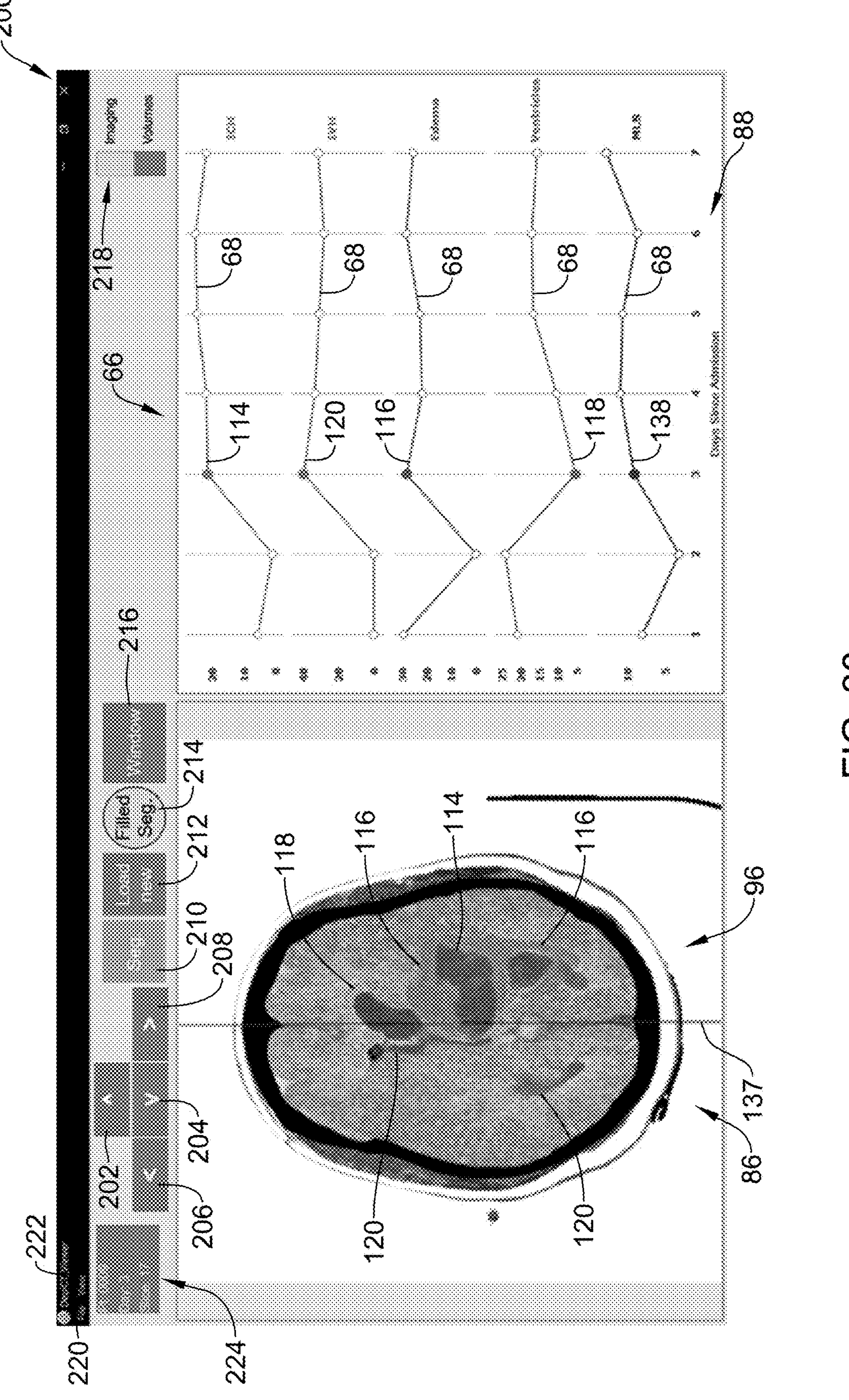
Figure 34:
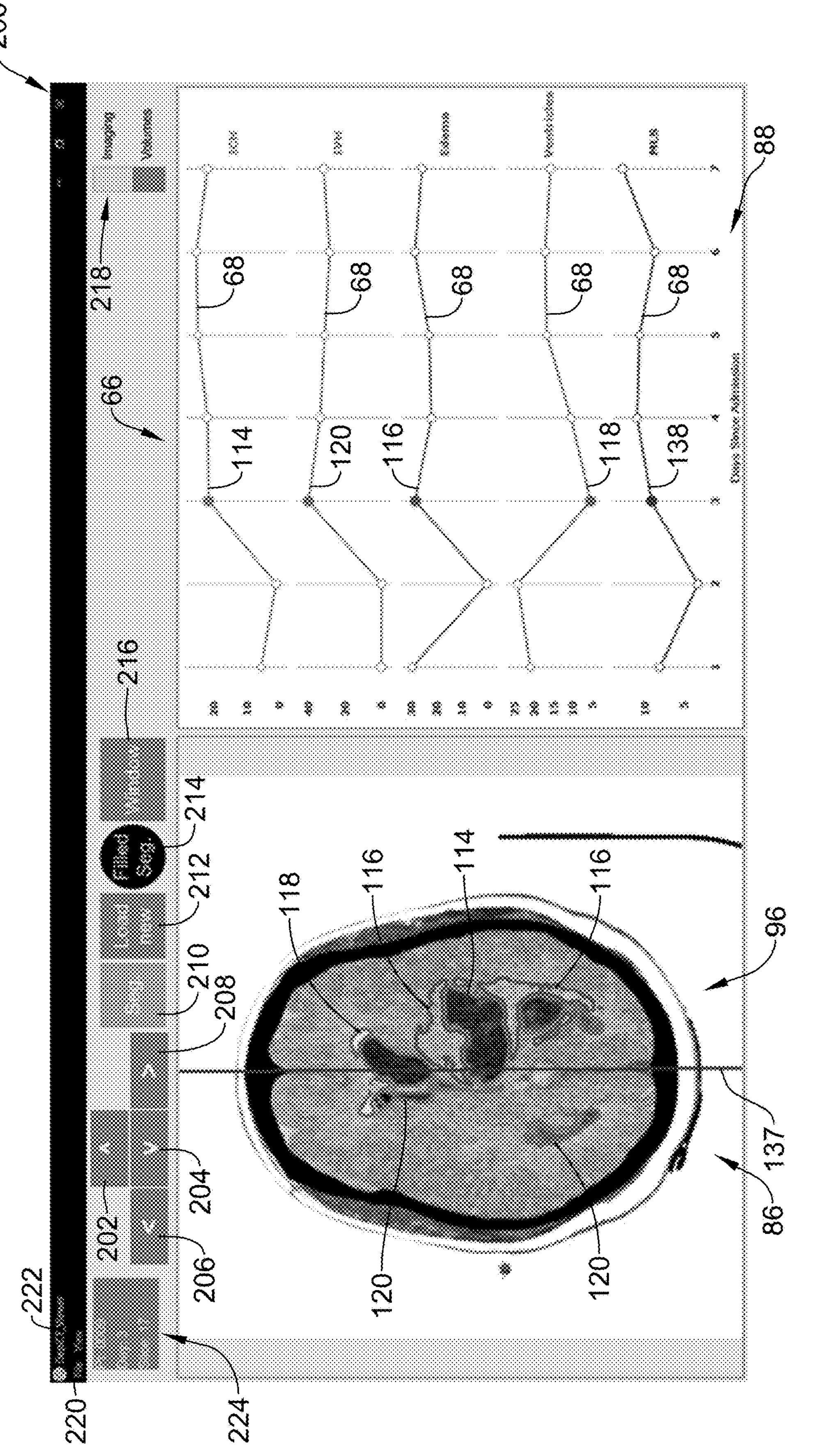

FIG. 33 and FIG. 34 depict the segmenting-identified parameters on the image 96 with a selected opacity value (e.g., an opacity value of 0.5 or other suitable value). FIG. 33 depicts filled-in segmenting-identified parameters at an opacity value of 0.5 on the image 96. FIG. 34 depicts outlined segmenting-identified parameters at an opacity value of 0.5 on the image 96. As depicted in FIGS. 33 and 34, it may be possible to view the patient's brain and/or other scanned features through the at least partially opaque segmenting-identified parameters on the image 96.

Figure 35:
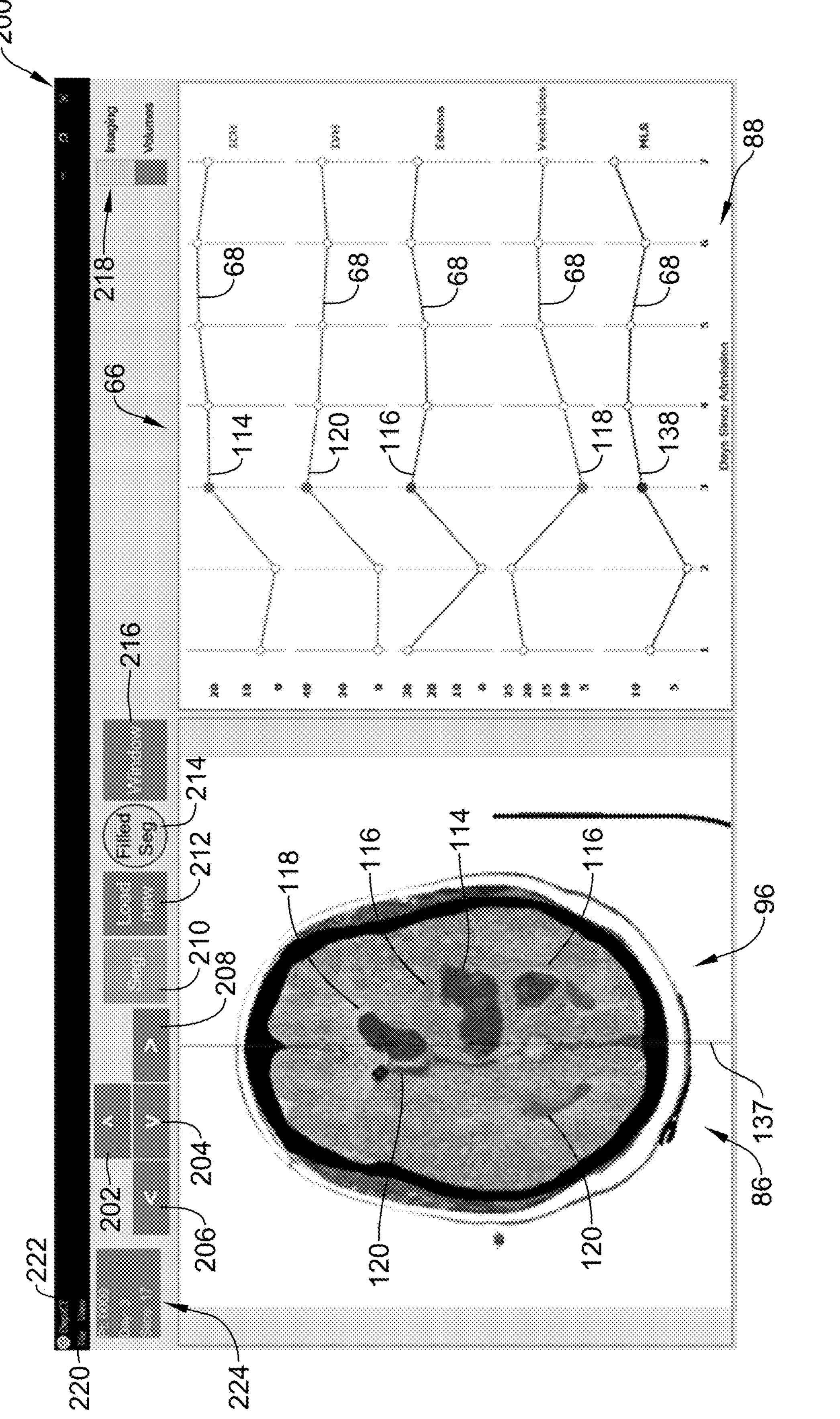

FIGS. 35-38 depict an illustrative configuration for identifying segmenting-identified parameters on the image 96 using a filled-in and outlined approach. In some cases, as depicted in FIG. 35, filled-in segmenting-identified parameters may be depicted on the image 96 and outlining may be added thereto. Alternatively, outlined segmenting-identified parameters may be depicted on the image 96 and the spaces within the outlines may be filled-in with an appropriate color or shading. Other suitable configurations for depicting segmenting-identified parameters on the image 96 using filled-in and/or outlined representations are contemplated.

In one example of identifying segmenting-identified parameters on the image 96 using a filled-in and outlined approach as depicted in FIGS. 35-38, a user may start with the screen 200 depicting the image 96 having filled-in segmenting-identified parameters thereon. The filled-in segmenting-identified parameters may be at least partially transparent, as shown in FIG. 35, or entirely opaque.

Figure 36:
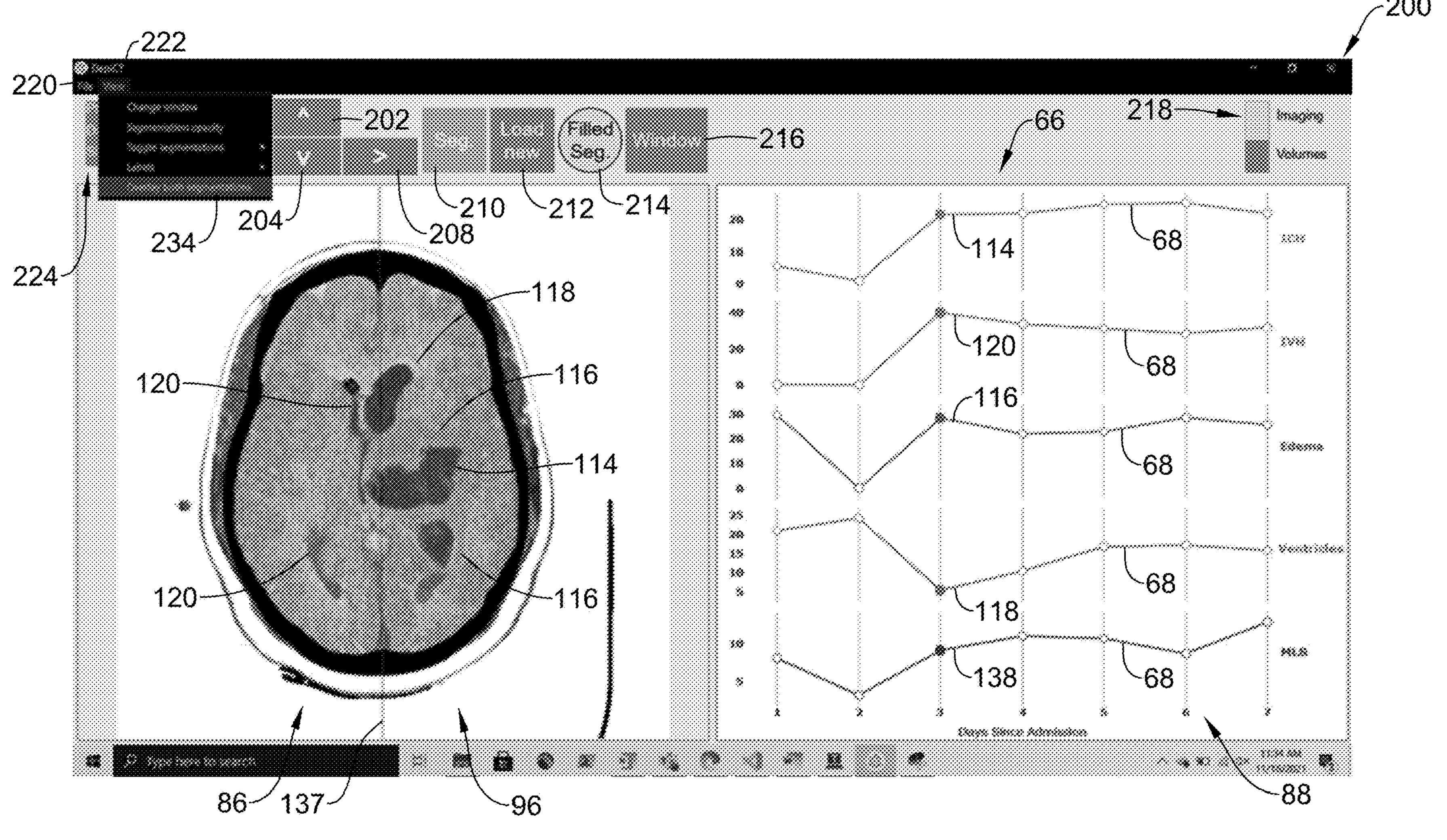

In the configuration of the screen 200, a user may select the View button 222 to cause a dropdown View window 225 to appear on the screen 200, as depicted in FIG. 36. The dropdown View window 225 may include one or more selectable options including, but not limited to "Change Window", "Segmentation Opacity", "Toggle Segmentations", "Labels", "Overlay Both Segmentations", etc. A user may select the Overlay Both Segmentations option 234 by clicking on the option 234, touching the option 234, or otherwise selecting the option 234, as depicted in FIG. 36.

Figure 37:
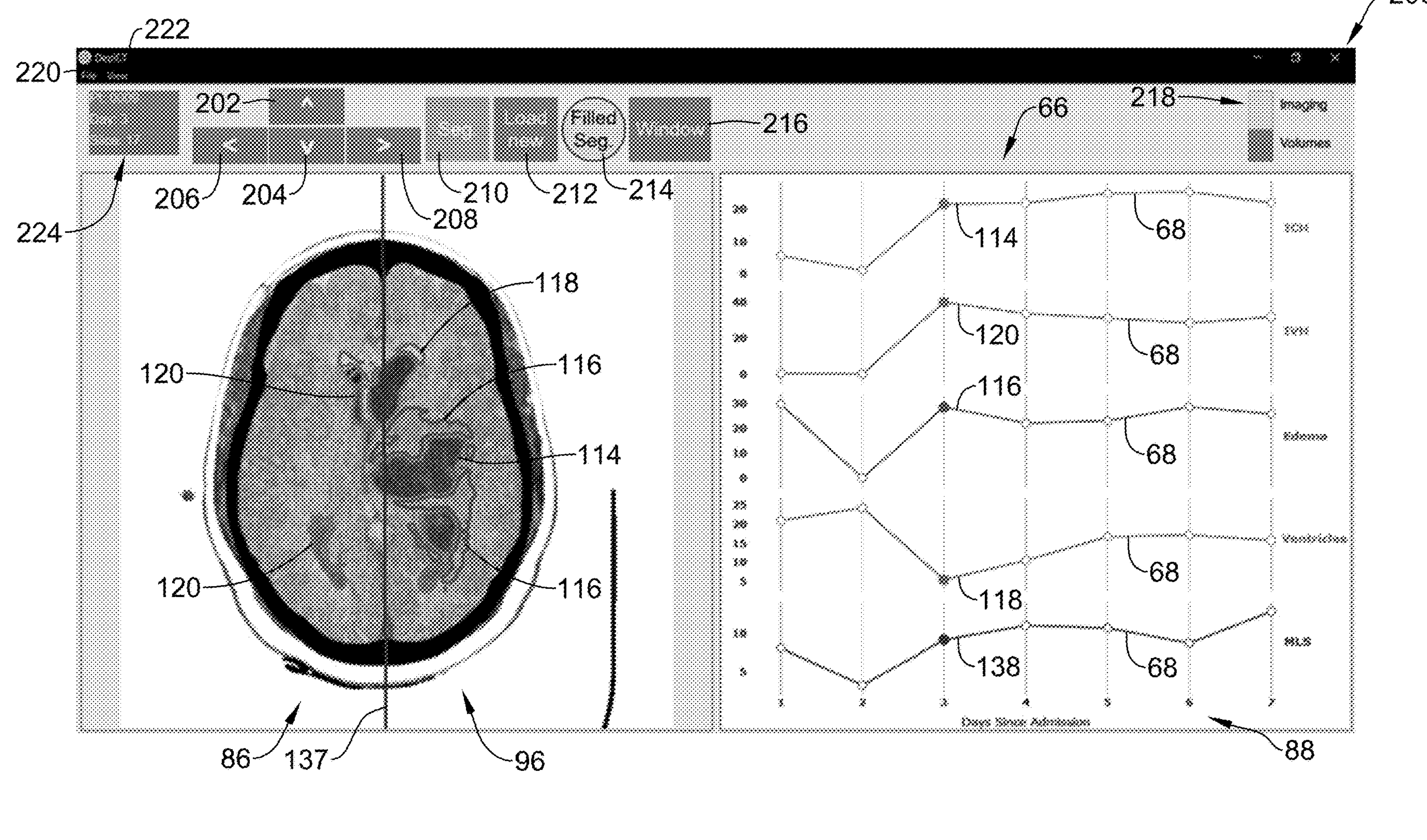
Figure 38:
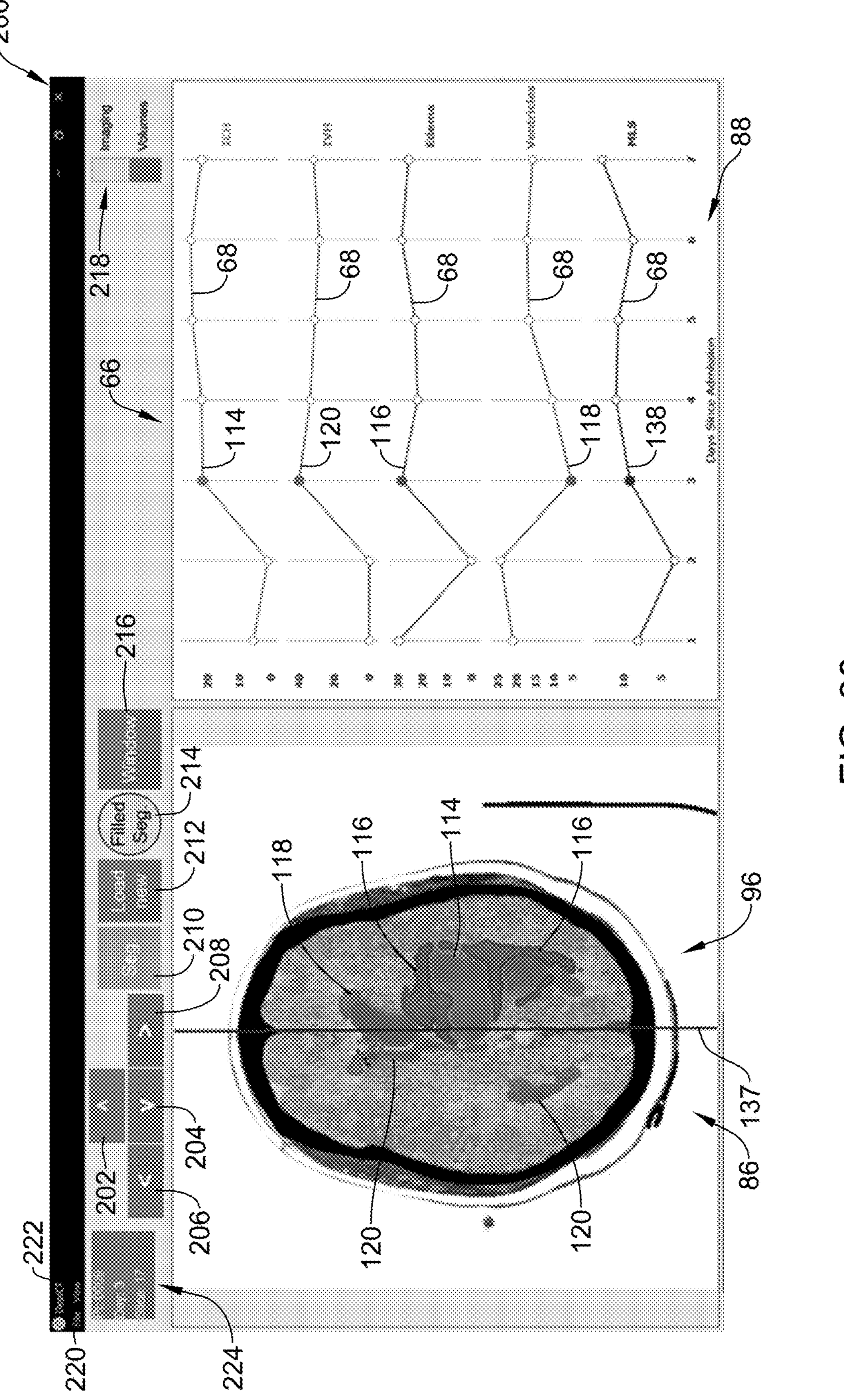

Once the Overlay Both Segmentations option 234 has been selected, an outline may be provided around the filled-in segmenting-identified parameters on the image 96, as depicted in FIG. 37. In some cases, a user may desire to change the opacity of the segmenting-identified parameters on the image 96 and may be able to change the opacity of the depicted parameters using the technique described herein with respect to FIGS. 31-34 and/or using other suitable techniques. FIG. 38 depicts an example screen 200 showing the segmenting-identified parameters in both a filled-in and outlined format, where the filled-in portion is opaquer than what is depicted in FIG. 37. Adjusting an opaqueness of the depicted parameters when the parameters are outlined may facilitate viewing the image 96 and clearly identifying areas and/or volumes of relevant parameters.

Figure 39:
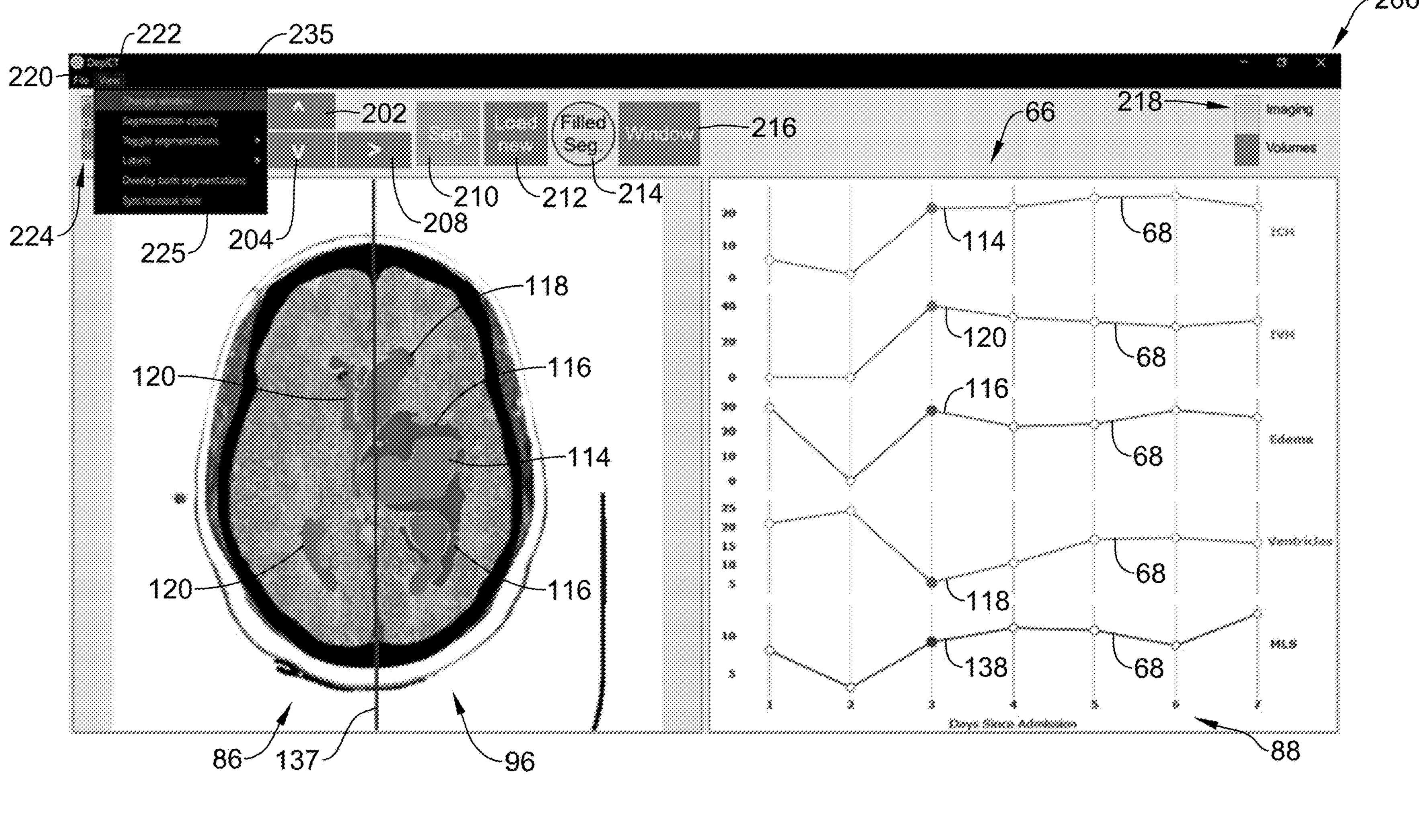
Figure 40:
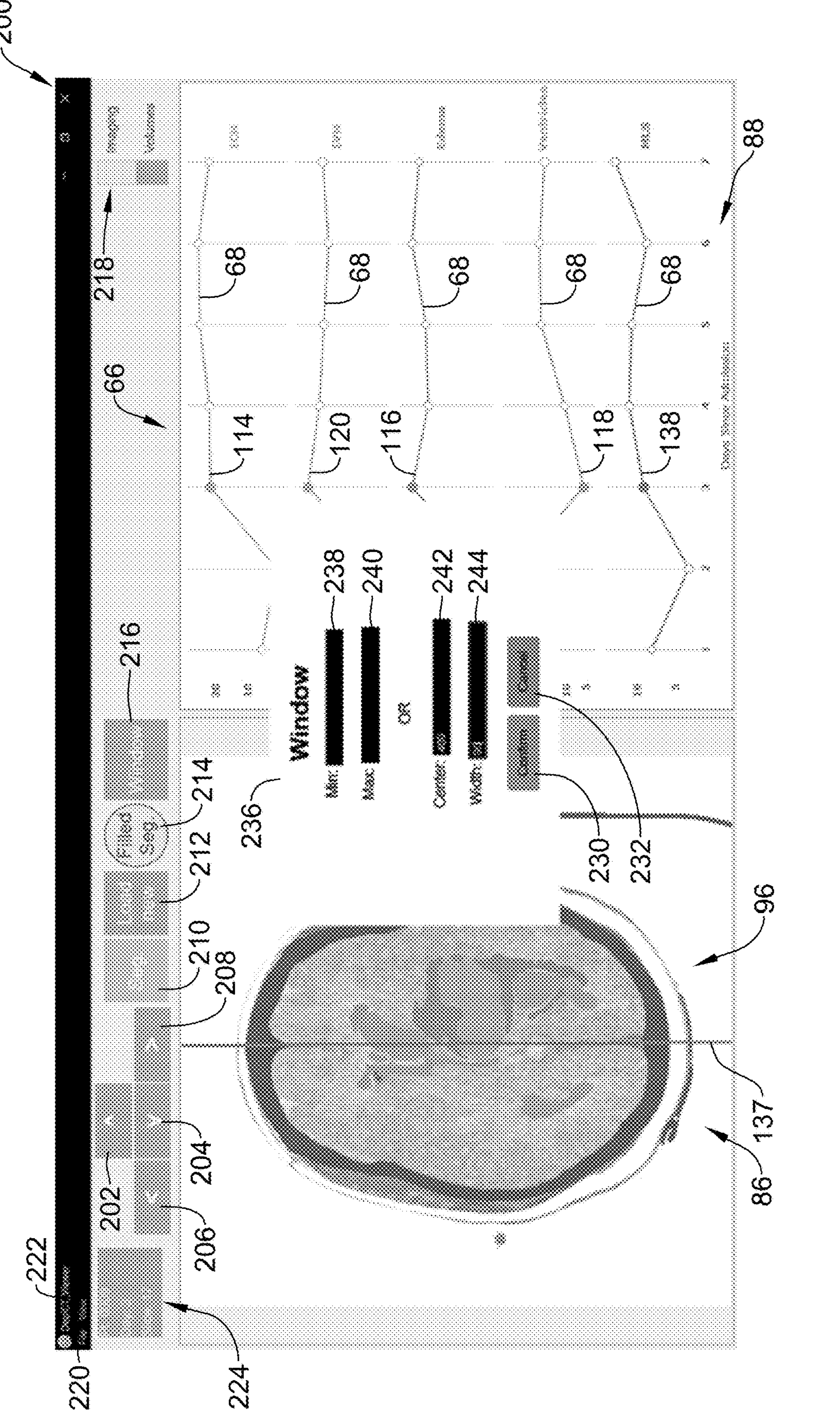
Figure 41:
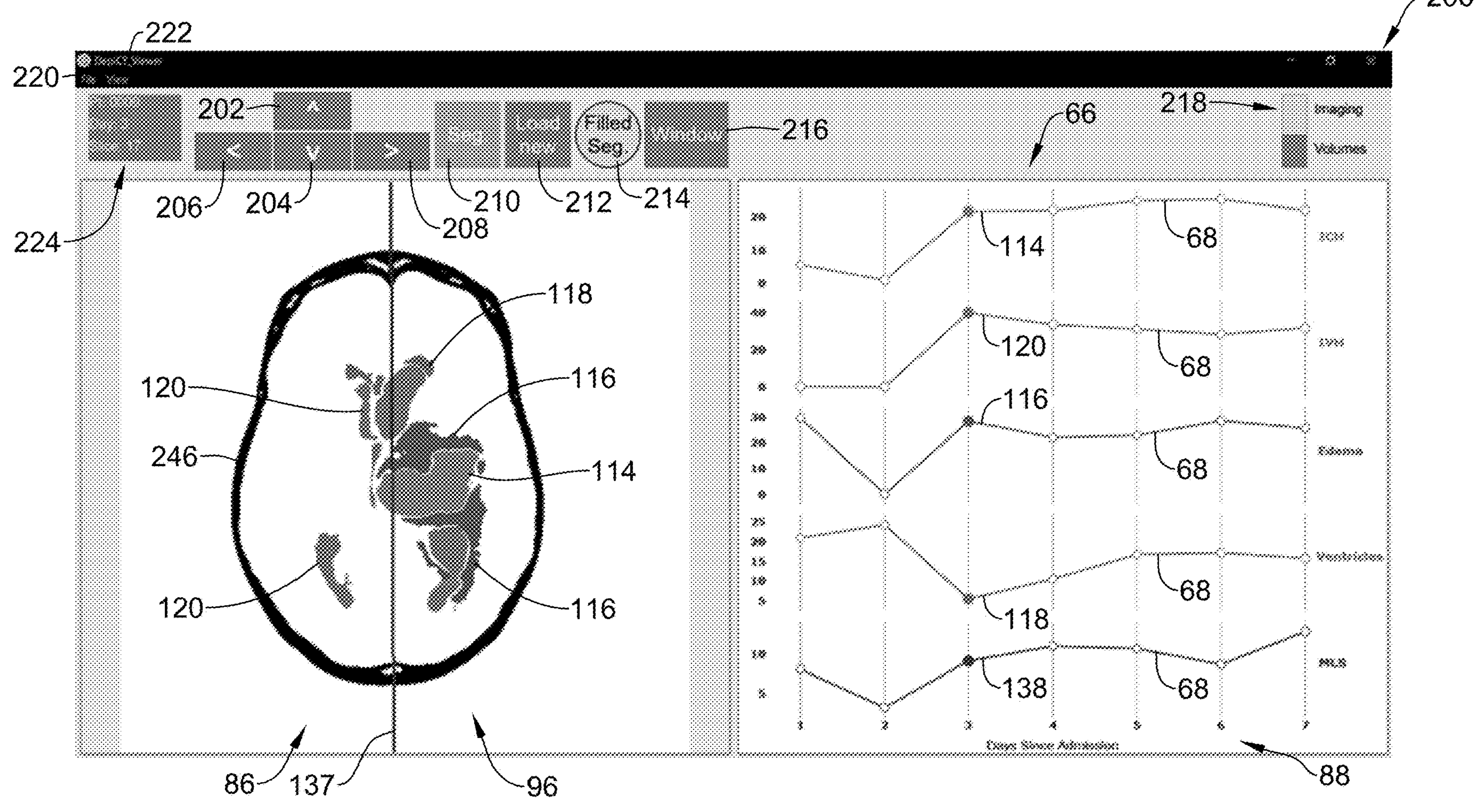

FIGS. 39-41 depict an illustrative configuration for windowing the image 96. Windowing is a process in which a greyscale component of an image (e.g., a CT image or other suitable image) may be manipulated via CT to change an appearance of the image and highlight particular structures. In some cases, a brightness of an image may be adjusted via a window level and a contrast may be adjusted via window width. Such windowing, when combined with depicting the segmenting-identified parameters on the image 96 may facilitate determining positions of and/or other information related to the depicted parameters relative to structures of the patient in the image 96.

A window width may be a measure of a range of CT numbers that an image contains. For example, a wider widow width may display a wider range of CT numbers. CT numbers in an image that are above the range will be white and CT numbers in the image that are below the range will be black.

A window width may be given a window center, which is the midpoint of the range of CT numbers displayed. When the window center is lower, the image will be brighter than when the window center is higher. The window width may be set by a user providing a maximum CT number and a minimum CT number, providing a window center and a window width, and/or providing other suitable information.

In the configuration of the screen 200, a user may select the View button 222 to cause a dropdown View window 225 to appear on the screen 200. The dropdown View window 225 may include one or more selectable options including, but not limited to "Change Window", "Segmentation Opacity", "Toggle Segmentations", "Labels", "Overlay Both Segmentations", etc. A user may select the Change Window option 235 by clicking on the option 235, touching the option 235, or otherwise selecting the option 235, as depicted in FIG. 39. Alternatively, a user may select the Window button 216 on the screen 200 to initiate setting a window for the image 96.

Once the Change Window option 235 or the Window button 216 has been selected, a Windowing window 236 (e.g., labeled "Window") may pop-up, as depicted in FIG. 40. Among other suitable options, the Windowing window 236 may allow a user to choose between entering a minimum CT number value in a Minimum box 238 and a maximum CT number in a Maximum box 240 or entering a window center in a Center box 242 and a window width in a Width box 244. As depicted in FIG. 40, a window center at CT number 400 is provided and a window width of 90 is provided, which results in a window extending from CT number 355 to CT number 445. Once a desired window is entered, a user may select the Confirm button 230 to move forward with the entered window or the Cancel button 232 to move forward with a previously selected window or a default window. Although the window selection configuration depicted in FIG. 40 includes entering values for the window, other configurations for adjusting the window of the image 96 may utilize, among other suitable additional or alternative features, a slide bar, arrow keys, swiping, pinching, etc.

FIG. 41 depicts the segmenting-identified parameters on the image 96 with a selected window having a window center at a CT number of 400 and a window width of 90. As depicted in FIG. 41, it may be possible to view parameters identified from the image 96 relative to a clear depiction of the patient's skull structure 246 and/or relative to other features in the image 96 having particular CT number within the set window.

Figure 42:
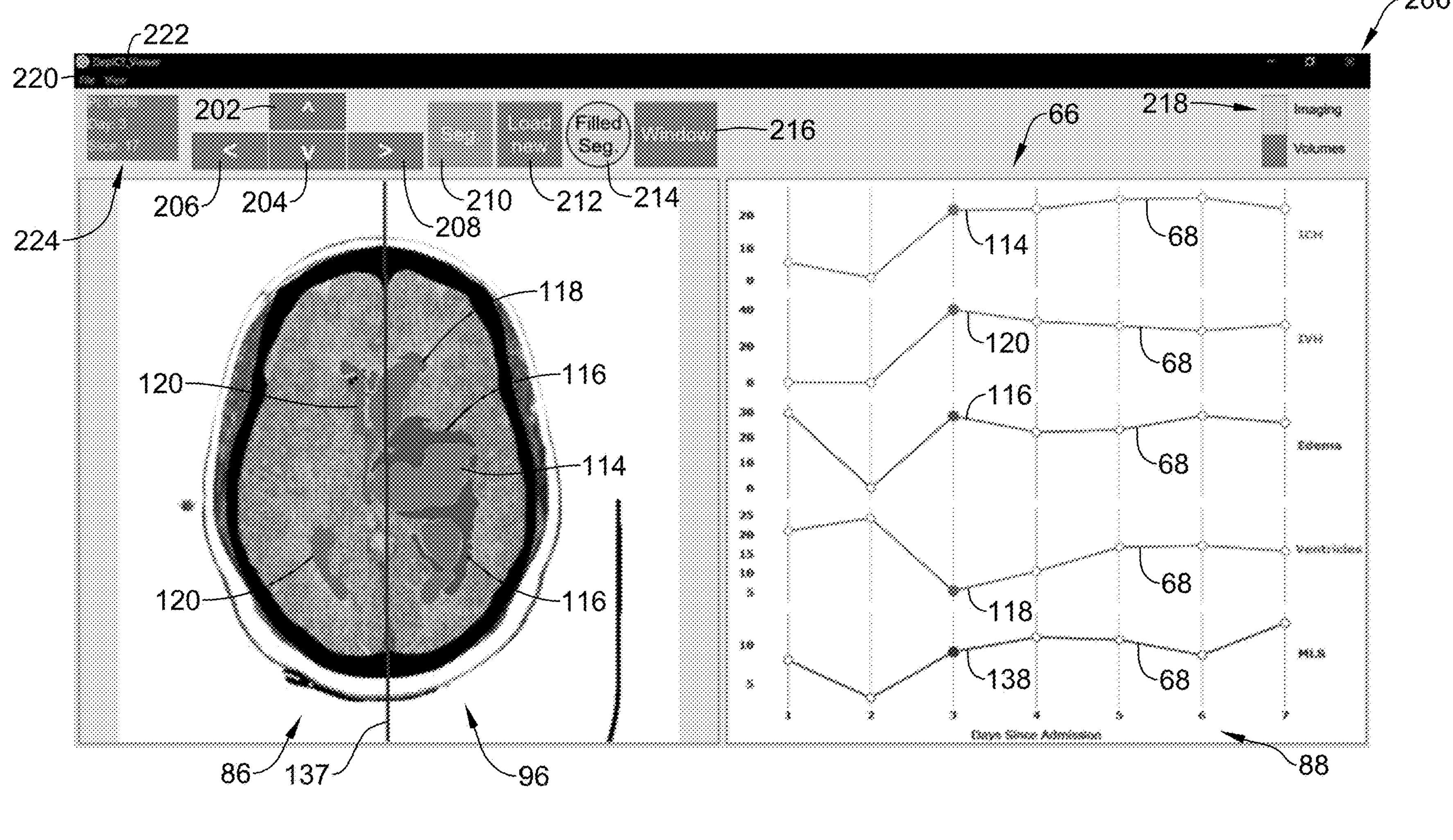
Figure 43:
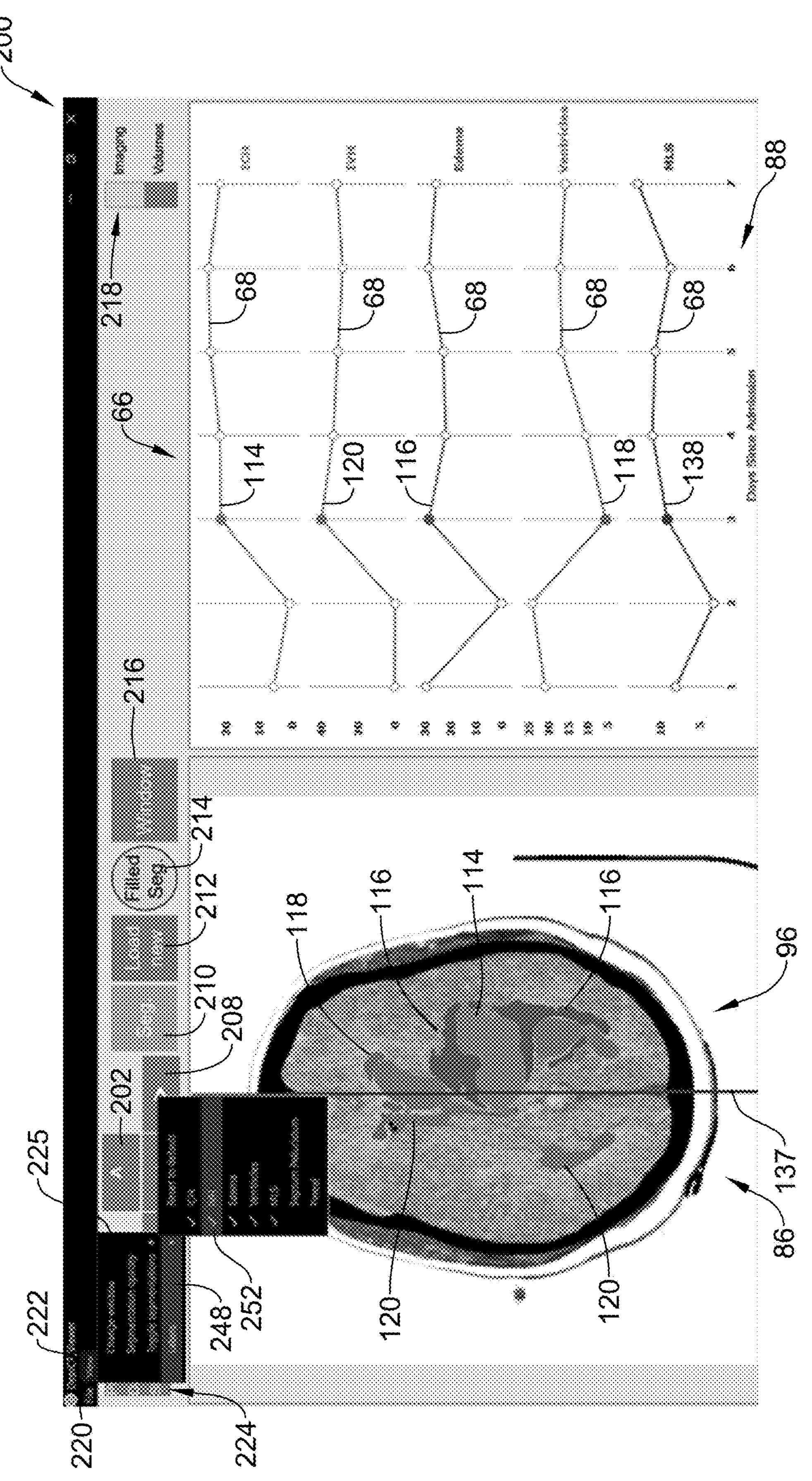
Figure 44:
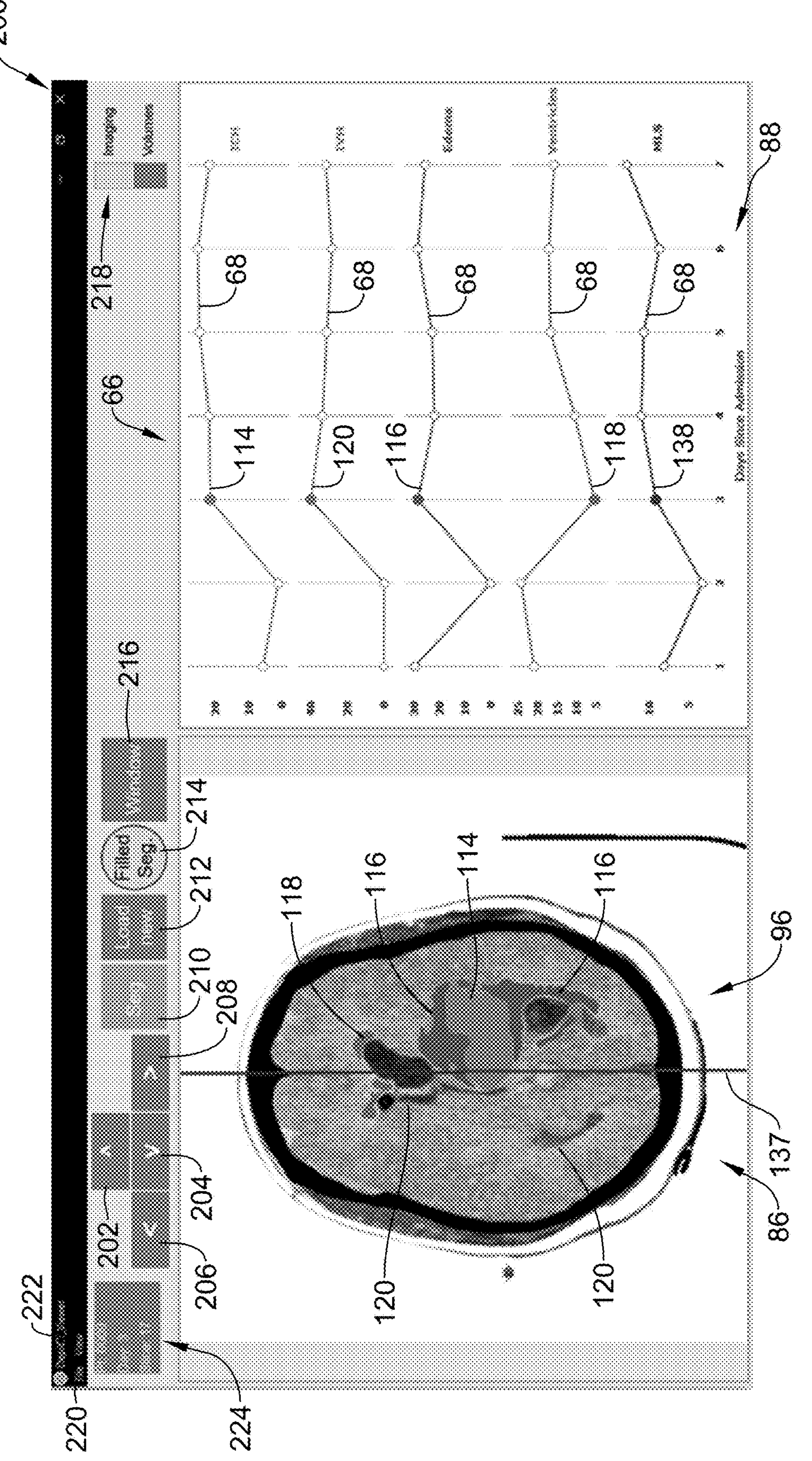

FIGS. 42-44 depict an illustrative configuration for selecting which segmenting-identified parameters are displayed on the image 96. Although fewer or more parameters may be depicted on the image 96 of the screen 200, the area of the ICH volume 114, the area of the edema volume 116, the area of the ventricular CSF volume 118, the area of the IVH volume 120 and the midline 137 may be displayed on the image 96.

In the configuration of the screen 200, a user may select the View button 222 to cause a dropdown View window 225 to appear on the screen 200, as depicted in FIG. 43. The dropdown View window 225 may include one or more selectable options including, but not limited to "Change Window", "Segmentation Opacity", "Toggle Segmentations", "Labels", "Overlay Both Segmentations", etc. A user may select the Labels option 248 by clicking on the option 248, touching the option 248, or otherwise selecting the option 248, as depicted in FIG. 43.

In response to selecting the Labels option 248, a Label dropdown window 250 may be provided on the screen. The Label dropdown window 250 may include one or more selectable options including, but not limited to "Reset to Default", "ICH", "IVH", "Edema", "Ventricles", "MLS", "Septum Pellucidum", "Pineal", etc. A checkmark and/or other suitable marking may be provided next to parameters that are currently selected to be depicted on the image 96 (e.g., ICH, IVH, Edema, Ventricles, MLS, as depicted in FIG. 43).

When a user wants to remove one of the parameters from being depicted on the image 96 and/or add a parameter to be depicted on the image 96, a user may select the parameter to cause the change in parameters depicted on the image 96. A selection of the "Reset to Default" option may result in a default set of parameters being depicted on the image 96.

In an example shown in FIGS. 43 and 44, the area of the ICH volume 114, the area of the edema volume 116, the area of the ventricular CSF volume 118, the area of the IVH volume 120 and the midline 137 are displayed on the image 96 and a user may select the "IVH" option and/or other suitable options from the Labels window 250 to remove a depiction of the IVH parameter and/or other suitable parameters from the image 96. FIG. 44 depicts the image 96 without the area of the IVH volume 120 depicted, but with other parameters depicted (e.g., the area of the ICH volume 114, the area of the edema volume 116, the area of the ventricular CSF volume 118, and the midline 137), which may be in response to the selection of the IVH option in FIG. 43.

A CT scan image may be a three-dimensional image formed from several two-dimensional scans or slices, where the slices may be horizontal slices of a three-dimensional portion of a patient and numbered from bottom to top or top to bottom. For example, the image 96 depicted in the Figures is a two-dimensional slice of a CT scan.

FIGS. 45-48 depict switching the image 96 between slices of a CT scan (e.g., a scan on Day 1) for a selected patient (e.g., patient 0009) using up and down arrow buttons 202, 204. Switching between slices of the CT scan may facilitate determining a vertical spread of an identified parameter in the image 96. Although arrows are depicted and described for moving between slices of a CT scan, other techniques for moving between slices of a CT scan are contemplated including, but not limited to, selecting selectable images 97 from a selectable images pane 100, as described herein, a scroll bar, swiping, and/or other suitable techniques for switching between available images 96.

Figure 45:
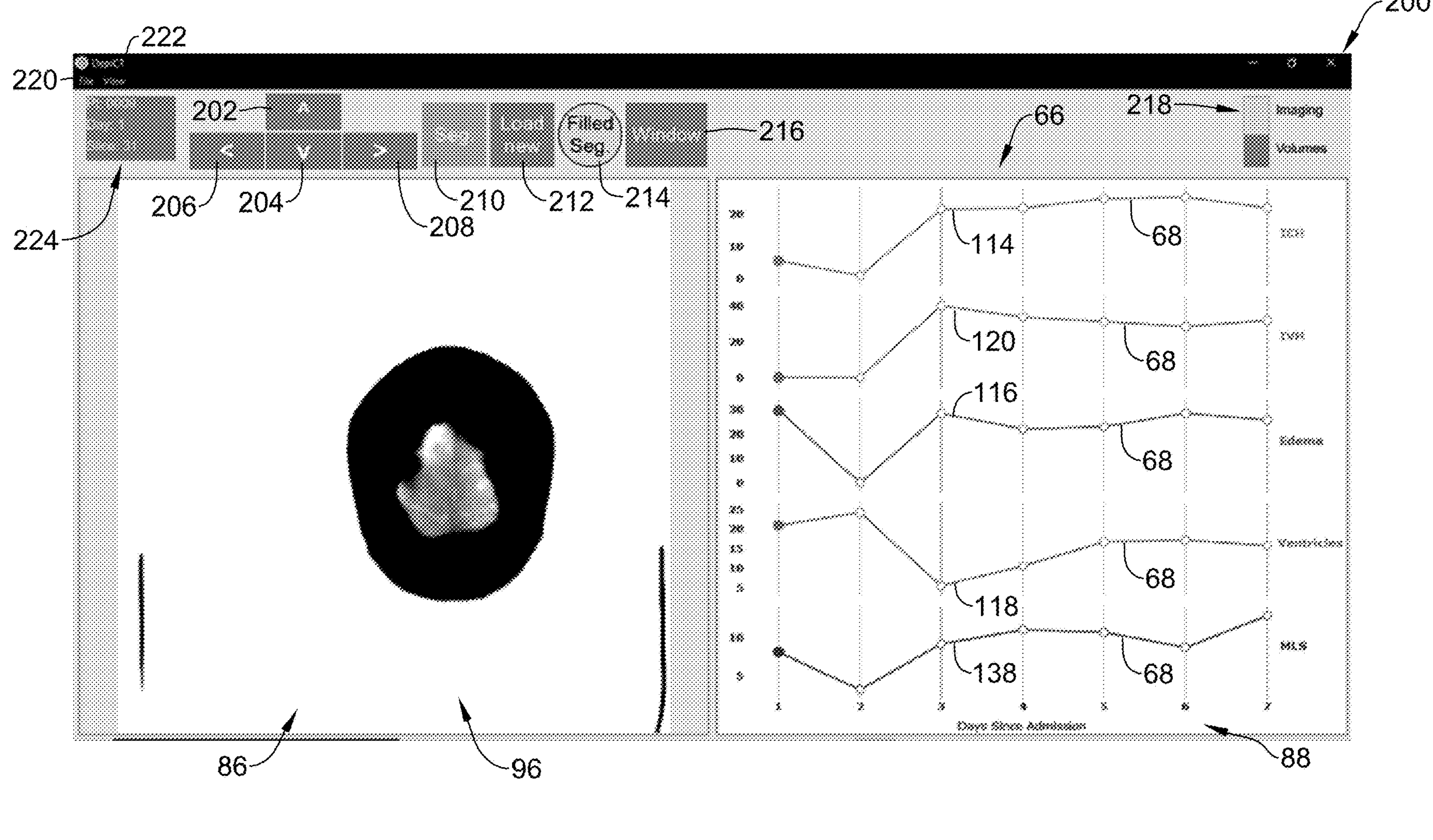
Figure 46:
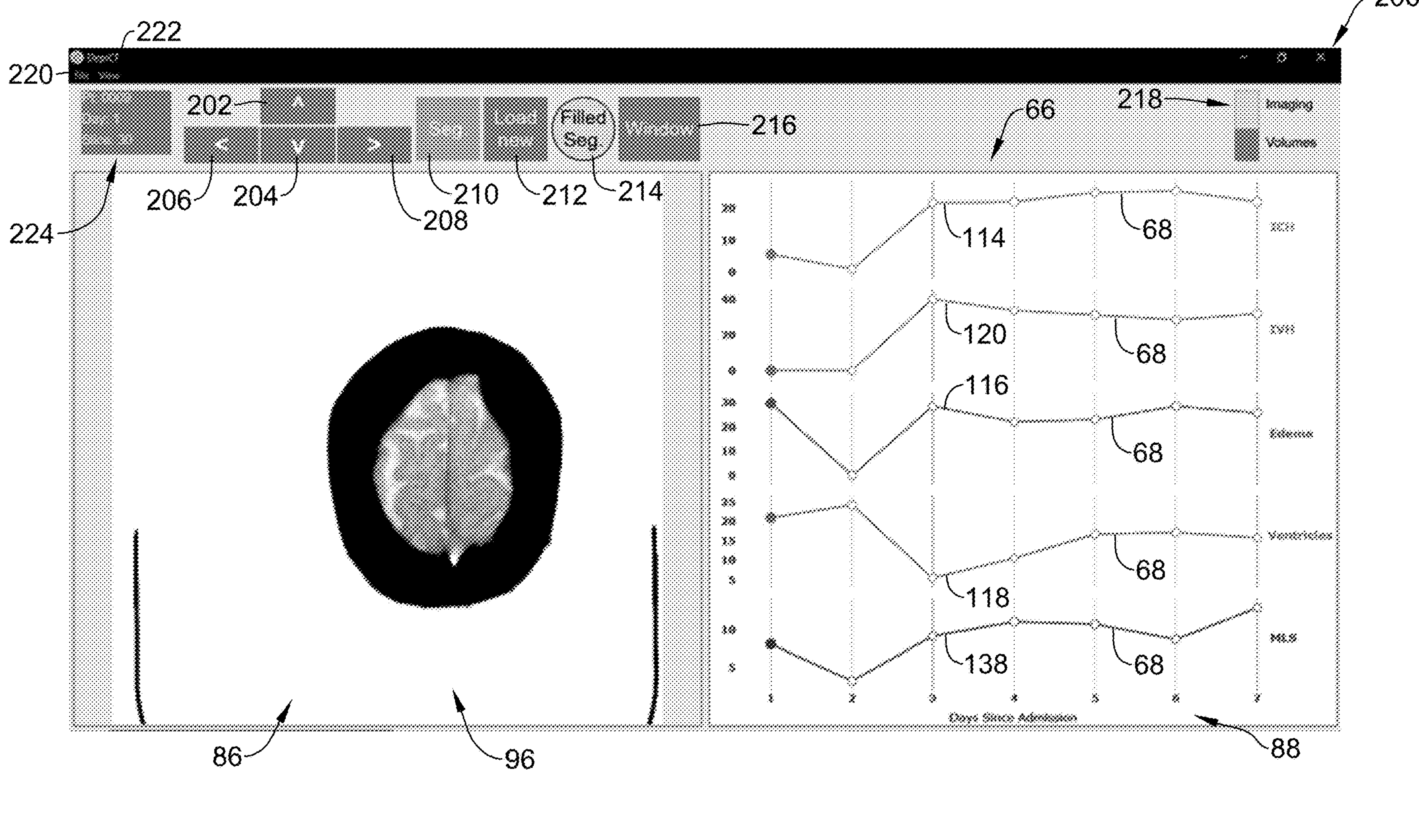

FIG. 45 depicts slice 31 of a CT scan of patient 0009 taken on day 1 of admission (e.g., admission to a hospital). If it is desired to view a lower numbered slice of the CT scan taken on day 1 of admission, the user may select the down arrow button 204 and the screen 200 may display an image 96 of slice 30 from the CT scan of patient 0009 taken on day 1 of the patient's admission, as indicated in the image information 224 depicted in FIG. 46.

Figure 47:
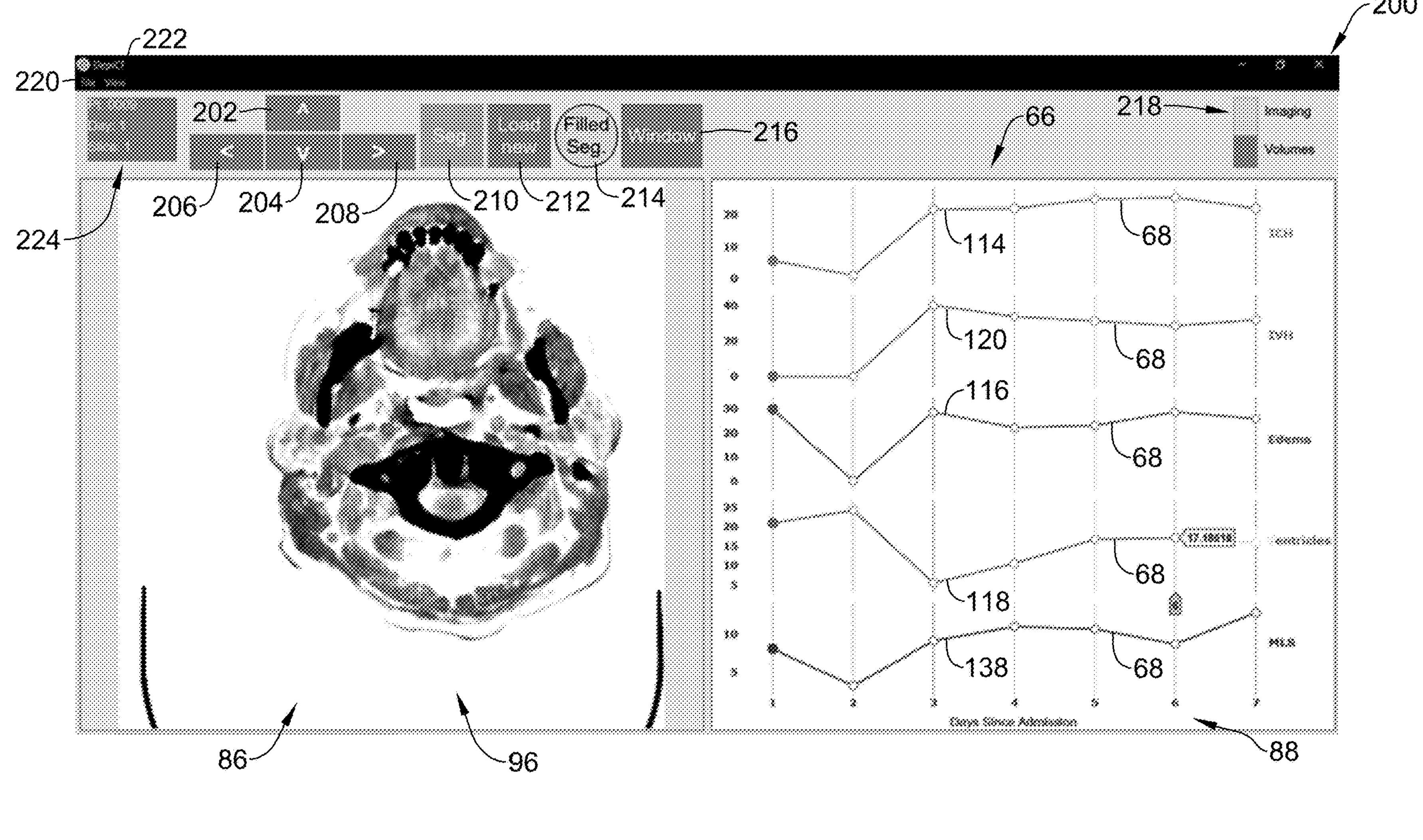
Figure 48:
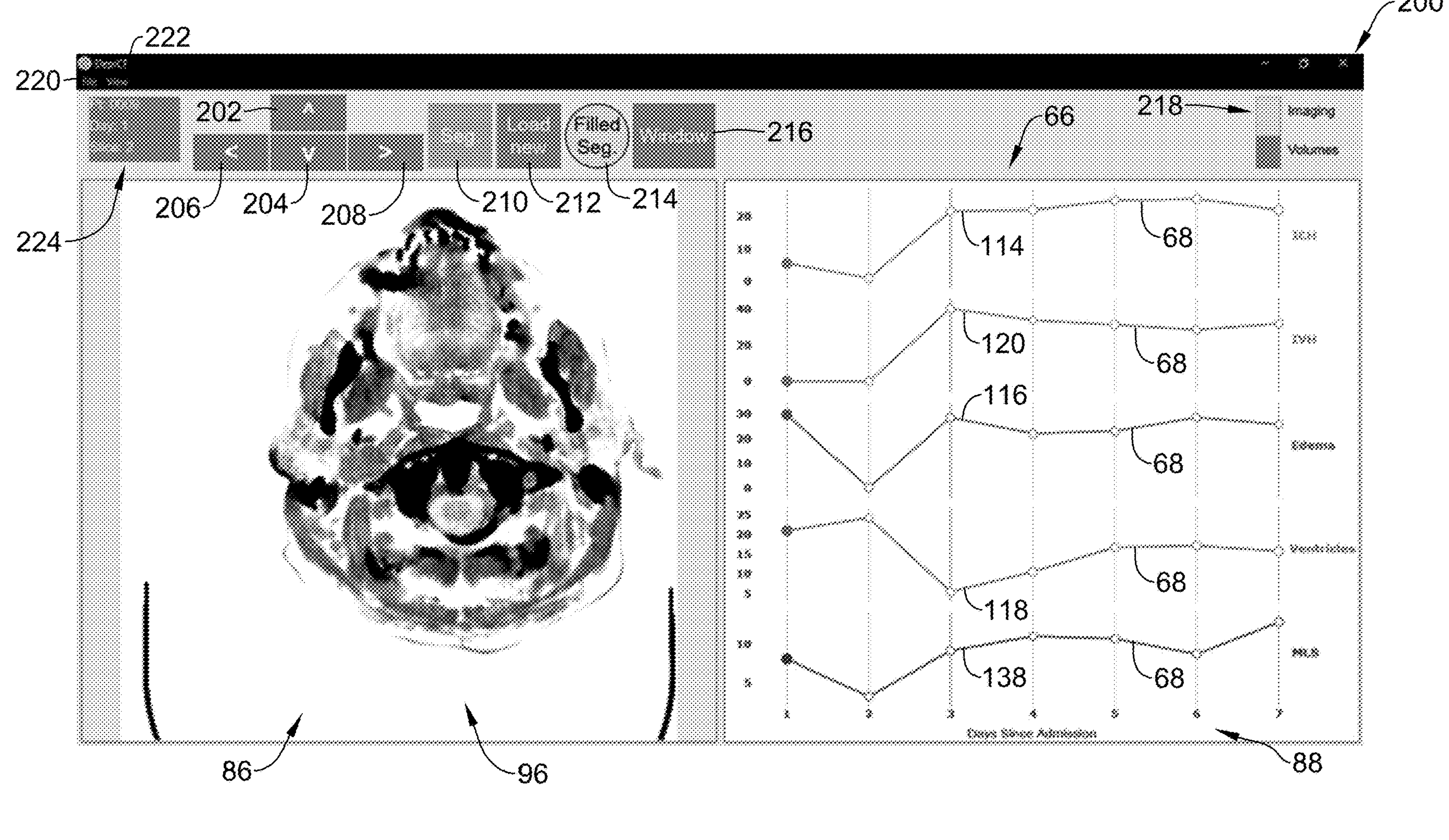

FIG. 47 depicts slice 1 of the CT scan of patient 0009 taken on day 1 of admission. If it is desired to view a higher numbered slice of the CT scan taken on day 1 of admission, the user may select the up-arrow button 202 and the screen 200 may display an image 96 of slice 2 from the CT scan of patient 0009 taken on day 1 of the patient's admission, as indicated in the image information 224 depicted in FIG. 48.

A patient may have a CT scan taken multiple times while admitted. For example, as represented by the open circles on the trend lines 68, the patient may have a CT scan take on each day of a seven (7) day admission. When multiple CT scans of the patient are taken over time, a user may observe progression of one or more parameters over time by viewing scans in a chronological order or other suitable order. Although the trend lines 68 show how values of various parameters have changed over time, viewing images 96 associated with the values of the trend lines 68 may facilitate a user's understanding of how the patient's condition is progressing.

FIGS. 49-52 depict switching the image 96 between a slice (e.g., slice 1) of different scans (e.g., CT scans, etc.) for a selected patient (e.g., patient 0009) using back and forward arrow buttons 206, 208. Although arrows are depicted and described for moving between patient scans, other techniques for moving between patient scans are contemplated including, but not limited to, selecting scans from a scan pane, a scroll bar, swiping, and/or other suitable techniques for switching between available patient scans.

Figure 49:
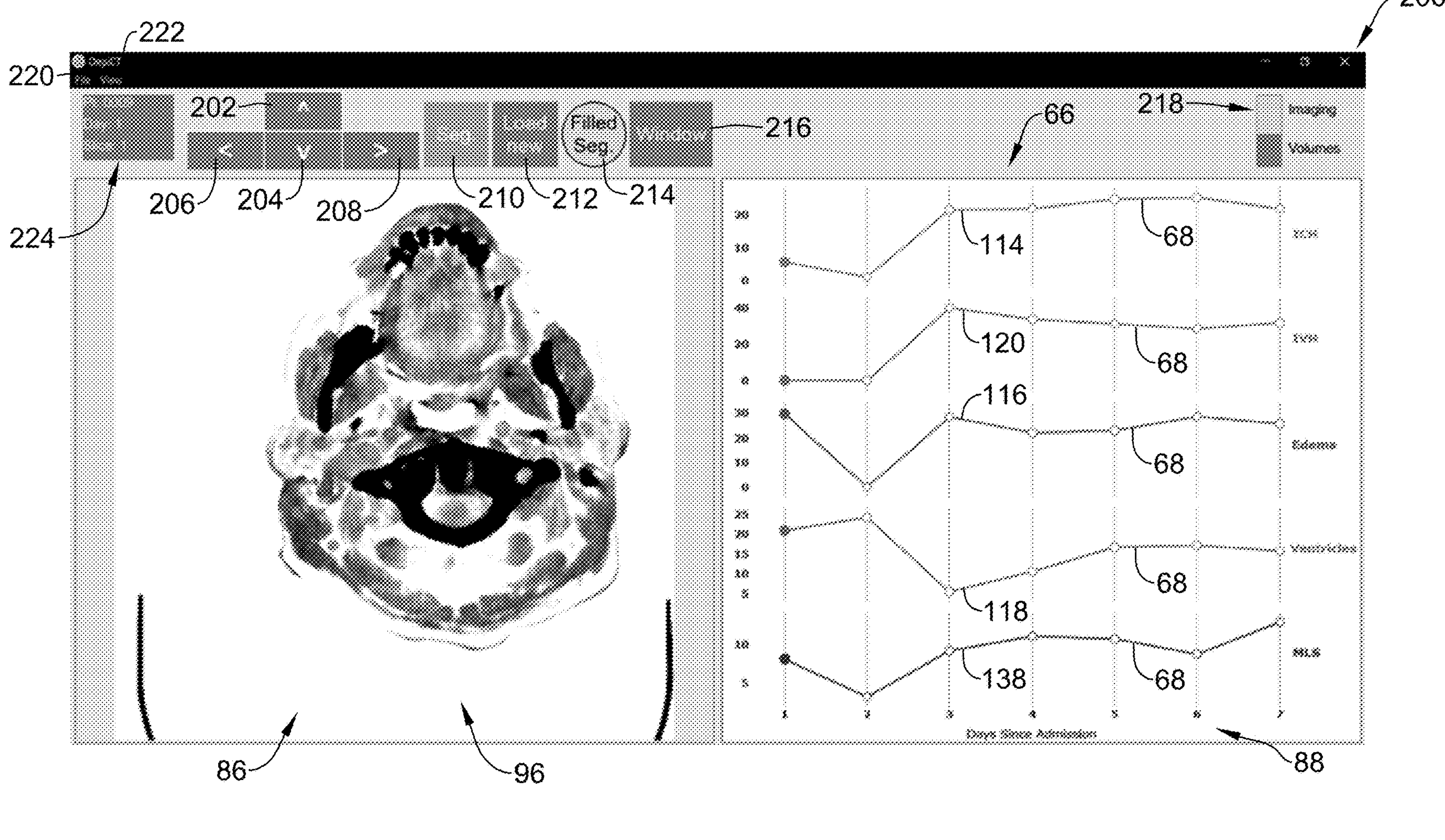
Figure 50:
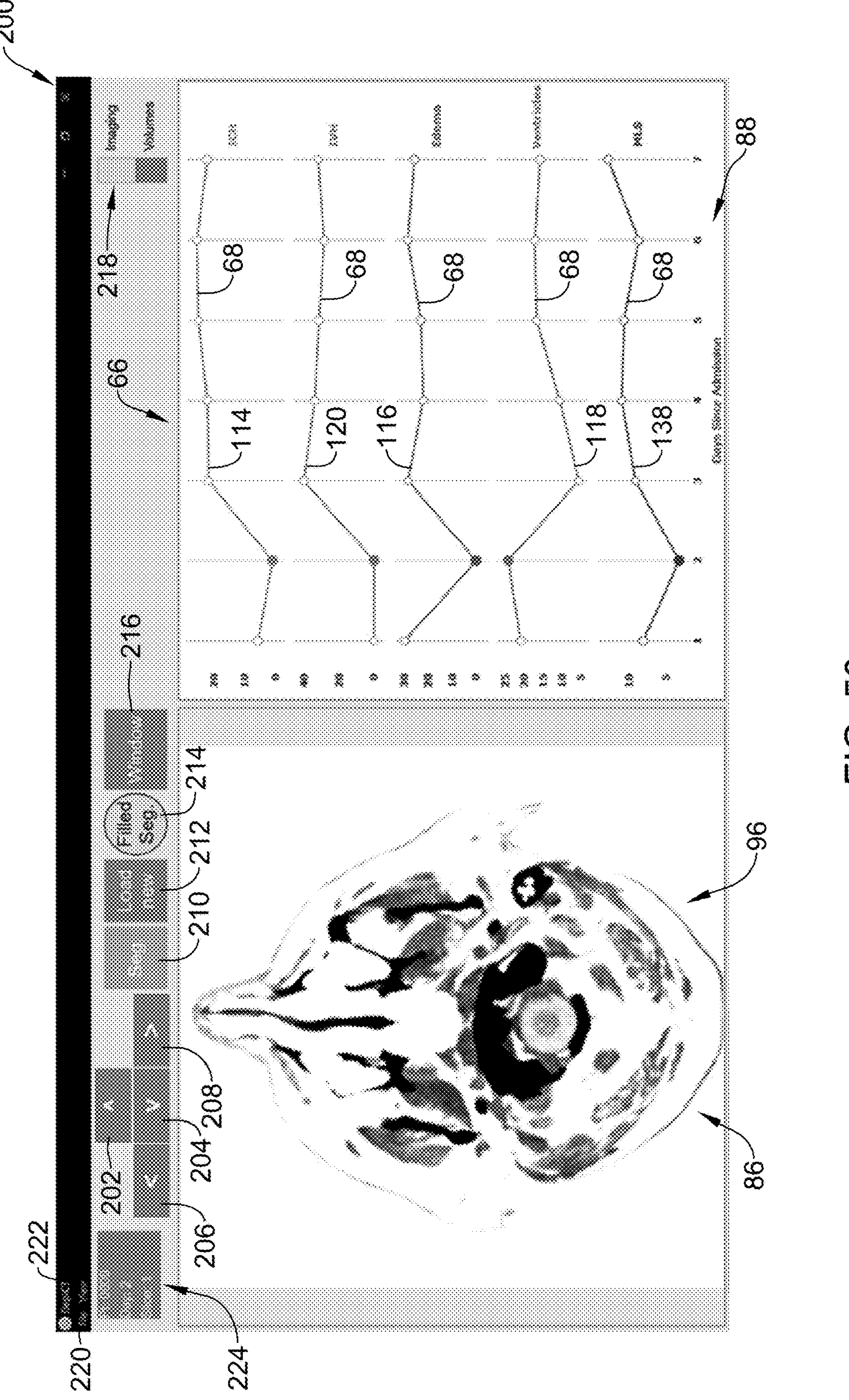

FIG. 49 depicts slice 1 of a CT scan of patient 0009 taken on day 1 of admission (e.g., admission to a hospital). If it is desired to view a slice of a CT scan taken on a subsequent day of admission, the user may select the forward arrow button 208 and the screen 200 may display an image 96 of slice 1 from the CT scan of patient 0009 taken on day 2 of the patient's admission, as indicated in the image information 224 depicted in FIG. 50.

Figure 51:
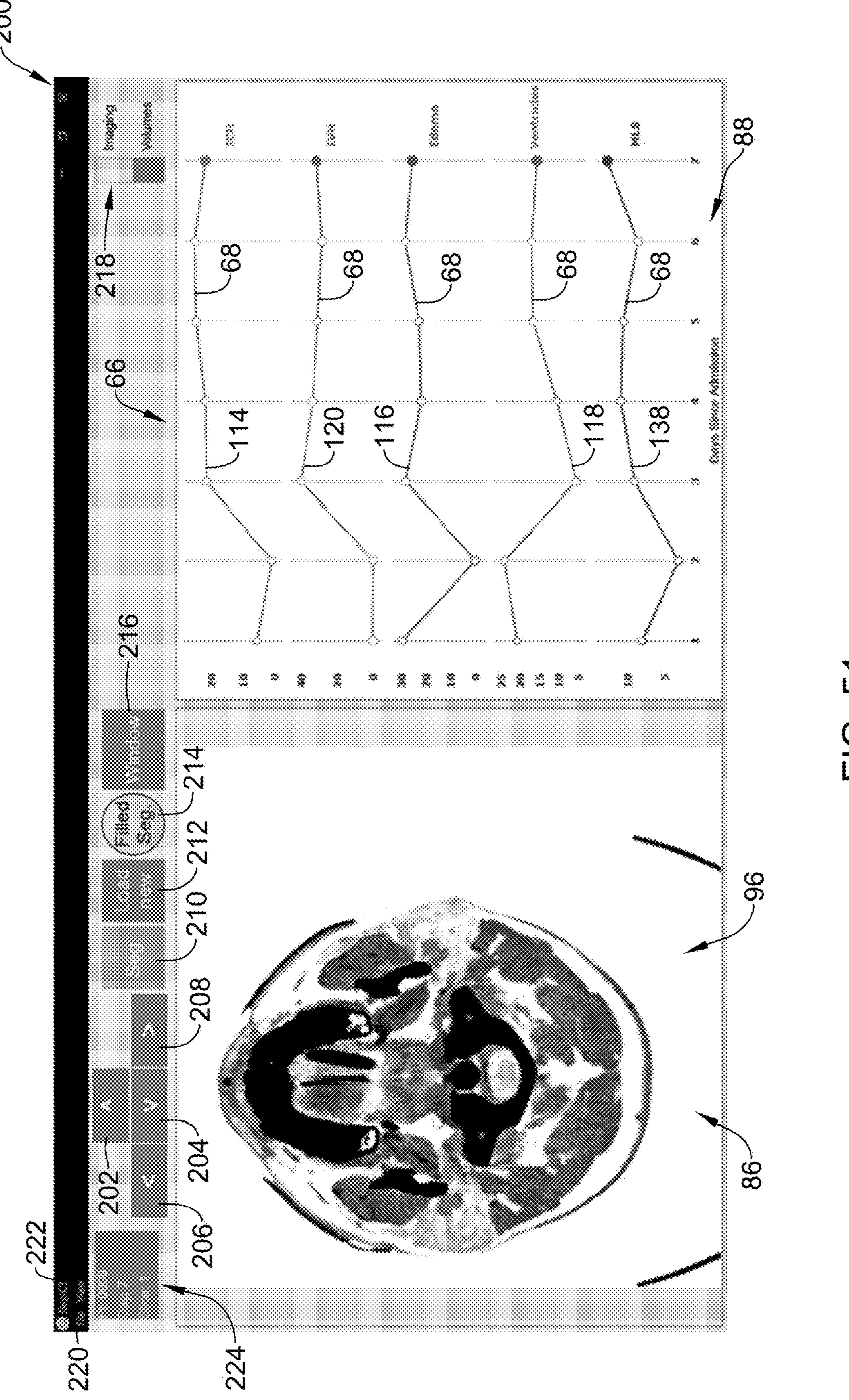
Figure 52:
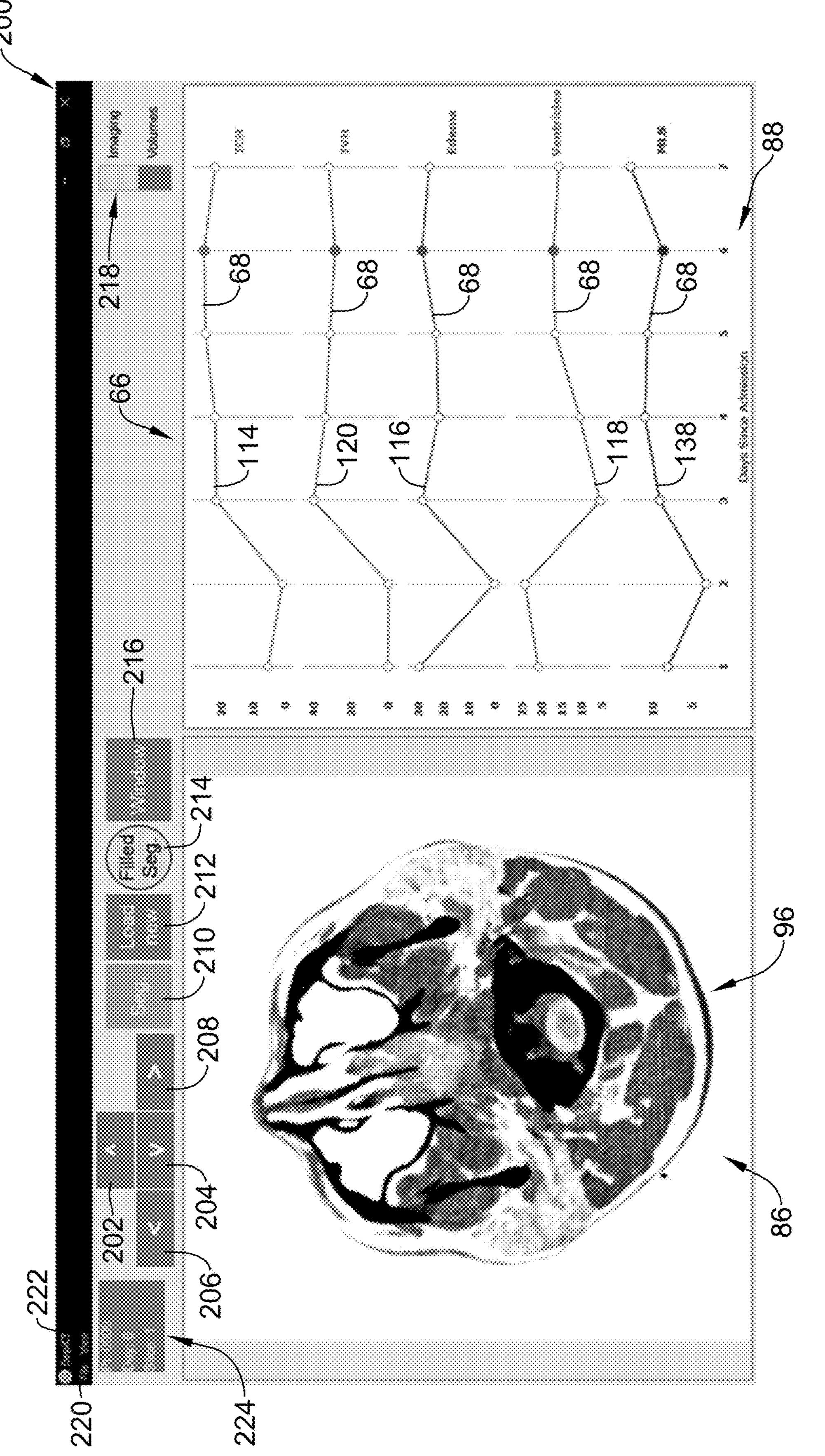

FIG. 51 depicts slice 1 of a CT scan of patient 0009 taken on day 7 of admission. If it is desired to view a slice of a CT scan taken on a previous day of admission, the user may select the backward arrow button 206 and the screen 200 may display an image 96 of slice 1 from the CT scan of patient 0009 taken on day 6 of the patient's admission, as indicated in the image information 224 depicted in FIG. 52.

Figure 53:
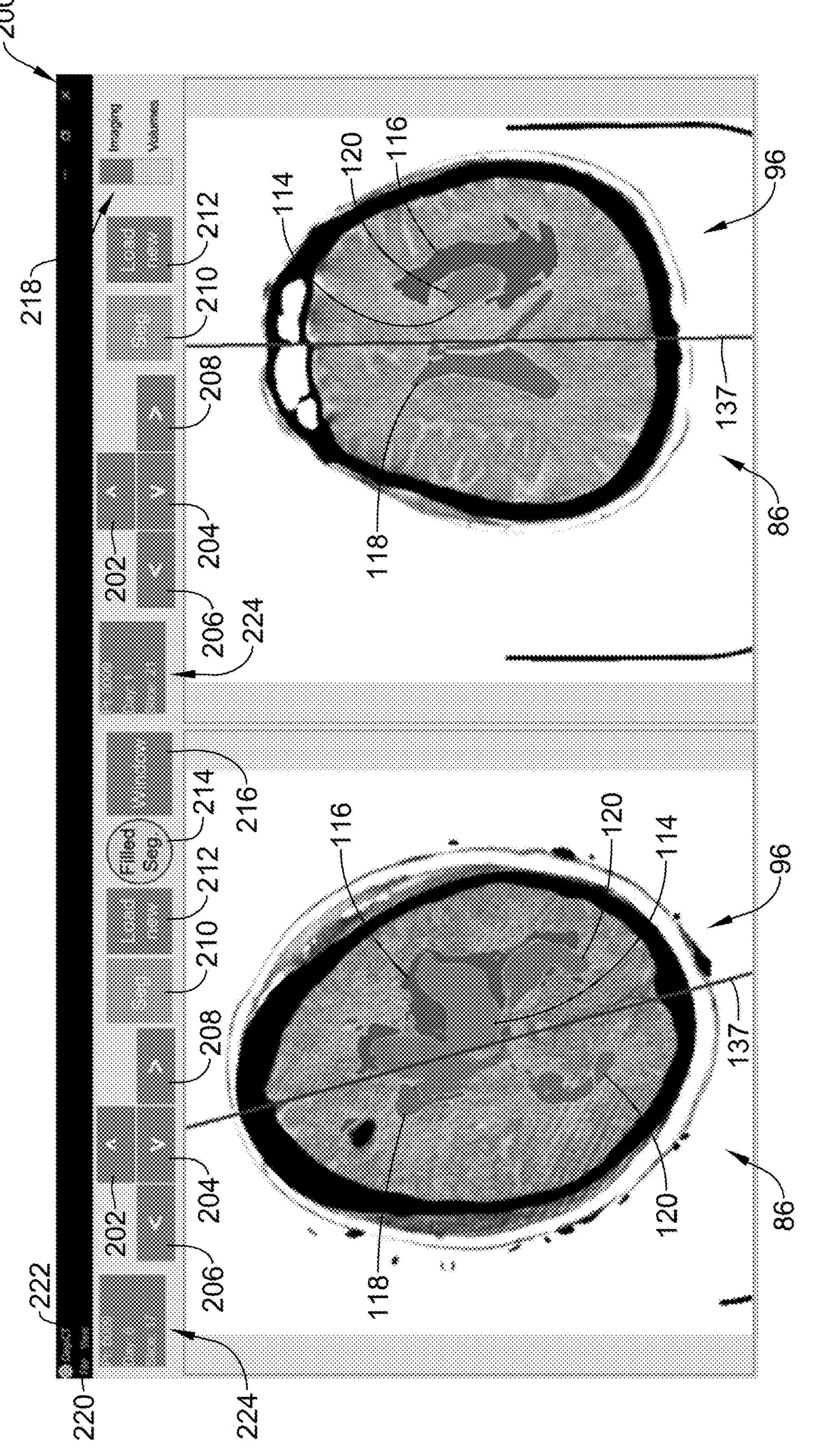

FIG. 53 depicts a screen 200 with two image panes 86. In some cases, more than two image panes 86 may be utilized or otherwise displayed. Viewing images of the patient or multiple patients side by side may facilitate comparing conditions of the patient over time and/or comparing one patient condition to a condition of a different patient or the same patient at a different time.

A user may switch between volumes and/or trendlines 68 on a parameter pane 66 and a second image 96 on an image pane 86 being displayed next to the first image 96 (e.g., as depicted in FIGS. 27-52) by selecting the image/parameter button 218 to toggle to the other screen not currently depicted. However, other configurations are contemplated for moving between a parameter pane 66 and a second image pane 86.

A first image pane 86 (e.g., on the left in FIG. 53) depicts an image 96 of slice 17 of a CT scan of patient 0009 taken on day 6 of an admission. A second image pane 86 (e.g., on the right in FIG. 53) depicts an image 96 of slice 21 of a CT scan of patient 0009 taken on day 1 of the admission. As is evident from the image information 224 for each image pane 86, the screen 200 may depict images 96 of the patient that are taken on different days and/or that are different slices of a CT scan, where the slices and scans may be navigable in each image pane 86 using arrow buttons 202, 204, 206, 208, as discussed herein, and/or navigable in one or more other suitable manners. Though not required, the slices and/or scans may be navigable together with a single set of controls (e.g., when in a synchronous view mode and/or in other suitable instances). Further, the segmenting and the image depicted may be individually selected per image pane 86 by selecting the segmenting button 210 and the load new patient button 212, respectively. In some cases, the windowing and/or the whether the parameters on the images 96 are filled, outlined, or both filled and outlined may be determined for each image 96 based on a single selection (e.g., as depicted in FIG. 53 due to only one segmentation fill button 214 and one windowing button 216 on the screen 200) or may be determined individually.

As mentioned, when the new patient screen 200 depicts two image panes 86, the new patient screen 200 may be navigated using a synchronous view mode. FIGS. 54-61 depict entering the synchronous view mode, along with examples of navigation through the different scans or portions of the scans of the patients when in the synchronous view mode.

In the depicted configuration of the screen 200, a user may select the View button 222 to cause the dropdown View window 225 to appear on the screen 200. As discussed herein, the dropdown View window 225 may include one or more selectable options including, but not limited to, "Change Window", "Segmentation Opacity", "Toggle Segmentations", "Labels", "Overlay Both Segmentations", "Synchronous View", etc. A user may select the Synchronous View option 229 by clicking on the option 229, touching the option 229, or otherwise selecting the option 229, as depicted in FIG. 54, to enter the synchronous view mode.

Figure 54:
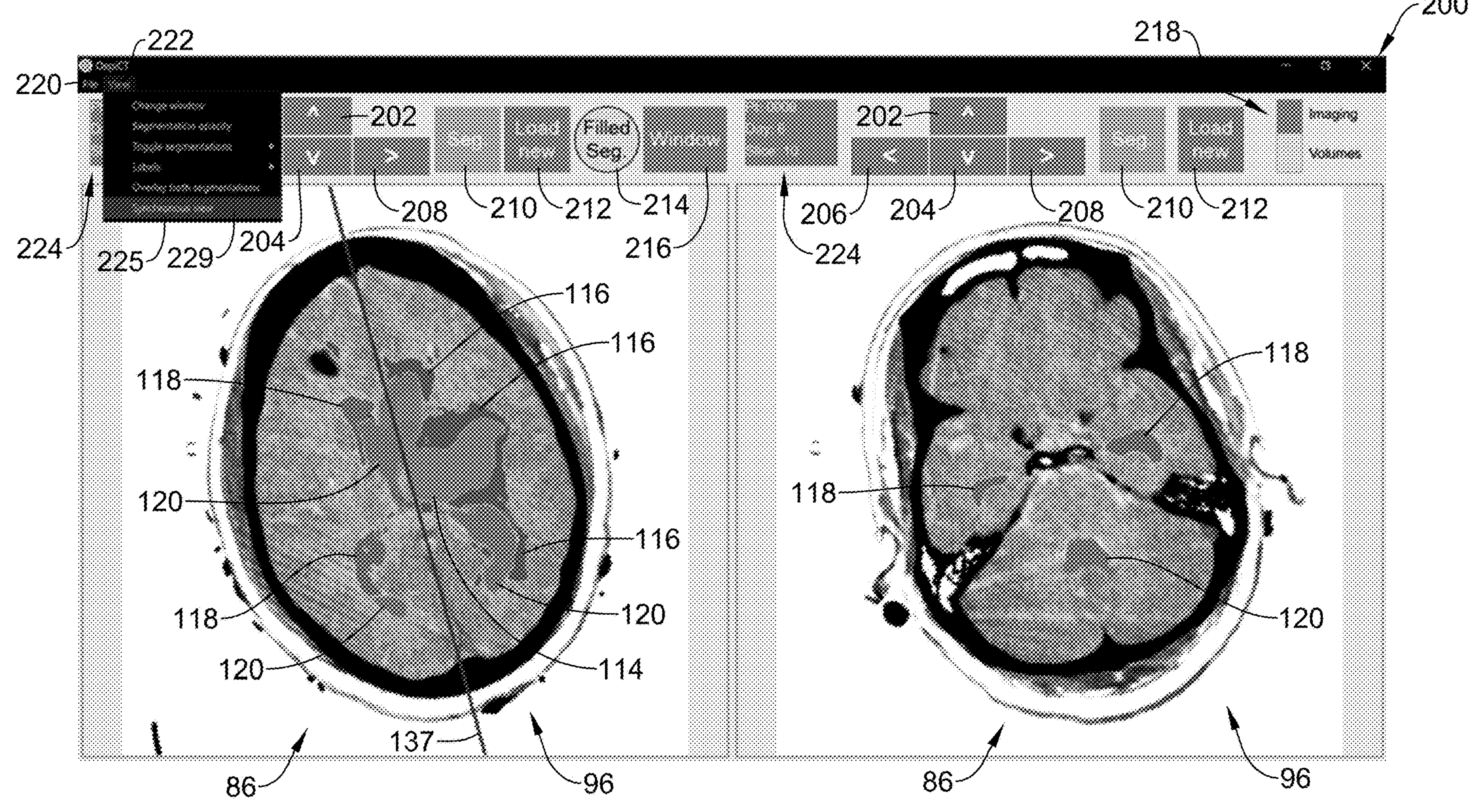
Figure 55:
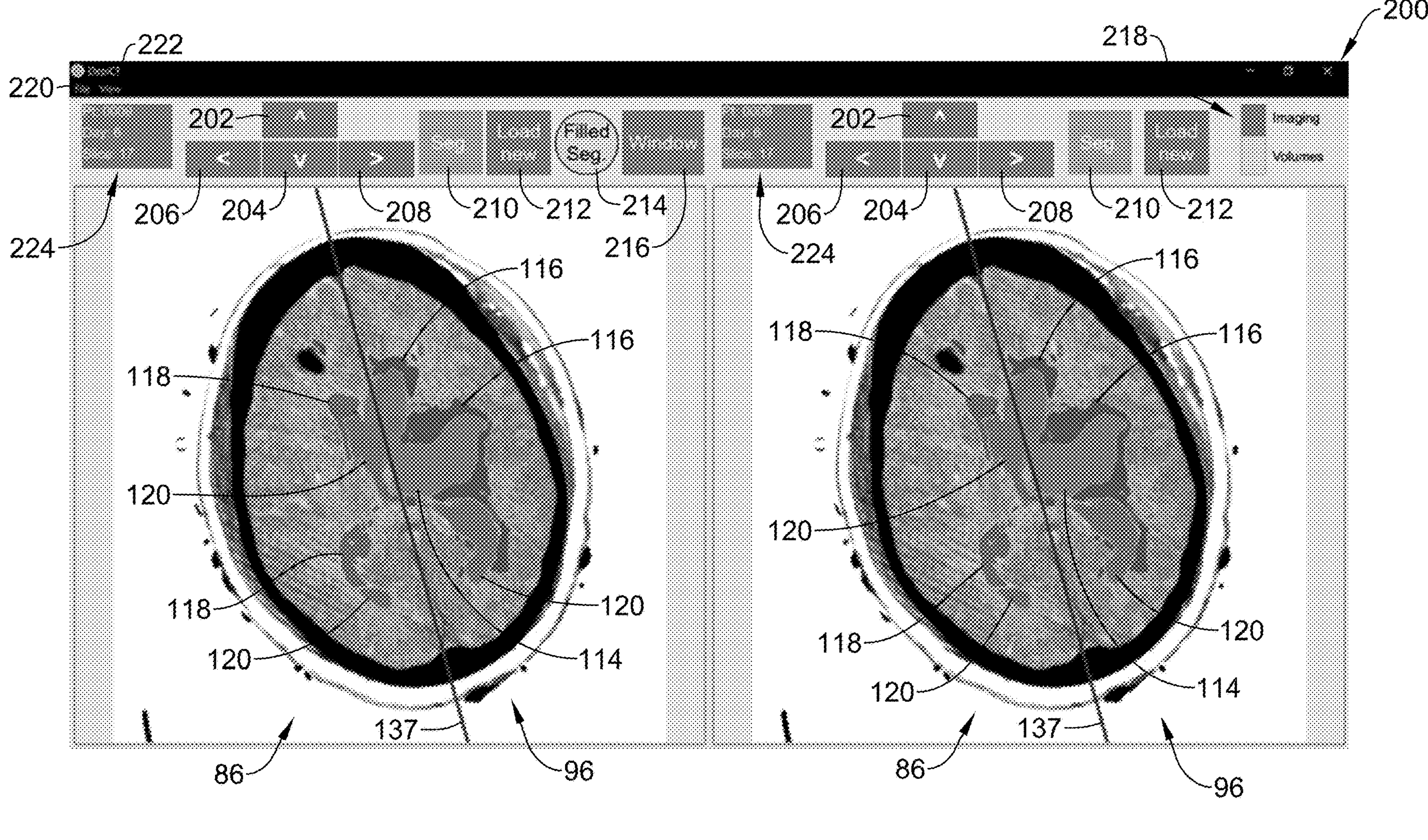

Once the Synchronous View option 229 has been selected, the images 96 depicted in the image panes 86 may automatically update to an image 96 depicted in a synchronous view image pane 86 (e.g., the left image pane 86 or other suitable image pane 86) prior to entering the synchronous view mode, as depicted in moving from the patient viewer screen 200 of FIG. 54 to the patient viewer screen 200 of FIG. 55. However, this is not required and the images 96 depicted in the image panes 86 may remain the same as they were prior to entering the synchronous view mode of the image 96 in the second or other image pane 86 (e.g., the right image pane 86 or other secondary image pane 86) may update to an image 96 associated with the image 96 in the synchronous view image pane 86. For example, in response to entering a synchronous view mode, the image 96 in the secondary image pane 86 may update to an image 96 of a slice of a second scan that may be anatomically registered with a slice of a scan in the image 96 depicted in the synchronous view image pane 86. When so configured, the synchronous view mode may automatically show a view of a same or similar location of a patient's brain or other anatomical feature from the different scans in the image panes 96.

Figure 56:
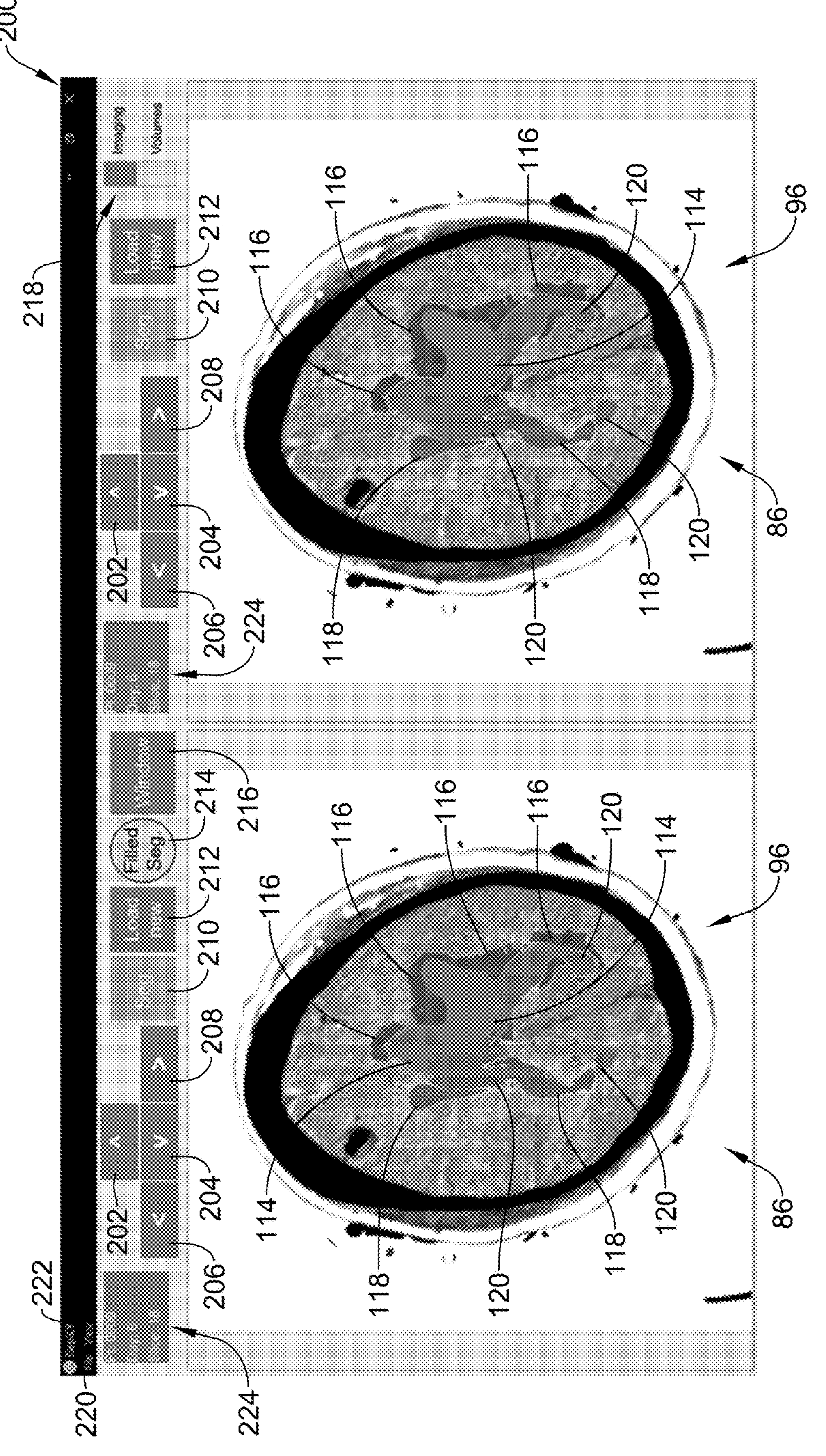

In some cases, interactions with the navigation controls (e.g., arrows 202, 204, 206, 208) and/or other controls associated with one of the depicted image panes 86 may cause synchronous changes with one or more of the image panes 86. In one example, FIG. 56 depicts a response to a selection of one of the up arrows 202 to depict a next slice of the scans depicted in the image panes 86 (e.g., see image information 224 in FIG. 55 (patient 0009, Day 6, Slice 17) relative to image information 224 in FIG. 56 (patient 0009, Day 6, slice 18)). In another example, FIG. 57 depicts a response to a selection of one of the down arrows 204 to depict a previous slice of the scans depicted in the image panes 86 (e.g., see image information 224 in FIG. 55 (patient 0009, Day 6, Slice 17) relative to image information 224 in FIG. 57 (patient 0009, Day 6, slice 16)).

Figure 57:
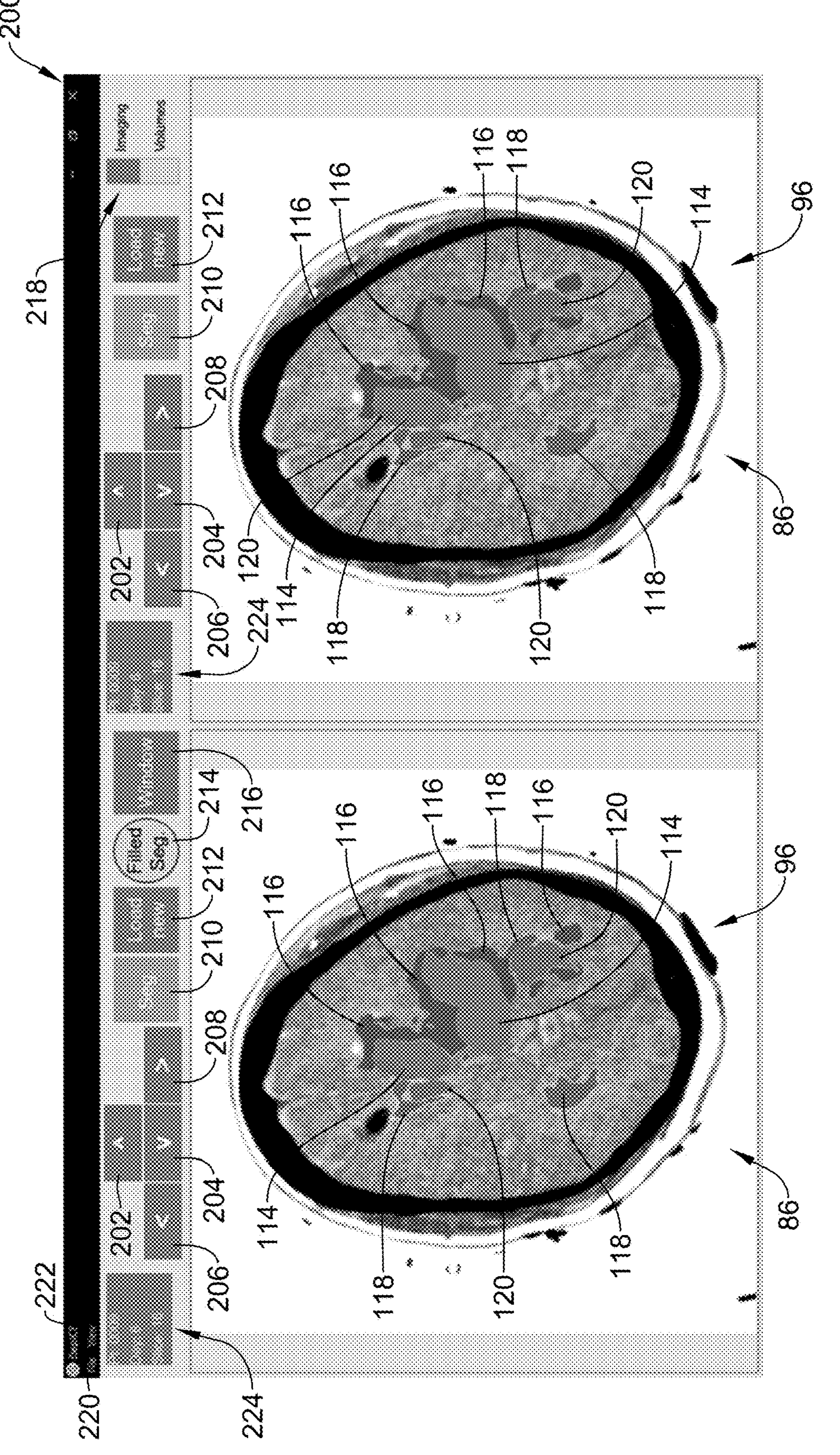

Although FIGS. 56 and 57 depict synchronous navigation from a same starting image 96 in each image pane 86 (e.g., patient 0009, Day 6, Slice 17), it is contemplated that synchronous navigation with the images 96 in each image pane 86 may start with different images 96 in the respective panes. Such synchronous navigation may facilitate comparing scans from the same patient taken over time, comparing different slices of a single scan, comparing a scan of a first patient to a scan of a second patient (e.g., where the first patient and the second patient may have a similar diagnosis or injury, the first and the second patient may have one or more similar parameters, etc.), and/or comparing other suitable sets of scans.

Figure 58:
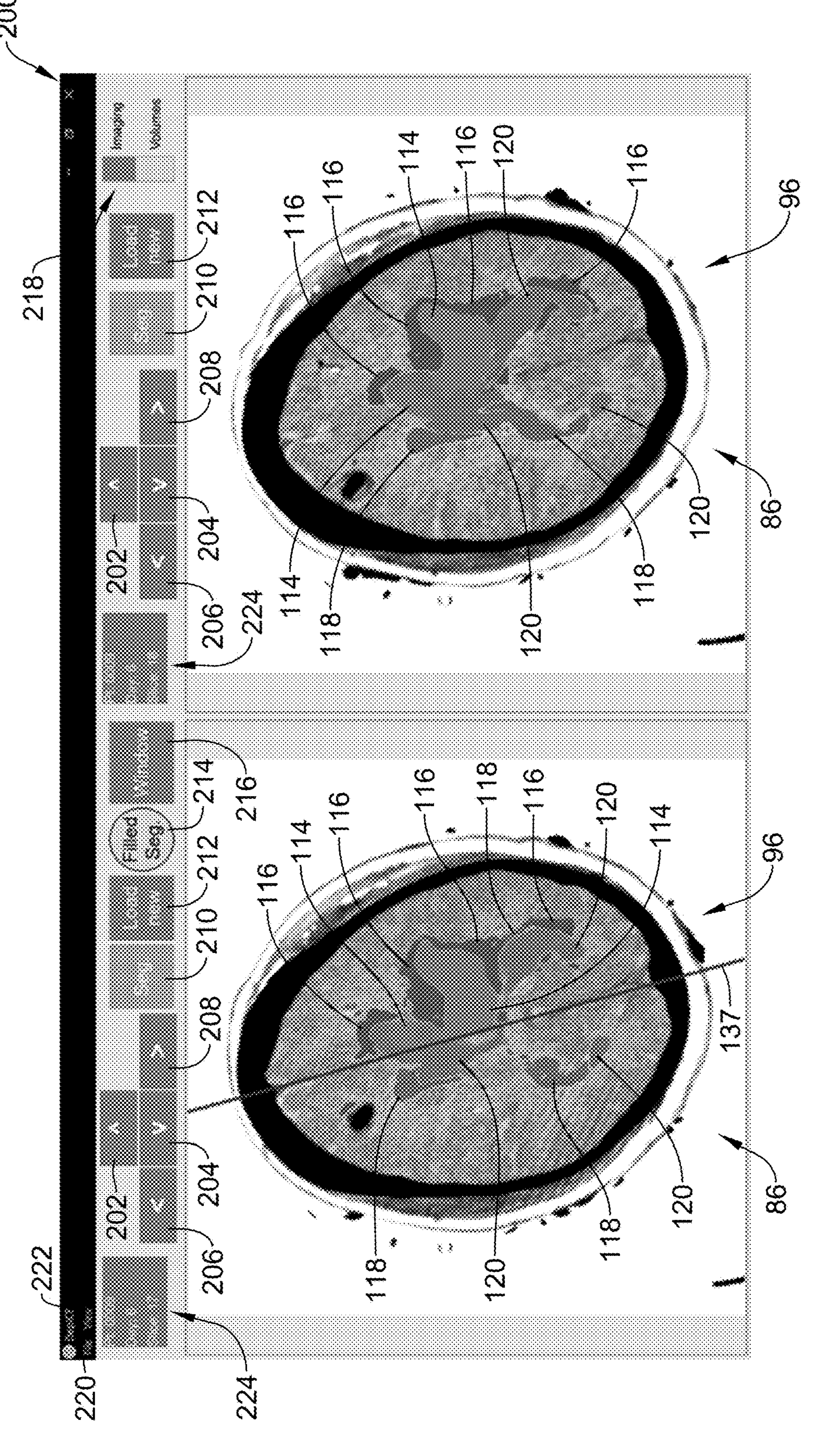
Figure 59:
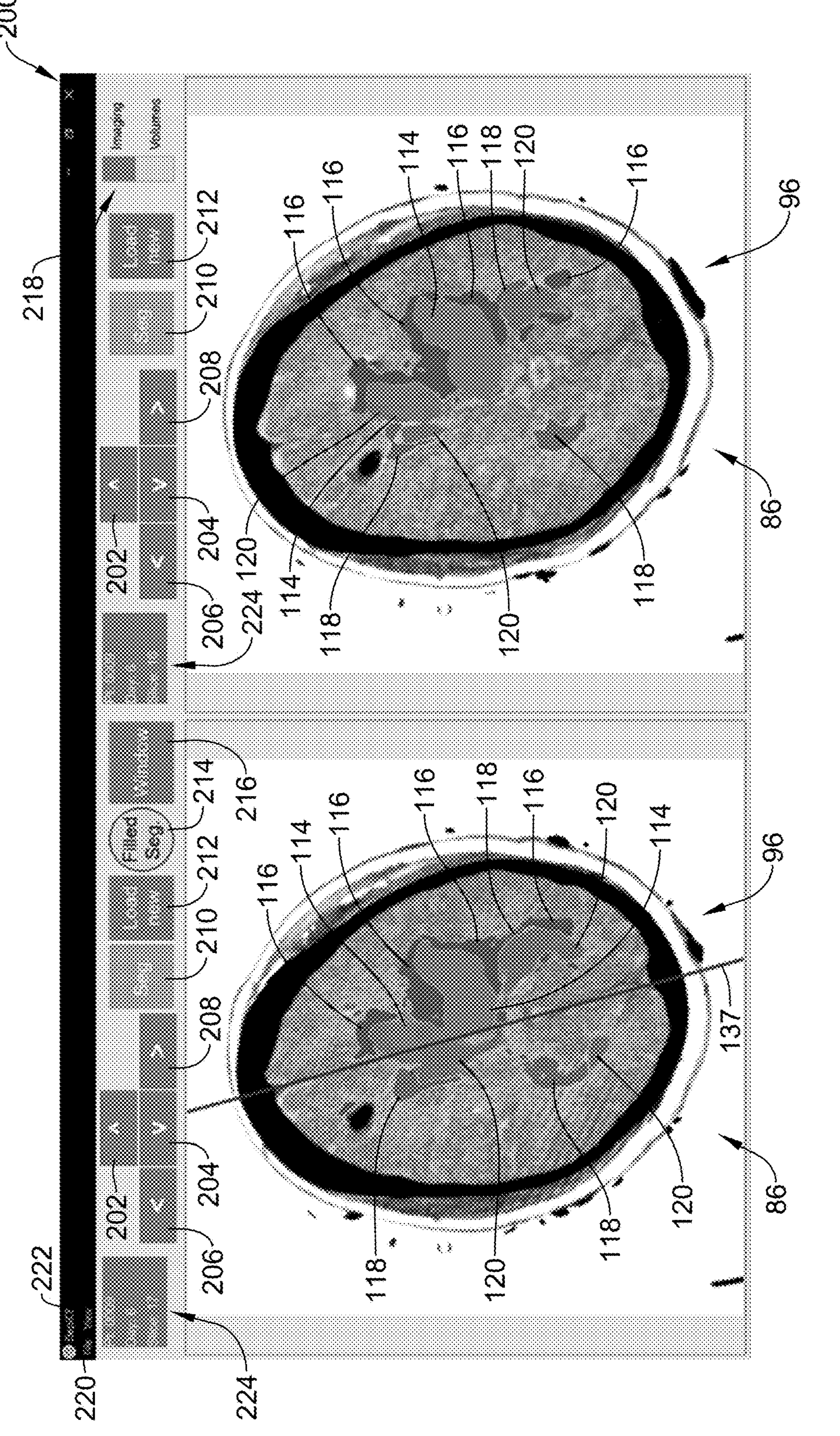

In some cases, interactions with the navigation controls and/or other controls associated with a first of the depicted image panes 86 (e.g., the right pane in FIGS. 58 and 59) may cause asynchronous changes in the first image page 86 with respect to at least one other image pane 86 and interactions with the navigation controls and/or other controls associated with at least one other of the depicted image panes 86 (e.g., the left pane in FIGS. 58 and 59) may cause synchronous changes in the one other of the depicted image panes 86 with respect to at least one additional image pane 86. In one example, FIG. 58 depicts a response to a selection of the up arrow 202 in the image pane 86 on the right of the patient viewer screen 200 to depict a next slice of the scan in the image pane 86 on the right relative to the image 96 in the image pane 86 on the left (e.g., see image information 224 for the left and right image panes 86 in FIG. 55 (patient 0009, Day 6, Slice 17) relative to the image information 224 in the image panes 86 on the left on the left (patient 0009, Day 6, Slice 17) and on the right (patient 0009, Day 6, slice 18) in FIG. 58). In another example, FIG. 59 depicts a response to a selection of the down arrow 204 in the image pane 86 on the right of the patient viewer screen 200 to depict a previous slice of the scan in the image pane 86 on the right relative to the image 96 in the image pane 86 on the left (e.g., see image information 224 for the left and right image panes 86 in FIG. 55 (patient 0009, Day 6, Slice 17) relative to the image information 224 in the image pane 86 on the left (patient 0009, Day 6, Slice 17) and on the right (patient 0009, Day 6, slice 16) in FIG. 59).

Figure 60:
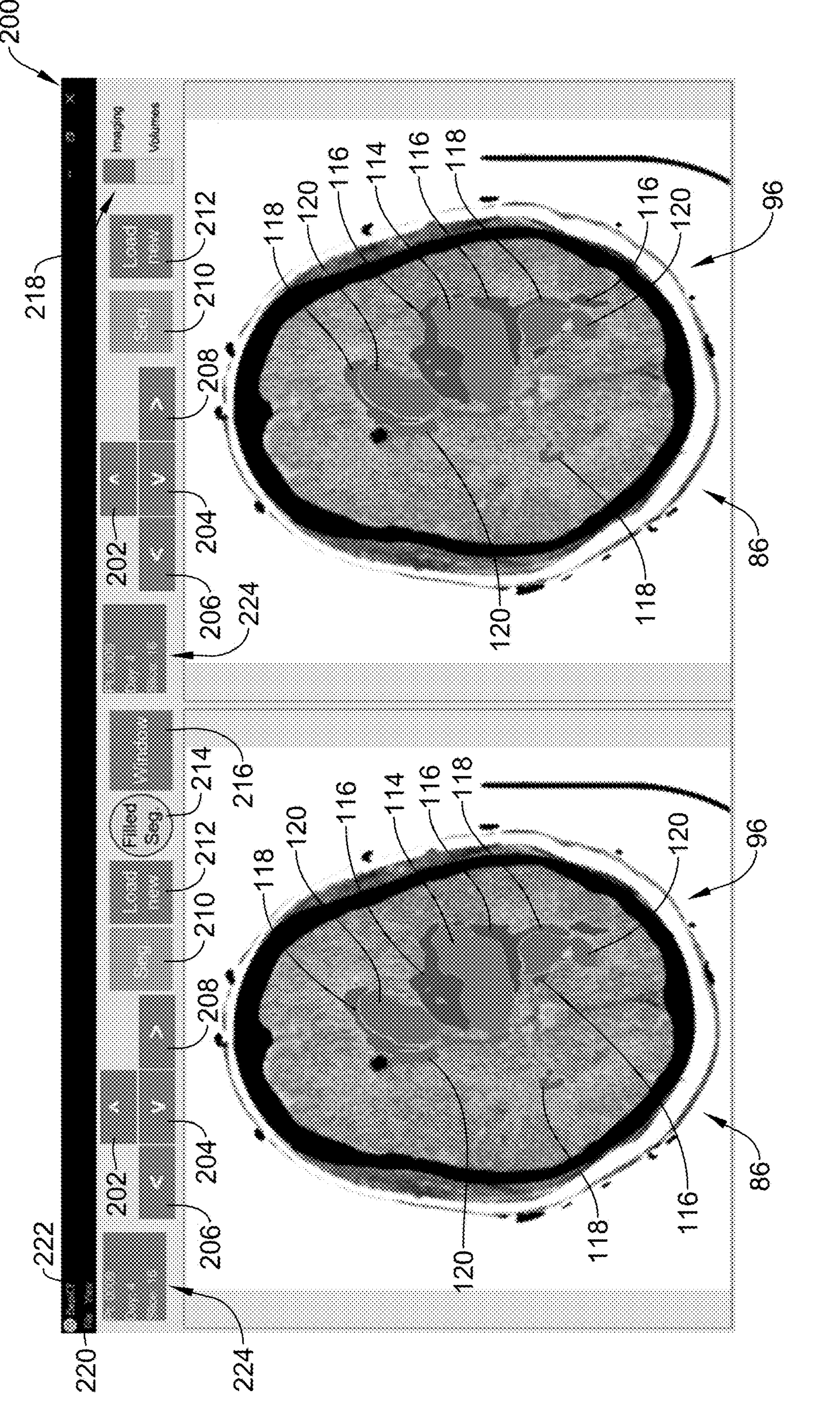

As discussed herein, the navigation tools of image pane 86 may be utilized to switch between scans of a patient. In one example, selection of the backward arrow 206 or the forward arrow 208 may cause the image 96 depicted in an associated image pane 96 to move to a previous scan or a next scan, respectively. In some cases, when in the Synchronous View mode, selection of a navigation tool associated with an image pane 86 may cause a change in scans depicted in two or more of the image panes 86 on the patient viewer screen 200. In one example, FIG. 60 depicts a response to a selection of a new scan of the patient from controls associated with a first image pane 86 (e.g., the left image pane 86) to change the scan depicted in both of the image panes 86 (e.g. the left and right image panes 86) in the patient viewer screen 200 (e.g., compare image information 224 in FIG. 55 to image information 224 in FIG. 60). In the example, FIG. 61 depicts a response to a selection of a new scan of the patient from controls associated with a second image pane 86 (e.g., the right image pane 86) to change the scan depicted in the image panes 86 from which the new scan was selected (e.g., compare image information 224 in FIG. 55 to image information 224 in FIG. 60).

In some cases, an asynchronous navigation and/or other suitable change in the image pane 86 (e.g., in the right image pane 86 in the examples discussed herein) may cause the system to move out of the synchronous view mode. However, this is not required and the system may remain in synchronous view mode after asynchronous navigation or other suitable change in the image pane 86, such that a navigation or other suitable change in an image pane 86 associated with synchronous navigation (e.g., in the left image pane 86 in the examples discussed herein) causes the same image to be depicted in two or more image panes 86 of the patient viewer screen 200.

Various screens and displays have been discussed and described herein. Although features of these screens and displays have been discussed with respect to a particular screen or display, such features may be used in other screens and/or displays unless expressly indicated otherwise.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It should be noted that delivery sheath and delivery catheter may be used interchangeably for purposes of this description. The exemplary drawings are for purposes of illustration only and the dimensions, positions, order and relative sizes reflected in the drawings attached hereto may vary.

U.S. Patent Application Pub. No. US 2016/0051801 is incorporated herein by reference. U.S. Pat. No. 8,435,204 is incorporated herein by reference. U.S. Patent Application No. 62/568,412 is incorporated herein by reference. U.S. Patent Application No. 62/598,846 is incorporated herein by reference.

The above specification, examples and data provide a complete description of the structure and use of exemplary embodiments of the disclosure as claimed below. Although various embodiments of the disclosure as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure.

What is claimed is:

1. A patient management system, the system comprising:
a controller configured to store data related to one or more patient parameters of a patient, the controller is programmed to:
display a first image on a display of a user interface, the first image is an image from a plurality of images of a brain of the patient taken over time;
display values of or related to the one or more patient parameters in one or more trend lines over time on the display and adjacent the first image;
receive a selection of a second image from the plurality of images of the brain of the patient; and
in response to receiving the selection of the second image, automatically switch from displaying the first image to displaying the second image and identify a value of or related to each of the one or more patient parameters in the one or more trend lines, wherein the value is associated with the second image and an area of the second image associated with the value is identified in the second image.

2. The system of claim 1, wherein the selection of the second image includes a selection of an indicator associated with a value along a trend line of the one or more trend lines.

3. The system of claim 1, wherein the controller is further programmed to:
display a timeline adjacent the one or more trend lines, the timeline including one or more indicators of when each of the plurality of images of the brain of the patient were taken, and
wherein the selection of the second image includes a selection of an indicator of the one or more indicators of when each of the plurality of images of the brain of the patient were taken.

4. The system of claim 1, wherein the selection of the second image includes a selection of an arrow key displayed on the user interface.

5. The system of claim 1, wherein the display is a touchscreen display and the selection of the second image includes a user swiping the touchscreen display.

6. The system of claim 1, wherein the controller is programmed to:
obtain data related to two or more patient parameters; and
display values of the two or more patient parameters in two or more trend lines over a timeline common to the two or more trend lines of the values of the two or more patient parameters.

7. The system of claim 1, wherein the controller is programmed to receive a selection to edit a configuration of the display.

8. The system of claim 1, wherein the controller is programmed to provide a notification if a value of the one or more patient parameters reaches or goes beyond a threshold.

9. The system of claim 8, wherein the notification comprises a control signal for a treatment module and the control signal is configured to initiate a treatment protocol.

10. The system of claim 1, wherein the controller is programmed to display an indicator on the one or more trend lines of the one or more patient parameters, the indicator indicates when an image of the plurality of images of the brain of the patient was taken and/or is to be taken.

11. The system of claim 1, wherein the controller is programmed to display an indicator along a timeline common to the one or more trend lines of the values of the one or more patient parameters, the indicator indicates when an image of the plurality of images of the brain of the patient was taken and/or is to be taken.

12. A computer readable medium having stored thereon in a non-transitory state a program code for use by a computing device, the program code causing the computing device to execute a method of operating a patient management system, the method comprising:
displaying a first image on a display, the first image is an image from a plurality of images of a brain of a patient taken over time;
displaying values of or related to one or more patient parameters in one or more trend lines over time on the display and adjacent the first image;
receiving a selection of a second image from the plurality of images of the brain of the patient; and
in response to receiving the selection of the second image, automatically switching from displaying the first image to displaying the second image on the display and identifying a value of or related to each of the one or more patient parameters in the one or more trend lines, wherein the value is associated with the second image and an area of the second image associated with the value is identified in the second image.

13. The computer readable medium of claim 12, wherein receiving the selection of the second image includes receiving a selection of an indicator associated with a value along a trend line of the one or more trend lines.

14. The computer readable medium of claim 12, wherein the method further comprises:
displaying a timeline adjacent the one or more trend lines, the timeline including one or more indicators of when each of the plurality of images of the brain of the patient were taken, and
wherein receiving the selection of the second image includes receiving a selection of an indicator of the one or more indicators of when each of the plurality of images of the brain of the patient were taken.

15. The computer readable medium of claim 12, wherein receiving the selection of the second image includes receiving a selection of an arrow key displayed on the display.

16. The computer readable medium of claim 12, wherein the display is a touchscreen display and receiving the selection of the second image includes receiving a user swipe of the touchscreen display.

17. The computer readable medium of claim 12, wherein the method further comprises outputting a control signal for a treatment module when a value of the one or more patient parameters reaches or goes beyond a threshold, the control signal is configured to initiate a treatment protocol.

18. A computer readable medium having stored thereon in a non-transitory state a program code for use by a computing device, the program code causing the computing device to execute a method of operating a patient management system, the method comprising:
graphically displaying a first image from a plurality of images from one or more CT scans of a brain of a patient on a display of a user interface, at least a portion of the plurality of images are taken over time;
identifying one or more locations in the plurality of images, the one or more locations in the plurality of images are associated with one or more patient parameters related to the brain of the patient;
graphically indicating the one or more locations on the first image displayed; and in response to receiving a user selection of a second image of the plurality of images, graphically displaying the second image with the one or more locations indicated thereon.

19. The computer readable medium of claim 18, wherein the method further comprises:

identifying values of the one or more patient parameters based on the one or more locations identified in at least the first image and the second image; and graphically displaying at least the values of the one or more patient parameters identified from the first image and the second image adjacent an image graphically displayed from the plurality of images.

20. The computer readable medium of claim 19, wherein the user selection of the second image is a selection of an indicator associated with a value of the one or more patient parameters identified based on the second image.

* * * * *